US008138356B2

(12) United States Patent
Chaudhary et al.

(10) Patent No.: US 8,138,356 B2
(45) Date of Patent: Mar. 20, 2012

(54) CHEMICAL INHIBITORS OF INHIBITORS OF DIFFERENTIATION

(75) Inventors: Jaideep Chaudhary, Smryna, GA (US); William A. Garland, San Clemente, CA (US)

(73) Assignee: Angiogeney, Inc., New York, NY (US)

( * ) Notice: Subject to any disclaimer, the term of this patent is extended or adjusted under 35 U.S.C. 154(b) by 486 days.

(21) Appl. No.: 12/253,009

(22) Filed: Oct. 16, 2008

(65) Prior Publication Data

US 2009/0226422 A1    Sep. 10, 2009

(51) Int. Cl.
*C07D 409/02* (2006.01)
*A61K 31/33* (2006.01)
(52) U.S. Cl. .......................................... 549/49; 514/183
(58) Field of Classification Search .................... 549/49; 514/183
See application file for complete search history.

(56) References Cited

U.S. PATENT DOCUMENTS

| 3,907,826 | A | 9/1975 | Stoss et al. |
| 3,988,448 | A | 10/1976 | Bowman et al. |
| 2004/0106792 | A1* | 6/2004 | Tauri et al. .................... 540/607 |

FOREIGN PATENT DOCUMENTS

| EP | 0146243 A1 | 6/1985 |
| GB | 1414207 | 11/1975 |

OTHER PUBLICATIONS

Han, J. 'Advances in Characterization of Pharmaceutical Hydrates' Trends in Bio/Pharmaceutical Industry, vol. 3, p. 25-29, 2006.*
Stella et al 'Prodrugs: Challenges and Rewards, Part 1' Biotechnology: Pharmaceutical Aspects, p. 24, 2007.*
Vippagunta et al 'Crystalline solids' Advanced Drug Delivery Reviews, vol. 48, p. 3-26, 2001.*
PCT/ISA/210—International Search Report (PCT/US2008/011881), Apr. 27, 2009.

* cited by examiner

*Primary Examiner* — Brandon Fetterolf
*Assistant Examiner* — Christopher R Stone
(74) *Attorney, Agent, or Firm* — Jeffrey J. King; Patent Networks Law Group PLLC

(57) ABSTRACT

The present invention provides identification of inhibitors of inhibitors of differentiation (Id) for use in the treatment and prevention of diseases in mammals. The inhibitors of Id are effective alone in the treatment of a variety of cellular proliferative disorders including, but not limited to, diseases such as cancer, arthritis, age-related macular degeneration, psoriasis, neoplasms, angiomas, endometriosis, obesity, age-related macular degeneration, retinopathies, restenosis, scaring, fibrogenesis, fibrosis, cardiac remodeling, pulmonary fibrosis, scleroderma, failure associated with myocardial infarction, keloids, fibroid tumors and stenting. Additionally, these compounds are effective in blocking angiogenesis in tumor development, inducing apoptosis in malignant cells, inhibiting proliferation of cancer cells, increasing the effectiveness of chemotherapeutic agents, regulating transcriptional activity, reducing inflammation, increasing cellular differentiation, modulating ETS domain transcription factors, modulating PAX transcription factors, modulating TCF-ETS domain transcription factors, down regulating RAF-1/MAPK, upregulating JNK signaling pathways, and modulating cellular transformation.

1 Claim, 10 Drawing Sheets

CHEMICAL INHIBITORS OF INHIBITORS OF DIFFERENTIATION

TECHNICAL FIELD

The present invention relates to compositions and methods for controlling cellular determination and differentiation in mammalian subjects. More specifically, the invention relates to compositions and methods for inhibiting inhibitors of differentiation (Id), particularly inhibiting inhibitors of basic helix-loop-helix transcription factors and the use of such methods and compositions in the treatment and/or prevention of diseases in mammals.

BACKGROUND

The basic helix-loop-helix (bHLH) family of transcriptions factors is a structurally complex and functionally heterogeneous group in which over 400 bHLH-domain containing proteins have been identified. bHLH proteins are known to be involved with myriad cellular processes including neurogenesis, myogenesis, cell proliferation, cell fate determination, and tissue differentiation among other essential developmental processes.

The highly conserved bHLH domain that characterizes members of this family consists of two amphipathic helixes separated by a loop that mediates homo- and/or hetero-dimerization (Ledent, V., O. Paquet, and M. Vervoort, Genome Biol 2002; 3: RESEARCH0030). The basic (b) component of the bHLH domain includes a short component of mainly basic residues that bind to a consensus DNA sequence element, the "E-box" (CANNTG). The helix-loop-helix (HLH) component of the bHLH proteins is the structural mediator of the sequestering process and comprises a highly hydrophobic oligomerization region of approximately 50 residues which allows the formation of homodimeric or heterodimeric complexes between different family members. The relative placement of the bHLH domain in a particular protein can vary significantly. For example, the bHLH domain can be located at the COOH end of the protein (as in the Myc proteins), at the NH end (as in Sim), or in an intermediate position (MyoD).

Inhibitor of differentiation (Id) genes encode members of the helix loop helix (HLH) family of transcription factors that inhibit transcription by forming inactive heterodimers with bHLH proteins (Benezra, R., et al., Cell 1990; 61: 49-59). Typically, bHLH proteins form heterodimers with other bHLH proteins and their basic domain binds to the E box, activating transcription. Id proteins lack the basic domain necessary for DNA binding and act primarily as dominant-negative regulators of bHLH transcription factors by sequestering and/or preventing DNA binding of ubiquitously expressed (e.g., E12, E47, E2-2) or cell-type-restricted (e.g., Tal-1, MyoD) factors.

While Id proteins generally act as negative regulators of differentiation, depending on the specific cell lineage and developmental stage of the cell, Id proteins can also act as positive regulators. (Lasorella, A., et al., Cancer Res, 2002. 62(1): p. 301-6) Because bHLH proteins are mainly involved in the regulation of the expression of tissue specific and cell cycle related genes, Id-mediated sequestration or repression of bHLH proteins serves to block differentiation and to promote cell cycle activation. In general, expression of Id mRNA is highest in proliferating cells including carcinomas and low or usually absent in quiescent or terminally differentiated cells. (Coppe, J. P., A. P. Smith, and P. Y. Desprez, Exp Cell Res, 2003. 285(1): p. 131-45; Sikder, H. A., et al., Cancer Cell, 2003. 3(6): p. 525-30; de Candia, P., R. Benezra, and D. B. Solit, Adv Cancer Res, 2004. 92: p. 81-94; Fong, S., R. J. Debs, and P. Y. Desprez, Trends Mol Med, 2004. 10(8): p. 387-92; Wong, Y. C., X. Wang, and M. T. Ling, Apoptosis, 2004. 9(3): p. 279-89; Ruzinova, M. B. and R. Benezra, Trends Cell Biol, 2003. 13(8): p. 410-8)

The four known Id proteins (Id1, Id2, Id3 and Id4) have highly conserved HLH domains, but divergent N- and C-terminal domains. In addition to modulating bHLH proteins, they have also been shown to modulate the activity of non-bHLH proteins such as retinoblastomas, MIDA1, ETS-domain transcription factors, Pax2, Pax5, Pax8 and ELK-1.

Discovery of molecules capable of inhibiting Id proteins has been difficult due to the location of the HLH-bHLH interactions in the nucleus and the relatively delocalized nature of the protein-protein interactions underlying the interaction. Additionally, the high degree of homology between HLH and bHLH domains makes the isolation of anti-Id molecules that are not also Ids challenging. Inhibiting Id expression through antisense or siRNA has been considered (Henke E, et al., Nat. Biotechnol., 2008. 26(1): p 91-100.) however these approaches are not desirable for commercialization and widespread use. There is therefore a need for additional means for inhibiting Id expression.

SUMMARY OF THE EXEMPLARY EMBODIMENTS OF THE INVENTION

Low molecular weight, i.e. less than 2000 Daltons, compounds that inhibit the action of inhibitor of differentiation (Id) proteins but do not inhibit Id binding partners have been identified herein. The methods and compositions herein may use these compounds in the treatment of a variety of cellular proliferative disorders including, but not limited to, diseases such as cancer, arthritis, age-related macular degeneration and psoriasis. Additionally, these compounds may be useful in blocking angiogenesis in tumor development, inducing apoptosis in malignant cells, inhibiting proliferation of cancer cells, increasing the effectiveness of chemotherapeutic agents, regulating transcriptional activity, reducing inflammation, increasing cellular differentiation, modulating ETS domain transcription factors, modulating PAX transcription factors, modulating TCF-ETS domain transcription factors, down regulating RAF-1/MAPK, upregulating JNK signaling pathways, modulating cellular transformation and inhibiting the interaction of Id1 with E47.

The invention achieves these objects and satisfies additional objects and advantages by providing novel and surprisingly effective methods and compositions that inhibit the interactions of Id proteins using the compounds of Formula I and III below as well as pharmaceutically acceptable active salts of said compounds, as well as active isomers, enantiomers, polymorphs, metabolites, solvates, hydrates, and/or prodrugs of said compounds:

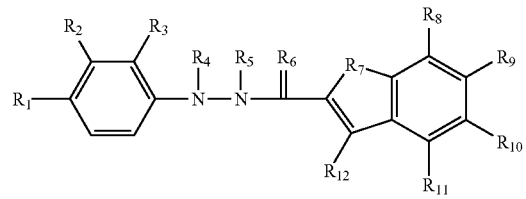

Formula I wherein R₁ may be a substituted or unsubstituted lower hydrocarbon selected from the group consisting of alkyl, alkenyl, alkanoyl, alkynyl, aryl, aroyl, aralkyl, alkylamino, aryloxy, hydrogen, carboxyl, nitro, thioalkoxy, thioaryloxy, thiol, cycloalkenyl cycloalkyl, heterocycloalkyl, heteroaryl, aralkyl, amino acid, peptide, dye, fluorophore, carbohydrate or polypeptide; R2 and R3 may independently, collectively, or in any combination that yields an active anti-Id (apoptosis inducing, cellular proliferation inhibiting, chemotherapeutic enhancing, transcription regulating, anti-inflammatory, cellular differentiation promoting, cellular transformation modulating) composition be a hydrogen, hydroxyl, sulfyhydryl, fluorine, methyl, ethyl, propyl, benzyl, 2-bromovinyl amino, hydroxymethyl, methoxy, halogen, pseudohalogen, cyano, carboxyl, nitro, thioalkoxy, thioaryloxy, thiol, substituted or unsubstituted lower hydrocarbon containing 1 to 20 carbons such as alkoxycarbonyl, alkoxycarbonylamino, amino, amino acid, aminocarbonyl, aminocarbonyloxy, aralkyl, aryloxy, carboxyl, cycloalkenyl, alkyl, cycloalkyl, heterocycloalkyl, aryl, heteroaryl, aralkyl, amino acid, peptide, dye, fluorophore, carbohydrate or polypeptide; R4 and R5 may be may independently, collectively, or in any combination that yields an active anti-Id (apoptosis inducing, cellular proliferation inhibiting, chemotherapeutic enhancing, transcription regulating, anti-inflammatory, cellular differentiation promoting, cellular transformation modulating) composition be an acyl or a substituted or unsubstituted lower hydrocarbon selected from the group consisting of alkyl, alkenyl, alkanoyl, aryl, aroyl, aralkyl or alkylamino; R6 may be a heteroatom such as oxygen, sulfur or nitrogen; R7 may be a heteroatom such as sulfur, nitrogen or oxygen as well as a carbon; R8, 9, 10, 11 and 12 may independently, collectively, or in any combination that yields an active anti-Id (apoptosis inducing, cellular proliferation inhibiting, chemotherapeutic enhancing, transcription regulating, anti-inflammatory, cellular differentiation promoting, cellular transformation modulating) composition be selected from hydrogen, hydroxyl, sulfyhydryl, fluorine, methyl, ethyl, propyl, benzyl, 2-bromovinyl amino, hydroxymethyl, methoxy, halogen, pseudohalogen, cyano and a substituted or unsubstituted lower hydrocarbon containing 1 to 20 carbons.

When more than one R group is present, the R group may be selected from any of the stated groups so as to be the same or different. In additional embodiments, two or more R groups may be joined together. In some embodiments, R2 and R3 may be members of a 5, or 6, member exocyclic ring structure. In other embodiments, R3 and R4 may be members of a 5, or 6, member exocyclic ring structure. In further embodiments, R5 and R6 may be members of a 5 or 6 member exocyclic ring structure. In additional embodiments, R11 and R12 may be members of a 5 or 6 member exocyclic ring structure. In some embodiments, if R7 is nitrogen, R6 and R7 may be members of a 5 or 6 member exocyclic ring structure. In other embodiments, R6 and R12 may be members of a 5 or 6 member exocyclic ring structure.

In exemplary embodiments, an anti-Id (apoptosis inducing, cellular proliferation inhibiting, chemotherapeutic enhancing, transcription regulating, anti-inflammatory, cellular differentiation promoting, cellular transformation modulating) composition of Formula I may be N'-(4-isopropylphenyl)-1-benzothiophene-2-carbohydrazide as shown in Formula II and derivatives thereof.

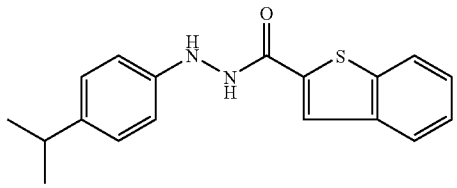

Formula II

Novel and surprisingly effective methods and compositions that inhibit the interactions of Id proteins but do not inhibit Id binding partners may additionally comprise compounds of Formula III, below, as well as pharmaceutically acceptable active salts of said compounds, as well as active isomers, enantiomers, polymorphs, metabolites, solvates, hydrates, and/or prodrugs of said compounds:

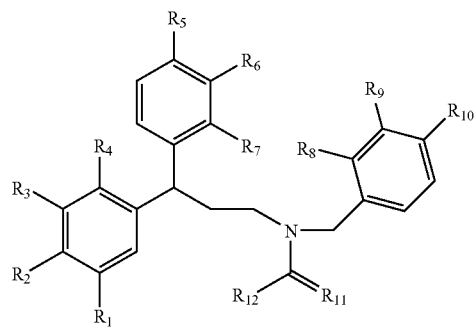

Formula III wherein $R_1$, $R_2$, $R_3$, $R_4$, $R_5$, $R_6$, $R_8$, $R_9$, and $R_{10}$ may independently, collectively, or in any combination that yields an active anti-Id (apoptosis inducing, cellular proliferation inhibiting, chemotherapeutic enhancing, transcription regulating, anti-inflammatory, cellular differentiation promoting, cellular transformation modulating) composition be hydrogen, hydroxyl, sulfyhydryl, fluorine, methyl, ethyl, propyl, benzyl, 2-bromovinyl amino, hydroxymethyl, methoxy, halogen, pseudohalogen, cyano, carboxyl, nitro, thioalkoxy, thioaryloxy, thiol, substituted or unsubstituted lower hydrocarbon containing 1 to 20 carbons; alkoxycarbonyl, alkoxycarbonylamino, amino, amino acid, aminocarbonyl, aminocarbonyloxy, aralkyl, aryloxy, carboxyl, cycloalkenyl, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, amino acid, peptide, dye, fluorophore, carbohydrate or polypeptide; $R_7$ may be selected from hydrogen, hydroxyl, benzoyl; substituted benzoyl or hydroxyl substituted with unsubstituted lower hydrocarbon containing 1 to 20 carbons; $R_{11}$ may be a heteroatom such as oxygen, sulfur or nitrogen; $R_{12}$ may be a lower hydrocarbon independently selected from the group consisting of alkyl, alkenyl, alkanoyl, alkynyl, aryl, aroyl, aralkyl, alkylamino, aryloxy, hydrogen, carboxyl, nitro, thioalkoxy, thioaryloxy, thiol, cycloalkenyl substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, amino acid, peptide, dye, fluorophore, carbohydrate or polypeptide.

When more than one R group is present, the R group may be selected from any of the stated groups so as to be the same or different. In additional embodiments, two or more R groups may be joined together. In some embodiments, R4 may become a member of a 5 or 6 member ring structure with neighboring rings.

In exemplary embodiments, Formula III may be N-[3-(1,3-benzodioxol-5-yl)-3-(2-methoxyphenyl)propyl]-N-benzylpropanamide as shown in Formula IV, below and derivatives thereof.

Formula IV

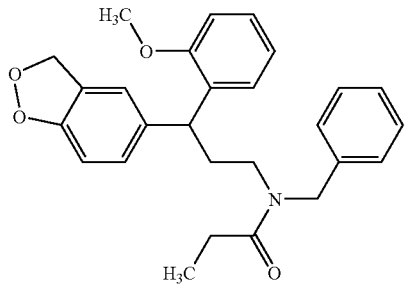

N-[3-(1,3-benzodioxol-5-yl)-3-(2-methoxyphenyl)propyl]-N-benzylpropanamide, may be a racemic mixture. This mixture can be resolved using standard methods and each enantiomer may be used individually as a therapeutic. The addition of another asymmetric center in the molecule may create diastereomers.

Useful anti-Id (apoptosis inducing, cellular proliferation inhibiting, chemotherapeutic enhancing, transcription regulating, anti-inflammatory, cellular differentiation promoting, cellular transformation modulating) and related compounds and derivatives of Formulas I, II, III and IV within the formulations and methods of the invention include, but are not limited to, other pharmaceutically acceptable active salts of said compounds, as well as active isomers, enantiomers, polymorphs, solvates, hydrates, and/or prodrugs of said compounds.

In exemplary embodiments, the compositions and methods of the invention employ an anti-Id (apoptosis inducing, cellular proliferation inhibiting, chemotherapeutic enhancing, transcription regulating, anti-inflammatory, cellular differentiation promoting, cellular transformation modulating) compound of Formula I and/or III to treat and/or prevent symptoms of cellular proliferative disorders.

Mammalian subjects amenable for treatment with the compositions herein include, but are not limited to, cellular proliferative disease such as cancer, arthritis, age-related macular degeneration, and psoriasis. Additional subjects amenable for treatment with the compositions herein include, but are not limited to, subjects suffering from cellular proliferative disorders that are "hyperproliferative" disorders or other diseases and disorders associated with the uncontrolled proliferation of cells including neoplasms, angiomas, endometriosis, obesity, age-related macular degeneration, retinopathies, restenosis, scaring, fibrogenesis, fibrosis, cardiac remodeling, pulmonary fibrosis, scleroderma, failure associated with myocardial infarction, keloids, fibroid tumors and stenting.

These and other subjects are effectively treated, prophylactically and/or therapeutically, by administering to the subject an Id inhibiting effective amount of an anti-Id (apoptosis inducing, cellular proliferation inhibiting, chemotherapeutic enhancing, transcription regulating, anti-inflammatory, cellular differentiation promoting, cellular transformation modulating) compound of Formula I and/or III, above.

Within additional aspects of the invention, combinatorial formulations and methods are provided which employ an effective amount of an anti-Id (apoptosis inducing, cellular proliferation inhibiting, chemotherapeutic enhancing, transcription regulating, anti-inflammatory, cellular differentiation promoting, cellular transformation modulating) compound in combination with one or more secondary or adjunctive active agent(s) that is/are combinatorially formulated or coordinately administered with an anti-Id (apoptosis inducing, cellular proliferation inhibiting, chemotherapeutic enhancing, transcription regulating, anti-inflammatory, cellular differentiation promoting, cellular transformation modulating) compound to yield an anti-proliferative effective response in the subject. Exemplary combinatorial formulations and coordinate treatment methods in this context employ the anti-Id compound (apoptosis inducing, cellular proliferation inhibiting, chemotherapeutic enhancing, transcription regulating, anti-inflammatory, cellular differentiation promoting, cellular transformation modulating) in combination with one or more additional, chemotherapeutic, toxicity reducing, or other indicated, secondary or adjunctive therapeutic agents. The secondary or adjunctive therapeutic agents used in combination with, e.g., a compound or derivative compound of Formula I and/or III in these embodiments may possess direct or indirect anti-proliferative activity alone or in combination with, e.g. N'-(4-isopropylphenyl)-1-benzothiophene-2-carbohydrazide and/or N-[3-(1,3-benzodioxol-5-yl)-3-(2-methoxyphenyl)propyl]-N-benzylpropanamide, or may exhibit other useful adjunctive therapeutic activity in combination with, e.g., N'-(4-isopropylphenyl)-1-benzothiophene-2-carbohydrazide and/or N-[3-(1,3-benzodioxol-5-yl)-3-(2-methoxyphenyl)propyl]-N-benzylpropanamide.

Useful adjunctive therapeutic agents in these combinatorial formulations and coordinate treatment methods include, for example, anti-cancer and other anti-hyperproliferative agents including chemotherapeutic agents such as, but not limited to, DNA damaging agents and agents that inhibit DNA synthesis including, but not limited to, anthracyclines including doxorubicin, daunorubicin, epirubicin, alkylating agents including bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine, platinum derivatives including cisplatin, carboplatin, cis diamminedichloroplatinum, and telomerase and topoisomerase inhibitors; tubulin-depolymerizing agents including, but not limited to, taxoids such as paclitaxel, docetaxel, BAY 59-8862; anti-metabolites including, but not limited to, capecitabine, chlorodeoxyadenosine, cytarabine (and its activated form, ara-CMP), cytosine arabinoside, dacabazine, floxuridine, fludarabine, 5-fluorouracil, 5-DFUR, gemcitabine, hydroxyurea, 6-mercaptopurine, methotrexate, pentostatin, trimetrexate, and 6-thioguanine; anti-angiogenics including, but not limited to, Avastin, thalidomide, sunitinib, lenalidomide; vascular disrupting agents including, but not limited to, flavonoids/flavones, DMXAA, combretastatin derivatives such as CA4DP, ZD6126, AVE8062A; biologics such as antibodies including, but not limited to, Herceptin, Avastin, Panorex, Rituxin, Zevalin, Mylotarg, Campath, Bexxar, Erbitux; endocrine therapy including, but not limited to, aromatase inhibitors such as 4-hydroandrostendione, exemestane, aminoglutehimide, anastrzole, letozole, anti-estrogens such as Tamoxifen, Toremifine, Raoxifene, Faslodex, and steroids such as dexamethasone; immuno-modulators including, but not limited to, cytokines such as IFN-beta and IL2, inhibitors to integrins, other adhesion proteins and matrix metalloproteinases; histone deacetylase inhibitors; inhibitors of signal transduction such as inhibitors of tyrosine kinases like imatinib; inhibitors of heat shock proteins; retinoids such as all trans retinoic acid; inhibitors of growth factor receptors or the growth factors themselves; anti-mitotic compounds such as navelbine, paclitaxel, taxotere, vinblastine, vincristine, vindesine, and vinorelbine; anti-inflammatories such as COX inhibitors; and cell cycle regulators such as check point regulators and telomerase inhibitors.

Adjunctive therapies additionally may include radiation therapy, surgery, gene therapy, DNA vaccines and therapy, siRNA therapy, anti-angiogenic therapy, immunotherapy, bone marrow transplants, apatamers and other biologics such as antibodies and antibody variants, receptor decoys and other protein-based therapeutics.

The forgoing objects and additional objects, features, aspects and advantages of the instant invention will become apparent from the following detailed description.

BRIEF DESCRIPTION OF THE DRAWINGS

FIG. 8A is from a mouse treated ip daily with DMSO vehicle. FIG. 8B is from a mouse treated ip daily with N-[3-(1,3-benzodioxol-5-yl)-3-(2-methoxyphenyl)propyl]-N-benzylpropanamide. The Matrigel plugs were developed to detect microvessel density using an anti-CD 31 antibody.

DETAILED DESCRIPTION OF EXEMPLARY EMBODIMENTS OF THE INVENTION

Figure 1:
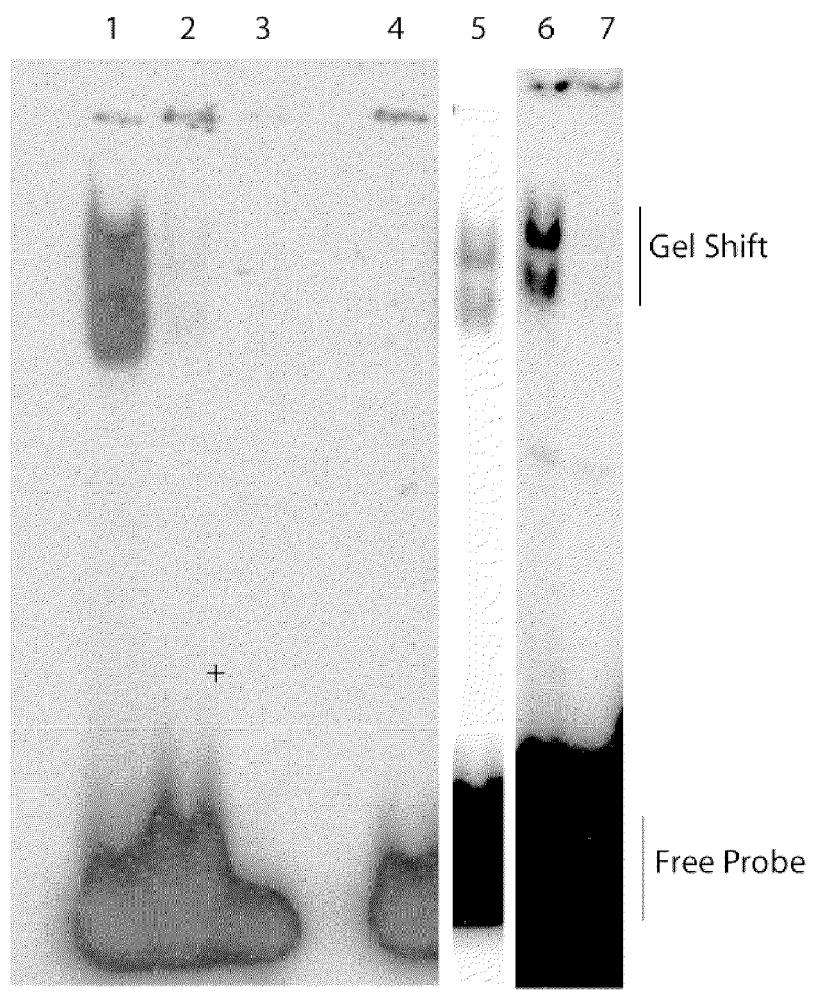
FIG. 1 is an autoradiograph of a gel shift assay showing the ability of E47 to homodimerize and bind to the consensus E box sequence present within the synthetic MCK oligonucleotide (lane 1); the inhibition of the E47-MCK binding in the presence of increasing concentration of recombinant human Id1 (lanes 2 and 3); the effect of the inclusion of a small molecule inhibitor of Id (lanes 5 and 6); and the effect of the inclusion of a small molecule that failed to inhibit it (lane 7).

The instant invention provides the identification and use of compounds involved in cellular differentiation and determination, particularly compounds which may inhibit inhibitors of differentiation (Id) without inhibiting the binding partners of Id. The compositions and methods described herein may be used in modulating a variety of processes including, but not limited to neurogenesis, myogenesis, cell fate determination, cellular proliferation and tissue differentiation in mammalian subjects, including individuals and in vitro, ex vivo, and in vivo mammalian cells, tissues, and organs.

Additionally, the compounds described herein may be useful in inhibiting cellular proliferation, blocking angiogenesis in tumor development, inducing apoptosis in malignant cells, inhibiting proliferation of cancer cells, increasing the effectiveness of chemotherapeutic agents, regulating transcriptional activity, reducing inflammation, increasing cellular differentiation, modulating ETS domain transcription factors, modulating PAX transcription factors, modulating TCF-ETS domain transcription factors, down regulating RAF-1/MAPK, upregulating JNK signaling pathways, modulating Caveolin-1, modifying the activity of proteins whose activity is dependent on Id and modulating cellular transformation.

A broad range of mammalian subjects, including human subjects, are amenable to treatment using the formulations and methods of the invention. These subjects include, but are not limited to, human and other mammalian subjects presenting with cellular proliferative disorders such as cancer, arthritis, age-related macular degeneration, and psoriasis. Additional subjects amenable for treatment with the compositions herein include, but are not limited to, cellular proliferative disorders such as "hyperproliferative" disorders or other diseases and disorders associated with the uncontrolled proliferation of cells including neoplasms, angiomas, endometriosis, obesity, age-related macular degeneration, retinopathies, restenosis, scaring, fibrogenesis, fibrosis, cardiac remodeling, pulmonary fibrosis, scleroderma, failure associated with myocardial infarction, keloids, fibroid tumors and stenting.

Within the methods and compositions of the invention, one or more of the anti-Id compound(s) as disclosed herein is/are effectively formulated or administered as an anti-cellular proliferative agent effective for treating cellular proliferative disorders and/or related disorders. In exemplary embodiments, N'-(4-isopropylphenyl)-1-benzothiophene-2-carbohydrazide and/or N-[3-(1,3-benzodioxol-5-yl)-3-(2-methoxyphenyl)propyl]-N-benzylpropanamide are demonstrated for illustrative purposes to be an anti-cellular proliferative effective agent in pharmaceutical formulations and therapeutic methods, alone or in combination with one or more adjunctive therapeutic agent(s). The present disclosure further provides additional, pharmaceutically acceptable anti-Id (apoptosis inducing, cellular proliferation inhibiting, chemotherapeutic enhancing, transcription regulating, anti-inflammatory, cellular differentiation promoting, cellular transformation modulating, cell migration and metastasis modulating) compounds in the form of a native or synthetic compound, including complexes, derivatives, salts, solvates, isomers, enantiomers, polymorphs, and prodrugs of the compounds disclosed herein, and combinations thereof, which are effective as anti-cellular proliferative therapeutic agents within the methods and compositions of the invention.

Id proteins are regulators of cell fate, growth and differentiation. The four known Id proteins (Id1, Id2, Id3 and Id4) have highly conserved HLH domains but divergent N- and C-terminal domains. The most well characterized action of Id proteins is their ability to heterodimerize with and inhibit the DNA-binding function of members of the basic helix-loop-helix (bHLH) family of transcription factors.

bHLH proteins contain a cluster of amino acids rich in basic residues adjacent to the HLH dimerization motif which mediates DNA binding of homodimeric or heterodimeric HLH complexes. Since the Id proteins lack a basic DNA binding domain, the heterodimers between Id and bHLH proteins cannot bind DNA. Thus the basic mechanism of action of the Id proteins is dominant negative regulation of inhibition of DNA-induced protein synthesis. In addition to regulating bHLH proteins, Id proteins can regulate non-bHLH proteins such as retinoblastomas, MIDA1, ETS-domain transcription factors, Pax2, Pax5, Pax8 and Elk-1.

Evidence suggests that the loss or gain of function of Id proteins may lead to cellular transformation (Fong S, et al., Trends Mol Med 2004. 10(8): p. 387-92; Lasorella A, et al., Oncogene 2001. 20(58): p. 8326-33; Perk J, et al., Nat Rev Cancer 2005. 5(8): p. 603-14). For example, increased expression of Id1, which has been found overexpressed in over 20 types of cancer, is associated with tumor malignancy and highly aggressive cancer (for example see Zhao Z R, et al., Oncol Rep 2008. 19(2): p. 419-24). Id, particularly Id1, is involved in many processes associated with cancer such as overcoming cell senecence (Swarbrick A. et al., Proc Natl Acad Sci USA. 2008; 105(14): p. 5402-7; Cummings S D, et al., Mol Carcinog 2008. 47(9): p. 653-9), upregulation of pro-growth tyrosine receptor kinases (Tam W F, et al., Blood 2008. 112(5): p. 1981-92), immortalizing cells (Suh H C, et al., Oncogene. 2008. 27: p. 5612-5623), metastasis (Ling M T, et al., Differentiation. 2006. 74(9-10): p. 481-7, tumor-reinitiation post metastasis (Gupta G P, et al., Proc Natl Acad Sci USA 2007. 104(49): p. 19506-11), neovascularization (Lyden D, et al., Nature 1999. 401(6754): p. 670-7; de Candia P, et al., Proc Natl Acad Sci USA 2003. 100(21): p. 12337-42) and protection from apoptosis (Wong Y C, et al., Apoptosis 2004. 9(3): p. 279-89.

Particularly significant with respect to neovascularization is the role of Id1 in promoting formation of endothelial progenitor cells in the bone marrow (Ciarrocchi A., et al., PLoS ONE 2007. 2(12): p. e1338; Li H, et al., Cancer Res 2004. 64(17): p. 6137-43; Lyden D, et al., Nat Med 2001. 7(11): p. 1194-201; Ruzinova M B, et al., Cancer Cell 2003. 4(4): p. 277-89). These cells are believed to be controlling element in the neovascularization process (Gao D, et al., Science 2008. 319(5860): p. 195-8) needed to provide nutrients and oxygen to tumors.

Increased expression of Id1 (Ouyang, X. S., et al., J Urol 2002; 167: 2598-602; Ouyang, X. S., et al., Carcinogenesis 2002; 23: 721-5) and Id2 is associated with tumor malignancy and highly aggressive prostate cancer (Coppe, J. P., et al., Clin Cancer Res 2004; 10: 2044-51). Expression of Id-1 also leads to activation of two important growth promoters, EGF-R and NFκB, in prostate cancer cells ultimately leading to progression to androgen independence (Ling M T, Wang X, Lee D T, Tam P C, Tsao S W, and Wong Y C). Carcinogenesis 2004; 25: 517-25) Constitutive expression of Id1, and to a lesser extend Id2, has also been reported to convert non-aggressive LNCaP prostate cancer cells into more proliferative and invasive cells with increased secretion of matrix metalloproteinases.

Over-expression of Id-1 was also found to induce expression of MT1-MMP protein leading to invasion of breast cancer cells (Fong S, Itahana Y, Sumida T, Singh J, Coppe J P, Liu Y, Richards P C, Bennington J L, Lee N M, Debs R J, Desprez P Y. Proc Natl Acad Sci USA 2003; 100: 13543-8. The fact that Id-1 is able to activate multiple pathways involved in tumor progression suggests that Id-1 may in addition function in the promotion of tumor development. Expression of Id-1 and Id-3 also promotes metastasis. Inhibition of Id-1 and Id-3 inhibits peritoneal metastasis of gastric cancer (PMID 16271072).

The specific mechanisms or pathways that lead to Id mediated malignant transformation may include regulation of genes for example, BRCA1 by Id-4 (Beger, C., et al., Proc Natl Acad Sci USA 2001. 98: 130-5) and p16 and p21 by Id1 (Alani, R. M., A. Z. Young, and C. B. Shifflett, Proc Natl Acad Sci USA 2001; 98: 7812-6) at the promoter level and modulation of retinoblastoma (Rb) activity by Id2 through direct physical interactions (Iavarone, A., et al., Genes Dev 1994; 8: 1270-84; Lasorella, A., et al., Cancer Res 2002; 62: 301-6). Additionally, Id-1 can up regulate the RAF-1/MAPK and down-regulate JNK signaling pathways leading to loss of the sensitivity of cancer cells to Taxol, a commonly used chemotherapeutic agent (Zhang X, Ling M T, Wang X, Wong Y C. Int J Cancer 2006; 118: 2072-81; Cheung H W, Ling M T, Tsao S W, Wong Y C, Wang X. Carcinogenesis 2004; 25: 881-7.)

Anti-Id (apoptosis inducing, cellular proliferation inhibiting, chemotherapeutic enhancing, transcription regulating, anti-inflammatory, cellular differentiation promoting, cellular transformation modulating, cell migration and metastasis modulating) compositions of the present invention which do not inhibit Id binding partners were identified using three dimensional E47-Id1 interaction mapping and cellular assays. An Id1 binding site was determined and virtual screening against the solution Id1 structure performed. 1.1 million compounds were screened using Monte Carlo simulation for the complex of Id1 and the small compound of interest. The total number of screened compounds was narrowed down to 3000 candidates which were further analyzed for particular ClogP, tPSA, molecular weights and chemical and biochemical stability as explained in the examples below. Of the 3000 compounds, 364 were identified which are useful in the compositions and methods herein. Additionally twelve peptides were constructed using the E47 molecule from the X-ray structure of the E47-Id1 heterodimer as a template. The designed peptides were deemed to have significant probability of retaining an α-helical conformation in solution.

Exemplary embodiments of identified anti-Id compositions include the compounds of Formulas I and III, and those compositions identified in Formulas II and IV and derivatives thereof as well as other pharmaceutically acceptable active salts of said compounds, as well as active isomers, enantiomers, polymorphs, solvates, hydrates, and/or prodrugs of said compounds.

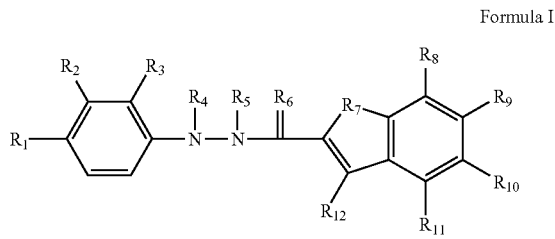

Formula I wherein $R_1$ may be a substituted or unsubstituted lower hydrocarbon independently selected from the group consisting of alkyl, alkenyl, alkanoyl, alkynyl, aryl, aroyl, aralkyl, alkylamino, aryloxy, hydrogen, carboxyl, nitro, thioalkoxy, thioaryloxy, thiol, cycloalkenyl cycloalkyl, heterocycloalkyl, heteroaryl, aralkyl, amino acid, peptide, dye, fluorophore, carbohydrate or polypeptide; $R_2$ and $R_3$ may independently, collectively, or in any combination that yields an active anti-Id (apoptosis inducing, cellular proliferation inhibiting, chemotherapeutic enhancing, transcription regulating, anti-inflammatory, cellular differentiation promoting, cellular transformation modulating, cell migration and metastasis modulating) compound be selected from the group consisting of hydrogen, hydroxyl, sulfyhydryl, fluorine, methyl, ethyl, propyl, benzyl, 2-bromovinyl amino, hydroxymethyl, methoxy, halogen, pseudohalogen, cyano, carboxyl, nitro, thioalkoxy, thioaryloxy, thiol, substituted or unsubstituted lower hydrocarbons containing 1 to 20 carbons, alkoxycarbonyl, alkoxycarbonylamino, amino, amino acid, aminocarbonyl, aminocarbonyloxy, aralkyl, aryloxy, carboxyl, cycloalkenyl, alkyl, cycloalkyl, heterocycloalkyl, aryl, heteroaryl, aralkyl, amino acid, peptide, dye, fluorophore, carbohydrate or polypeptide; $R_4$ and $R_5$ may independently, collectively, or in any combination that yields an active anti-Id (apoptosis inducing, cellular proliferation inhibiting, chemotherapeutic enhancing, transcription regulating, anti-inflammatory, cellular differentiation promoting, cellular transformation modulating) compound be an acyl or a substituted or unsubstituted lower hydrocarbon independently selected from the group consisting of alkyl, alkenyl, alkanoyl, aryl, aroyl, aralkyl or alkylamino; $R_6$ may be independently selected from oxygen or another heteroatom such as sulfur or nitrogen; $R_7$ may be sulfur or another heteroatom such as nitrogen or oxygen as well as a carbon; $R_8$, $R_9$, $R_{10}$, $R_{11}$, and $R_{12}$ may independently, collectively, or in any combination that yields an active anti-Id (apoptosis inducing, cellular proliferation inhibiting, chemotherapeutic enhancing, transcription regulating, anti-inflammatory, cellular differentiation promoting, cellular transformation modulating) compound be selected from the group consisting of hydrogen, hydroxyl, sulfyhydryl, fluorine, methyl, ethyl, propyl, benzyl, 2-bromovinyl amino, hydroxymethyl, methoxy, halogen, pseudohalogen, cyano and a substituted or unsubstituted lower hydrocarbon containing 1 to 20 carbons.

When more than one R group is present, the R group may be selected from any of the stated groups so as to be the same or different. In additional embodiments, two or more R groups may be joined together. In some embodiments, $R_2$ and $R_3$ may be members of a 5 or 6 member exocyclic ring structure; and/or $R_3$ and $R_4$ may be members of a 5 or 6 member exocyclic ring structure. In other embodiments, $R_5$ and $R_6$ may be members of a 5 or 6 member exocyclic ring structure. In additional embodiments, $R_{11}$ and $R_{12}$ may be members of a 5 or 6 member exocyclic ring structure. In further embodiments, if $R_7$ is nitrogen, $R_6$ and $R_7$ may be members of a 5 or 6 member exocyclic ring structure. In yet another embodiment, $R_6$ and $R_{12}$ may be members of a 5 or 6 member exocyclic ring structure.

In exemplary embodiments, the anti-Id compound of Formula I may be N'-(4-isopropylphenyl)-1-benzothiophene-2-carbohydrazide as shown in Formula II and derivatives thereof.

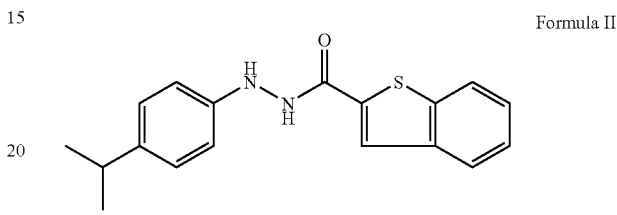

Formula II

In another embodiment, anti-Id compounds of the present invention may have the structure of Formula III, below:

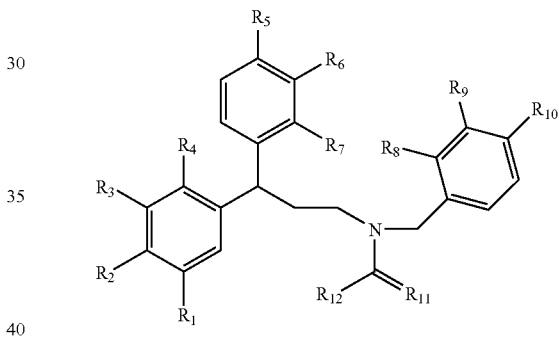

wherein, $R_1$, $R_2$, $R_3$, $R_4$, $R_5$, $R_6$, $R_8$, $R_9$, and $R_{10}$. may independently, collectively, or in any combination that yields an active anti-Id (apoptosis inducing, cellular proliferation inhibiting, chemotherapeutic enhancing, transcription regulating, anti-inflammatory, cellular differentiation promoting, cellular transformation modulating) compound be selected from the group consisting of hydrogen, hydroxyl, sulfyhydryl, fluorine, methyl, ethyl, propyl, benzyl, 2-bromovinyl amino, hydroxymethyl, methoxy, halogen, pseudohalogen, cyano, carboxyl, nitro, thioalkoxy, thioaryloxy, thiol, substituted or unsubstituted lower hydrocarbon containing 1 to 20 carbons, alkoxycarbonyl, alkoxycarbonylamino, amino, amino acid, aminocarbonyl, aminocarbonyloxy, aralkyl, aryloxy, carboxyl, cycloalkenyl, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, amino acid, peptide, dye, fluorophore, carbohydrate or polypeptide; $R_7$ may be hydrogen, hydroxyl, benzoyl; substituted benzoyl or hydroxyl substituted with unsubstituted lower hydrocarbon containing 1 to 20 carbons; $R_{11}$ may be oxygen, or another heteroatom such as sulfur or nitrogen; and $R_{12}$ may be a substituted or unsubstituted lower hydrocarbon independently selected from the group consisting of alkyl, alkenyl, alkanoyl, alkynyl, aryl, aroyl, aralkyl, alkylamino, aryloxy, hydrogen, carboxyl, nitro, thioalkoxy, thioaryloxy, thiol, cycloalkenyl substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, amino acid, peptide, dye, fluorophore, carbohydrate or polypeptide.

One having ordinary skill in the art will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

When more than one R group is present, the R group may be selected from any of the stated groups so as to be the same or different. In additional embodiments, two or more R groups may be joined together. For example, in some embodiments, $R_4$ may become members of a 5 or 6 member ring structure with neighboring rings.

In exemplary embodiments, the anti-Id composition of Formula III may be N-[3-(1,3-benzodioxol-5-yl)-3-(2-methoxyphenyl)propyl]-N-benzylpropanamide and derivatives thereof as shown in Formula IV, below.

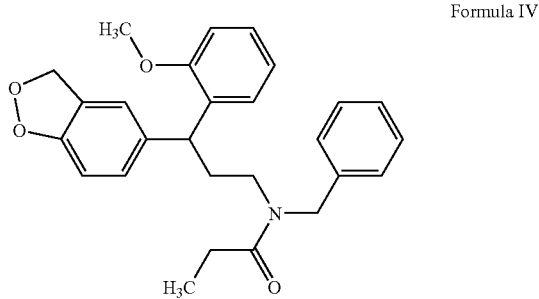

Formula IV

In some embodiments, N-[3-(1,3-benzodioxol-5-yl)-3-(2-methoxyphenyl)propyl]-N-benzylpropanamide may be part of a racemic mixture. This mixture can be resolved using standard methods and either enantiomer used as a therapeutic. The addition of another asymmetric center in the molecule would introduce the possibility of diastereomers. Useful anti-Id related compounds and derivatives of Formulas I, II, III and IV within the formulations and methods herein include, but are not limited to, other pharmaceutically acceptable active salts of said compounds, as well as active isomers, enantiomers, polymorphs, solvates, hydrates, and/or prodrugs of said compounds.

"Stereoisomer" as it relates to a given compound is well understood in the art, and refers to another compound having the same molecular formula, wherein the atoms making up the other compound differ in the way they are oriented in space, but wherein the atoms in the other compound are like the atoms in the given compound with respect to which atoms are joined to which other atoms (e.g. an enantiomer, a diastereomer, or a geometric isomer). See for example, Morrison and Boyd, Organic Chemistry, 1983, 4th ed., Allyn and Bacon, Inc., Boston, Mass., p. 123.

"Substituted" as used herein refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$. Typical substituents include, but are not limited to, —X, —O—, =O, —OR$_8$, —SR$_8$, —S—, =S, —NR$_8$R$_9$, =NR$_8$, —CX$_3$, —CF$_3$, —CN, —OCN, —SCN, —NO, —NO$_2$, =N$_2$, —N$_3$, —S(O)$_2$O—, —S(O)$_2$OH, —S(O)$_2$R$_8$, —OS(O$_2$)O—, —OS(O)$_2$R$_8$, —P(O)(O—)$_2$, —P(O)(OR$_8$)(O—), —OP(O)(OR$_8$)(OR$_9$), —C(O)R$_8$, —C(S)R$_8$, —C(O)OR$_8$, —C(O)NR$_8$R$_9$, —C(O)O—, —C(S)OR$_8$, —NR$_{10}$C(O)NR$_8$R$_9$, —NR$_{10}$C(S)NR$_8$R$_9$, —NR$_{11}$C(NR$_{10}$)NR$_8$R$_9$ and —C(NR$_{10}$)NR$_8$R$_9$, where each X is independently a halogen.

"Acyl" as used herein refers to a radical —C(O)R, where R is hydrogen, alkyl, cycloalkyl, heterocycloalkyl, aryl, arylalkyl, heteroalkyl, or heteroaryl as defined herein. Representative examples include, but are not limited to, formyl, acetyl, cylcohexylcarbonyl, cyclohexylmethylcarbonyl, benzoyl, benzylcarbonyl and the like.

"Acylamino" as used herein refers to a radical —NR'C(O)R, where R' is hydrogen, alkyl, cycloalkyl, heterocycloalkyl, aryl, arylalkyl, heteroalkyl, heteroaryl, heteroarylalkyl and R is hydrogen, alkyl, alkoxy, cycloalkyl, heterocycloalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" as used herein refers to the group —OC(O)H, —OC(O)-alkyl, —OC(O)-aryl or —OC(O)— cycloalkyl.

"Aliphatic" as used herein refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkynyl and alkynylene. Aliphatic groups typically have from 1 or 2 to 6 or 12 carbon atoms.

"Alkenyl" as used herein refers to monovalent olefinically unsaturated hydrocarbyl groups having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH2), n-propenyl (—CH2CH=CH2), isopropenyl (—C(CH3)=CH2), vinyl and substituted vinyl, and the like.

"Alkoxy" as used herein refers to the group —O-alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" as used herein refers to a radical —C(O)-alkoxy where alkoxy is as defined herein. "Alkoxycarbonylamino" refers to the group —NRC(O)OR' where R is hydrogen, alkyl, aryl or cycloalkyl, and R' is alkyl or cycloalkyl.

"Alkyl" as used herein refers to monovalent saturated aliphatic hydrocarbyl groups particularly having up to about 12 or 18 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "alkyl" also includes "cycloalkyls" as defined herein.

"Alkylene" as used herein refers to divalent saturated aliphatic hydrocarbyl groups particularly having up to about 12 or 18 carbon atoms and more particularly 1 to 6 carbon atoms which can be straight-chained or branched. This term is exemplified by groups such as methylene (—CH2-), ethylene (—CH2CH2-), the propylene isomers (e.g., —CH2CH2CH2- and —CH(CH3)CH2-) and the like.

"Alkynyl" as used herein refers to acetylenically unsaturated hydrocarbyl groups particularly having up to about 12 or 18 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH2C≡CH), and the like.

The terms "alkanoyl" and "alkanoyloxy" as used herein refer, respectively, to —C(O)-alkyl groups and —O—C(O)-alkyl groups, each optionally containing 2-5 carbon atoms. Specific embodiments of alkanoyl and alkanoyloxy groups are acetyl and acetoxy, respectively.

"Amino" as used herein refers to the radical —NH2.

"Amino acid" as used herein refers to any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine).

"Substituted amino" as used herein includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group.

"Aminocarbonyl" as used herein refers to the group —C(O)NRR where each R is independently hydrogen, alkyl, aryl or cycloalkyl, or where the R groups are joined to form an alkylene group.

"Aminocarbonylamino" as used herein refers to the group —NRC(O)NRR where each R is independently hydrogen, alkyl, aryl or cycloalkyl, or where two R groups are joined to form an alkylene group.

"Aminocarbonyloxy" as used herein refers to the group —OC(O)NRR where each R is independently hydrogen, alkyl, aryl or cycloalkyl, or where the R groups are joined to form an alkylene group. "Amino-containing saccharide group" refers to a saccharide group having an amino substituent. Representative amino-containing saccharide includes L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like.

"Aralkyl" or "arylalkyl" as used herein refers to an alkyl group, as defined above, substituted with one or more aryl groups, as defined above.

"Aryl" as used herein refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Aryloxy" as used herein refers to —O-aryl groups wherein "aryl" is as defined herein.

The term "aroyl," as used alone or in combination herein, refers to an aryl radical derived from an aromatic carboxylic acid, such as optionally substituted benzoic or naphthoic acids.

"Alkylamino" as user herein refers to a lower alkyl radical appended to an NH radical.

"Azido" as used herein refers to the radical —N3.

"Carbohydrate" as used herein means a mono-, di-, tri-, or polysaccharide, wherein the polysaccharide can have a molecular weight of up to about 20,000, for example, hydroxypropyl-methylcellulose or chitosan.

"Carboxyl" refers to the radical —C(O)OH.

"Cyano" as used herein refers to the radical —CN.

"Cycloalkenyl" as used herein refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Cycloalkyl" as used herein refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Heterocycloalkyl" as used herein refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl.

"Halo" or "halogen" as used herein refers to fluoro, chloro, bromo and iodo. Halo groups can be either fluoro or chloro.

"Hetero" as used herein to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, cycloheteroalkenyl, and the like having from 1 to 5, and particularly from 1 to 3 heteroatoms.

"Heteroaryl" as used herein refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. The heteroaryl group can be a 5-20 membered heteroaryl, or 5-10 membered heteroaryl. Particular heteroaryl groups are those derived from thiophene, pyrrole, benzothiophene, benzofuran, indole, pyridine, quinoline, imidazole, oxazole and pyrazine.

"Hydroxyl" as used herein refers to the radical —OH.

"Hydroxymethyl" as used herein refers to a lower alkyl of one to ten carbon atoms substituted at one or more carbon atoms with a hydroxy group.

"Methoxy" as used herein refers to methoxy refers to the group —O—CH3.

"Nitro" as used herein refers to the radical —$NO_2$.

"Pseudohalogen" as used herein is a binary inorganic compounds of the general form XY, where X is a cyanide, cyanate, thiocyanate group and Y is any of X, or a true halogen.

"Benzyl" as used therein is the radical $C_6H_5CH_2$.

"Thioalkoxy" as used herein refers to the group —S-alkyl.

"Thioaryloxy" as used herein refers to the group —S-aryl.

"Thioketo" as used herein refers to the group =S.

"Thiol" or "sulfhydryl" as used herein refers to the group —SH.

Anti-Id (apoptosis inducing, cellular proliferation inhibiting, chemotherapeutic enhancing, transcription regulating, anti-inflammatory, cellular differentiation promoting, cellular transformation modulating, cell migration and metastasis modulating) compositions comprising compounds of Formula I and/or III, particularly compounds of Formula II and/or IV and derivatives thereof, including pharmaceutical formulations of the invention, comprise an anti-Id effective amount of a compound, which is effective for prophylaxis and/or treatment of cellular proliferative diseases in a mammalian subject. Typically, an anti-Id (apoptosis inducing, cellular proliferation inhibiting, chemotherapeutic enhancing, transcription regulating, anti-inflammatory, cellular differentiation promoting, cellular transformation modulating, cell migration and metastasis modulating) effective amount of a compound will comprise an amount of the active compound which is therapeutically effective, in a single or multiple unit dosage form, over a specified period of therapeutic intervention, to measurably alleviate one or more symptoms of cellular proliferative disorders or other Id conditions in the subject, and/or to alleviate one or more symptom(s) of cellular proliferative disease or condition in the subject.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "treatment" or "treating" means any treatment of a disease or disorder, including preventing or protecting against the disease or disorder (that is, causing the clinical symptoms not to develop); inhibiting the disease or disorder (i.e., arresting or suppressing the development of clinical symptoms; and/or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing". The term "protection" thus includes "prophylaxis." Within exemplary embodiments, these compositions are effective within in vivo treatment methods to alleviate cellular proliferative diseases.

Anti-Id (apoptosis inducing, cellular proliferation inhibiting, chemotherapeutic enhancing, transcription regulating, anti-inflammatory, cellular differentiation promoting, cellular transformation modulating, cell migration and metastasis modulating) compositions of the invention typically comprise an anti-cellular proliferative effective amount or unit dosage of a compound of Formula I and/or III, which may be formulated with one or more pharmaceutically acceptable carriers, excipients, vehicles, emulsifiers, stabilizers, preservatives, buffers, and/or other additives that may enhance stability, delivery, absorption, half-life, efficacy, pharmacokinetics, and/or pharmacodynamics, reduce adverse side effects, or provide other advantages for pharmaceutical use. Anti-Id effective amounts including anti-cellular proliferative effective amounts (apoptosis inducing, cellular proliferation inhibiting, chemotherapeutic enhancing, transcription regulating, anti-inflammatory, cellular differentiation promoting, cellular transformation modulating, cell migration and metastasis modulating) of a compound of Formula I and/or III or related or derivative compound (e.g., a unit dose comprising an effective concentration/amount of compound of Formula I and/or III, or of a selected pharmaceutically acceptable salt, isomer, enantiomer, solvate, polymorph and/or prodrug of a compound of Formula I and/or III) will be readily determined by those of ordinary skill in the art, depending on clinical and patient-specific factors. Suitable effective unit dosage amounts of the active compounds for administration to mammalian subjects, including humans, may range from 10 to 1500 mg, 20 to 1000 mg, 25 to 750 mg, 50 to 500 mg, or 150 to 500 mg. In certain embodiments, the anti-Id effective dosage of a composition of Formula I and/or III may be selected within narrower ranges of, for example, 10 to 25 mg, 30-50 mg, 75 to 100 mg, 100 to 250 mg, or 250 to 500 mg. These and other effective unit dosage amounts may be administered in a single dose, or in the form of multiple daily, weekly or monthly doses, for example in a dosing regimen comprising from 1 to 5, or 2-3, doses administered per day, per week, or per month. In one exemplary embodiment, dosages of 10 to 25 mg, 30-50 mg, 75 to 100 mg, 100 to 250 mg, or 250 to 500 mg, are administered one, two, three, four, or five times per day. In more detailed embodiments, dosages of 50-75 mg, 100-200 mg, 250-400 mg, or 400-600 mg are administered once or twice daily. In alternate embodiments, dosages are calculated based on body weight, and may be administered, for example, in amounts from about 0.5 mg/kg to about 100 mg/kg per day, 1 mg/kg to about 75 mg/kg per day, 1 mg/kg to about 50 mg/kg per day, 2 mg/kg to about 50 mg/kg per day, 2 mg/kg to about 30 mg/kg per day or 3 mg/kg to about 30 mg/kg per day.

The amount, timing and mode of delivery of compositions of the invention comprising an anti-Id effective amount of a compound of Formula I and/or III will be routinely adjusted on an individual basis, depending on such factors as weight, age, gender, and condition of the individual, the acuteness of the cellular proliferative disorder and/or related symptoms, whether the administration is prophylactic or therapeutic, and on the basis of other factors known to effect drug delivery, absorption, pharmacokinetics, including half-life, and efficacy.

An effective dose or multi-dose treatment regimen for the instant anti-Id (apoptosis inducing, cellular proliferation inhibiting, chemotherapeutic enhancing, transcription regulating, anti-inflammatory, cellular differentiation promoting, cellular transformation modulating) formulations will ordinarily be selected to approximate a minimal dosing regimen that is necessary and sufficient to substantially prevent or alleviate cellular proliferative disorders and diseases in the subject, and/or to substantially prevent or alleviate one or more symptoms associated with cellular proliferative disorders in the subject. A dosage and administration protocol will often include repeated dosing therapy over a course of several days or even one or more weeks or years. An effective treatment regime may also involve prophylactic dosage administered on a day or multi-dose per day basis lasting over the course of days, weeks, months or even years.

Various assays and model systems can be readily employed to determine the therapeutic effectiveness of a compound of Formula I and/or III including the identification and counting of cellular proliferative cell markers or other indicators such as circulating endothelial cells, circulating progenitor endothelial cells, circulating tumor cells, and mRNA levels and measurements of tumor markers such as, but not limited to, PSA or monoclonal protein. Additionally effectiveness may be determined by visual inspection, such as through a decrease in the size of a neoplasm.

Effectiveness of the compositions and methods of the invention may be demonstrated by a decrease in the symptoms of cellular proliferative disorders including a decrease in cellular proliferation, a decrease in inflammation, or any other symptom associated with cellular proliferative disorders. Such a decrease may be a decrease of 5%, 10%, 25%, 30%, 50%, 75%, 90% or more.

Effectiveness of the treatment may be monitored by counting circulating endothelial cells. Circulating endothelial cells are generally absent in the blood of healthy individuals and elevated in individuals suffering from diseases hallmarked by the presence of vascular insult such as cancer. The number of circulating endothelial cells may be determined by any means applicable such as through flow cytometry, immunobead capture, fluorescence microscopy, standard and density centrifugation, or mononuclear cell culturing on fibronectin-coated plates and immunocytochemistry. An effective amount of the compound of Formulas I and III would decrease the number of circulating endothelial cells by 5%, 10%, 25%, 30%, 50%, 75%, 90% or more.

Effectiveness of the treatment may additionally be monitored by counting circulating endothelial progenitor cells. Malignant transformation is associated with increased numbers of circulating endothelial progenitor cells. Effective amounts of the compositions of the present invention would decrease the number of circulating endothelial progenitor cells. Such cells may be counted by any means applicable such as through flow cytometry, immunobead capture, fluorescence microscopy, standard and density centrifugation, or mononuclear cell culturing on fibronectin-coated plates and immunocytochemistry. An effective amount of the compound of Formulas I and III would decrease the number of circulating endothelial progenitor cells by 5%, 10%, 25%, 30%, 50%, 75%, 90% or more.

Effectiveness of the treatment may further be monitored by imaging such as x-rays or MRIs to determine if the size of a tumor has decreased. Effectiveness may additionally be determined by visual observation of a decrease in tumor size. Effective amounts of compositions containing a compound of Formula I and III would lead to a 5%, 10%, 25%, 30%, 50%, 75%, 90% or greater reduction of tumor size.

Effectiveness may further be determined by measuring the number of circulating tumor cells in a sample of blood. Measurement of the number of circulating tumor cells may take place using any means applicable including, but not limited to immunomagnetic selection, flow cytometry, immunobead capture, fluorescence microscopy, cytomorphologic analysis, or cell separation technology. Levels of circulating tumor cells in a sample of blood will decrease when an effective amount of a compound of Formula I and III is administered.

Effectiveness may additionally be determined by analyzing blood samples to determine the amount of mRNA expressed in tumor cells using RT-PCR. Effective amounts of the compounds of Formula I and III would decrease the amount of mRNA expressed in tumor cells.

Effectiveness may also be determined by measuring the tumor cells in other tissues/organs including but not limited to bone, lymph nodes and lung. Levels of tumor cells will decrease when an effective amount of a compound of Formula I and III is administered.

For each of the indicated conditions described herein, test subjects will exhibit a 10%, 20%, 30%, 50% or greater reduction, up to a 75-90%, or 95% or greater, reduction, in one or more symptom(s) caused by, or associated with, a cellular proliferative disease or condition in the subject, compared to placebo-treated or other suitable control subjects.

Within additional aspects of the invention, combinatorial cellular proliferative disease treating formulations and coordinate administration methods are provided which employ an effective amount of a compound of Formula I and/or Formula III and one or more secondary or adjunctive agent(s) that is/are combinatorially formulated or coordinately administered with a compound of Formula I and/or Formula III to yield a combined, multi-active agent anti-Id (apoptosis inducing, cellular proliferation inhibiting, chemotherapeutic enhancing, transcription regulating, anti-inflammatory, cellular differentiation promoting, cellular transformation modulating, cell migration and metastasis modulating) composition or coordinate treatment method. Exemplary combinatorial formulations and coordinate treatment methods in this context employ the compound of Formula I and/or Formula III in combination with the one or more secondary anti-cellular proliferative (apoptosis inducing, chemotherapeutic enhancing, transcription regulating, anti-inflammatory, cellular differentiation promoting, cellular transformation modulating, cell migration and metastasis modulating) agent(s), or with one or more adjunctive therapeutic agent(s) including other chemotherapeutic or toxicity reducing agents that is/are useful for treatment or prophylaxis of the targeted (or associated) disease, condition and/or symptom(s) in the selected combinatorial formulation or coordinate treatment regimen. For most combinatorial formulations and coordinate treatment methods of the invention, a compound of Formula I and/or Formula III and/or related or derivative compound is formulated, or coordinately administered, in combination with one or more secondary or adjunctive therapeutic agent(s), to yield a combined formulation or coordinate treatment method that is combinatorially effective or coordinately useful to treat cellular proliferative disorders and/or one or more symptom(s) of a cellular proliferative disease or condition in the subject. Exemplary combinatorial formulations and coordinate treatment methods in this context employ a compound of Formula I and/or Formula III in combination with one or more secondary or adjunctive therapeutic agents selected from, e.g., anti-cancer and other anti-hyperproliferative agents including chemotherapeutic agents such as, but not limited to, DNA damaging agents and agents that inhibit DNA synthesis including, but not limited to, anthracyclines including doxorubicin, daunorubicin, epirubicin, alkylating agents including bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine, platinum derivatives including cisplatin, carboplatin, cis diamminedichloroplatinum, and telomerase and topoisomerase inhibitors; tubulin-depolymerizing agents including, but not limited to, taxoids such as paclitaxel, docetaxel, BAY 59-8862; anti-metabolites including, but not limited to, capecitabine, chlorodeoxyadenosine, cytarabine (and its activated form, ara-CMP), cytosine arabinoside, dacabazine, floxuridine, fludarabine, 5-fluorouracil, 5-DFUR, gemcitabine, hydroxyurea, 6-mercaptopurine, methotrexate, pentostatin, trimetrexate, and 6-thioguanine; anti-angiogenics including, but not limited to, Avastin, thalidomide, sunitinib, lenalidomide; vascular disrupting agents including, but not limited to, flavonoids/flavones, DMXAA, combretastatin derivatives such as CA4DP, ZD6126, AVE8062A; biologics such as antibodies including, but not limited to, Herceptin, Avastin, Panorex, Rituxin, Zevalin, Mylotarg, Campath, Bexxar, Erbitux; endocrine therapy including, but not limited to, aromatase inhibitors such as 4-hydroandrostendione, exemestane, aminoglutehimide, anastrzole, letozole, anti-estrogens such as Tamoxifen, Toremifine, Raoxifene, Faslodex, and steroids such as dexamethasone; immuno-modulators including, but not limited to, cytokines such as IFN-beta and IL2, inhibitors to integrins, other adhesion proteins and matrix metalloproteinases; histone deacetylase inhibitors; inhibitors of signal transduction such as inhibitors of tyrosine kinases like imatinib; inhibitors of heat shock proteins; retinoids such as all trans retinoic acid; inhibitors of growth factor receptors or the growth factors themselves; anti-mitotic compounds such as navelbine, paclitaxel, taxotere, vinblastine, vincristine, vindesine, and vinorelbine; anti-inflammatories such as COX inhibitors; and cell cycle regulators such as check point regulators and telomerase inhibitors. Additional adjunctive therapies include, but are not limited to, radiation therapy, surgery, gene therapy, DNA vaccines and therapy, siRNA therapy, anti-angiogenic therapy, immunotherapy, bone marrow transplants, apatamers and other biologics such as antibodies and antibody variants, receptor decoys and other protein-based and non-protein based therapeutics.

In certain embodiments the invention provides combinatorial anti-Id (apoptosis inducing, cellular proliferation inhibiting, chemotherapeutic enhancing, transcription regulating, anti-inflammatory, cellular differentiation promoting, cellular transformation modulating, cell migration and metastasis modulating) formulations comprising a composition of Formula I and/or III and one or more adjunctive agent(s) having anti-cellular proliferative (anti-angiogenic, apoptosis inducing, chemotherapeutic sensitivity increasing) activity. Within such combinatorial formulations, compounds of Formula I and/or III and the adjunctive agent(s) having anti-Id (apoptosis inducing, cellular proliferation inhibiting, chemotherapeutic enhancing, transcription regulating, anti-inflammatory, cellular differentiation promoting, cellular transformation modulating) activity will be present in a combined formulation in anti-Id effective amounts, alone or in combination. In exemplary embodiments, compounds of Formula I and/or III and another agent(s) will each be present in cellular proliferative disorder treating amount (i.e., in singular dosage which will alone elicit a detectable anti-cellular proliferative response in the subject). Alternatively, the combinatorial formulation may comprise one or both of the anti-Id compound and non-anti Id agents in sub-therapeutic singular dosage amount(s), wherein the combinatorial formulation comprising both agents features a combined dosage of both agents that is collectively effective in eliciting an anti-cellular proliferative response. Thus, one or both of the anti-Id compound and non-anti Id agents may be present in the formulation, or administered in a coordinate administration protocol, at a sub-therapeutic dose, but collectively in the formulation or method they elicit a detectable anti-cellular proliferative disorder response in the subject.

To practice coordinate administration methods of the invention, a compound of Formula I and/or III may be administered, simultaneously or sequentially, in a coordinate treatment protocol with one or more of the secondary or adjunctive therapeutic agents contemplated herein. Thus, in certain embodiments a compound is administered coordinately with a non-anti-Id agent, or any other secondary or adjunctive therapeutic agent contemplated herein, using separate formulations or a combinatorial formulation as described above (i.e., comprising both a compound of Formula I and/or III or related or derivative compound, and a non-anti-Id therapeutic agent). This coordinate administration may be done simultaneously or sequentially in either order, and there may be a time period while only one or both (or all) active therapeutic agents individually and/or collectively exert their biological activities. A distinguishing aspect of all such coordinate treatment methods is that the anti-Id compound exerts at least some anti-cellular proliferative activity, which yields a favorable clinical response in conjunction with a complementary anti-cellular proliferative, or distinct, clinical response provided by the secondary or adjunctive therapeutic agent. Often, the coordinate administration of the anti-Id compound with the secondary or adjunctive therapeutic agent will yield improved therapeutic or prophylactic results in the subject beyond a therapeutic effect elicited by the anti-Id compound, or the secondary or adjunctive therapeutic agent administered alone. This qualification contemplates both direct effects, as well as indirect effects.

Within exemplary embodiments, an anti-Id (apoptosis inducing, cellular proliferation inhibiting, chemotherapeutic enhancing, transcription regulating, anti-inflammatory, cellular differentiation promoting, cellular transformation modulating, cell migration and metastasis modulating) compound will be coordinately administered (simultaneously or sequentially, in combined or separate formulation(s)), with one or more secondary anti-cellular proliferative agents, or other indicated therapeutic agents including toxicity reducing agents, e.g., selected from, for example, anti-cancer and other anti-hyperproliferative agents including chemotherapeutic agents such as, but not limited to, DNA damaging agents and agents that inhibit DNA synthesis including, but not limited to, anthracyclines including doxorubicin, daunorubicin, epirubicin, alkylating agents including bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine, platinum derivatives including cisplatin, carboplatin, cis diamminedichloroplatinum, and telomerase and topoisomerase inhibitors; tubulin-depolymerizing agents including, but not limited to, taxoids such as paclitaxel, docetaxel, BAY 59-8862; anti-metabolites including, but not limited to, capecitabine, chlorodeoxyadenosine, cytarabine (and its activated form, ara-CMP), cytosine arabinoside, dacabazine, floxuridine, fludarabine, 5-fluorouracil, 5-DFUR, gemcitabine, hydroxyurea, 6-mercaptopurine, methotrexate, pentostatin, trimetrexate, and 6-thioguanine;

anti-angiogenics including, but not limited to, Avastin, thalidomide, sunitinib, lenalidomide; vascular disrupting agents including, but not limited to, flavonoids/flavones, DMXAA, combretastatin derivatives such as CA4DP, ZD6126, AVE8062A; biologics such as antibodies including, but not limited to, Herceptin, Avastin, Panorex, Rituxin, Zevalin, Mylotarg, Campath, Bexxar, Erbitux; endocrine therapy including, but not limited to: aromatase inhibitors such as 4-hydroandrostendione, exemestane, aminoglutehimide, anastrzole, letozole, anti-estrogens such as Tamoxifen, Toremifine, Raoxifene, Faslodex, and steroids such as dexamethasone; immuno-modulators including, but not limited to, cytokines such as IFN-beta and IL2, inhibitors to integrins, other adhesion proteins and matrix metalloproteinases; histone deacetylase inhibitors; inhibitors of signal transduction such as inhibitors of tyrosine kinases like imatinib; inhibitors of heat shock proteins; retinoids such as all trans retinoic acid; inhibitors of growth factor receptors or the growth factors themselves; anti-mitotic compounds such as navelbine, paclitaxel, taxotere, vinblastine, vincristine, vindesine, and vinorelbine; anti-inflammatories such as COX inhibitors; and cell cycle regulators such as check point regulators and telomerase inhibitors.

As noted above, in all of the various embodiments of the invention contemplated herein, the anti-Id methods and formulations may employ a compound of Formula I and/or Formula III in any of a variety of forms, including any one or combination of the subject compound's pharmaceutically acceptable salts, isomers, enantiomers, polymorphs, solvates, hydrates, and/or prodrugs. In exemplary embodiments of the invention, N'-(4-isopropylphenyl)-1-benzothiophene-2-carbohydrazide and/or N-[3-(1,3-benzodioxol-5-yl)-3-(2-methoxyphenyl)propyl]-N-benzylpropanamide is employed within the therapeutic formulations and methods for illustrative purposes.

The pharmaceutical compositions of the present invention may be administered by any means that achieve their intended therapeutic or prophylactic purpose. Suitable routes of administration for the compositions of the invention include, but are not limited to, oral, buccal, nasal, aerosol, topical, transdermal, mucosal, injectable, slow release, controlled release, iontophoresis, sonophoresis, and including all other conventional delivery routes, devices and methods. Injectable methods include, but are not limited to, intravenous, intramuscular, intraperitoneal, intraspinal, intrathecal, intracerebroventricular, intraarterial, subcutaneous and intranasal routes.

The compositions of the present invention may further include a pharmaceutically acceptable carrier appropriate for the particular mode of administration being employed. Dosage forms of the compositions of the present invention include excipients recognized in the art of pharmaceutical compounding as being suitable for the preparation of dosage units as discussed above.

Such excipients include, without intended limitation, binders, fillers, lubricants, emulsifiers, suspending agents, sweeteners, flavorings, preservatives, buffers, wetting agents, disintegrants, effervescent agents and other conventional excipients and additives. The pharmaceutical composition may additionally contain other pharmaceutically acceptable components, such a buffers, surfactants, antioxidants, viscosity modifying agents, preservatives and the like. Each of these components is well-known in the art. See, e.g., U.S. Pat. No. 5,985,310, the disclosure of which is herein incorporated by reference in its entirety. Other components suitable for use in the formulations of the present invention can be found in Remington's Pharmaceutical Sciences, Mace Publishing Company, Philadelphia, Pa., 17th ed. (1985). By way of illustration, the anti-Id (apoptosis inducing, cellular proliferation inhibiting, chemotherapeutic enhancing, transcription regulating, anti-inflammatory, cellular differentiation promoting, cellular transformation modulating) active agent can be admixed with conventional pharmaceutically acceptable carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1 to about 90% by weight of the active compound, and more generally from about 1 to about 30% by weight of the active compound.

If desired, the compositions of the invention can be administered in a controlled release form by use of a slow release carrier, such as a hydrophilic, slow release polymer. Exemplary controlled release agents in this context include, but are not limited to, hydroxypropyl methyl cellulose, having a viscosity in the range of about 100 cps to about 100,000 cps or other biocompatible matrices such as cholesterol.

Compositions of the invention will often be formulated and administered in an oral dosage form, optionally in combination with a carrier or other additive(s). Suitable carriers common to pharmaceutical formulation technology include, but are not limited to, microcrystalline cellulose, lactose, sucrose, fructose, glucose, dextrose, or other sugars, di-basic calcium phosphate, calcium sulfate, cellulose, methylcellulose, cellulose derivatives, kaolin, mannitol, lactitol, maltitol, xylitol, sorbitol, or other sugar alcohols, dry starch, dextrin, maltodextrin or other polysaccharides, inositol, or mixtures thereof. Exemplary unit oral dosage forms for use in this invention include tablets, which may be prepared by any conventional method of preparing pharmaceutical oral unit dosage forms can be utilized in preparing oral unit dosage forms. Oral unit dosage forms, such as tablets, may contain one or more conventional additional formulation ingredients, including, but not limited to, release modifying agents, glidants, compression aides, disintegrants, lubricants, binders, flavors, flavor enhancers, sweeteners and/or preservatives. Suitable lubricants include stearic acid, magnesium stearate, talc, calcium stearate, hydrogenated vegetable oils, sodium benzoate, leucine carbowax, magnesium lauryl sulfate, colloidal silicon dioxide and glyceryl monostearate. Suitable glidants include colloidal silica, fumed silicon dioxide, silica, talc, fumed silica, gypsum and glyceryl monostearate. Substances which may be used for coating include hydroxypropyl cellulose, titanium oxide, talc, sweeteners and colorants.

Additional compositions of the invention can be prepared and administered in any of a variety of inhalation or nasal delivery forms known in the art. Devices capable of depositing aerosolized purified anti-Id formulations in the sinus cavity or pulmonary alveoli of a patient include metered dose inhalers, nebulizers, dry powder generators, sprayers, and the like. Methods and compositions suitable for pulmonary delivery of drugs for systemic effect are well known in the art. Additional possible methods of delivery include deep lung delivery by inhalation. Suitable formulations, wherein the carrier is a liquid, for administration, as for example, a nasal spray or as nasal drops, may include aqueous or oily solutions of anti-Id compositions and any additional active or inactive ingredient(s).

Further compositions and methods of the invention provide for topical administration of an anti-Id compound for the treatment of cellular proliferative diseases. Topical compositions may comprise an anti-Id compound along with one or more additional active or inactive component(s) incorporated in a dermatological or mucosal acceptable carrier, including in the form of aerosol sprays, powders, dermal patches, sticks, granules, creams, pastes, gels, lotions, syrups, ointments, impregnated sponges, cotton applicators, or as a solution or suspension in an aqueous liquid, non-aqueous liquid, oil-in-water emulsion, or water-in-oil liquid emulsion. These topical compositions may comprise an anti-Id compound dissolved or dispersed in a portion of a water or other solvent or liquid to be incorporated in the topical composition or delivery device. It can be readily appreciated that the transdermal route of administration may be enhanced by the use of a dermal penetration enhancer known to those skilled in the art. Formulations suitable for such dosage forms incorporate excipients commonly utilized therein, particularly means, e.g. structure or matrix, for sustaining the absorption of the drug over an extended period of time, for example, 24 hours. Transdermal delivery may also be enhanced through techniques such as sonophoresis.

Additional compositions and methods of the invention provide for liquid compositions for use as anti-Id compounds in the treatment of cellular proliferative disorders. A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder. For example, a powder containing active compound, suspending agent, sucrose and a sweetener can be reconstituted with water to form a suspension; and syrup can be prepared from a powder containing active ingredient, sucrose and a sweetener.

Yet additional anti-Id compositions of the invention are designed for parenteral administration, e.g. to be administered intravenously, intramuscularly, subcutaneously or intraperitoneally, including aqueous and non-aqueous sterile injectable solutions which, like many other contemplated compositions of the invention, may optionally contain antioxidants, buffers, bacteriostats and/or solutes which render the formulation isotonic with the blood of the mammalian subject; and aqueous and non-aqueous sterile suspensions which may include suspending agents and/or thickening agents. The formulations may be presented in unit-dose or multi-dose containers. Additional compositions and formulations of the invention may include polymers for extended release following parenteral administration. The parenteral preparations may be solutions, dispersions or emulsions suitable for such administration. The subject agents may also be formulated into polymers for extended release following parenteral administration. Pharmaceutically acceptable formulations and ingredients will typically be sterile or readily sterilizable, biologically inert, and easily administered. Such polymeric materials are well known to those of ordinary skill in the pharmaceutical compounding arts. Parenteral preparations typically contain buffering agents and preservatives, and injectable fluids that are pharmaceutically and physiologically acceptable such as water, physiological saline, balanced salt solutions, aqueous dextrose, glycerol or the like. Extemporaneous injection solutions, emulsions and suspensions may be prepared from sterile powders, granules and tablets of the kind previously described. Preferred unit dosage formulations are those containing a daily dose or unit, daily sub-dose, as described herein above, or an appropriate fraction thereof, of the active ingredient(s).

A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetracetic acid, and an antioxidant, for example, sodium metabisulphite may be included in the formulation. Alternatively, the solution can be freeze dried and then reconstituted with a suitable solvent just prior to administration.

In more detailed embodiments, compositions of the invention may comprise an anti-Id compound encapsulated for delivery in microcapsules, microparticles, or microspheres, prepared, for example, by coacervation techniques or by interfacial polymerization, for example, hydroxymethylcellulose or gelatin-microcapsules and poly(methylmethacylate) microcapsules, respectively; in colloidal drug delivery systems (for example, liposomes, albumin microspheres, microemulsions, nano-particles and nanocapsules); or within macroemulsions.

As noted above, in certain embodiments the methods and compositions of the invention may employ pharmaceutically acceptable salts, e.g., acid addition or base salts of the above-described anti-Id (apoptosis inducing, cellular proliferation inhibiting, chemotherapeutic enhancing, transcription regulating, anti-inflammatory, cellular differentiation promoting, cellular transformation modulating, cell migration and metastasis modulating) compounds and/or related or derivative compounds. Examples of pharmaceutically acceptable addition salts include inorganic and organic acid addition salts. Suitable acid addition salts are formed from acids which form non-toxic salts, for example, hydrochloride, hydrobromide, hydroiodide, sulphate, hydrogen sulphate, nitrate, phosphate, and hydrogen phosphate salts. Additional pharmaceutically acceptable salts include, but are not limited to, metal salts such as sodium salts, potassium salts, cesium salts and the like; alkaline earth metals such as calcium salts, magnesium salts and the like; organic amine salts such as triethylamine salts, pyridine salts, picoline salts, ethanolamine salts, triethanolamine salts, dicyclohexylamine salts, N,N'-dibenzylethylenediamine salts and the like; organic acid salts such as acetate, citrate, lactate, succinate, tartrate, maleate, fumarate, mandelate, acetate, dichloroacetate, trifluoroacetate, oxalate, and formate salts; sulfonates such as methanesulfonate, benzenesulfonate, and p-toluenesulfonate salts; and amino acid salts such as arginate, asparginate, glutamate, tartrate, and gluconate salds. Suitable base salts are formed from bases that form non-toxic salts, for example aluminum, calcium, lithium, magnesium, potassium, sodium, zinc and diethanolamine salts.

Other detailed embodiments, the methods and compositions of the invention for employ prodrugs of the compounds of Formula I and/or Formula III. Prodrugs are considered to be any covalently bonded carriers which release the active parent drug in vivo. Examples of prodrugs useful within the invention include esters or amides with hydroxyalkyl or aminoalkyl as a substituent. These may be prepared by reacting such compounds as described above with anhydrides such as succinic anhydride.

The invention disclosed herein will also be understood to encompass methods and compositions comprising compounds of Formula I and/or III or additional compounds in Table 1 and 2, using in vivo metabolic products of the said compounds (either generated in vivo after administration of the subject precursor compound, or directly administered in the form of the metabolic product itself). Such products may result for example from the oxidation, reduction, hydrolysis, amidation, esterification and the like of the administered compound, primarily due to enzymatic processes. Accordingly, the invention includes methods and compositions of the invention employing compounds produced by a process comprising contacting an anti-Id compound with a mammalian subject for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein will also be understood to encompass diagnostic compositions for diagnosing the risk level, presence, severity, or treatment indicia of, or otherwise managing a cellular proliferative disease or condition in a mammalian subject, comprising contacting a labeled (e.g., isotopically labeled, fluorescent labeled or otherwise labeled to permit detection of the labeled compound using conventional methods) anti-Id compound to a mammalian subject (e.g., to a cell, tissue, organ, or individual) at risk or presenting with one or more symptom(s) of cellular proliferative disease, and thereafter detecting the presence, location, metabolism, and/or binding state (e.g., detecting binding to an unlabeled binding partner of Id, or to an Id) of the labeled compound using any of a broad array of known assays and labeling/detection methods. In exemplary embodiments, an anti-Id compound is isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. The isotopically-labeled compound is then administered to an individual or other subject and subsequently detected as described above, yielding useful diagnostic and/or therapeutic management data, according to conventional techniques.

Also provided are kits and systems that find use in practicing the subject methods, as described above. For example, kits and systems for practicing the subject methods may include one or more pharmaceutical formulations, which include one or both of the anti-Id (apoptosis inducing, cellular proliferation inhibiting, chemotherapeutic enhancing, transcription regulating, anti-inflammatory, cellular differentiation promoting, cellular transformation modulating, cell migration and metastasis modulating) active agent and/or another chemotherapeutic as well as toxicity reducing agents. As such, in certain embodiments the kits may include a single pharmaceutical composition, present as one or more unit dosages, where the composition includes both the anti-Id active agent, possibly a chemotherapeutic agent and possibly also a toxicity reducing agent. In yet other embodiments, the kits may include three or more separate pharmaceutical compositions, each containing an anti-Id active agent, a chemotherapeutic or possibly a toxicity reducing agent, or a combination of these elements.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits. For example, a kit according to one embodiment includes as a first component (a) instructions for using an anti-Id agent, possibly a chemotherapeutic and also possibly a toxicity reducing agent.

As used herein and in the appended claims, the singular forms "a," "an," and "the" include plural reference unless the context clearly dictates otherwise. The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

EXAMPLES

The experiments disclosed herein describe the identification of 364 compounds and the design of twelve peptides which can be used for inhibiting Id. The experiments further disclose means for identifying additional anti-Id compounds as well as for analyzing the effectiveness of the compounds in inhibiting Id. The cellular assays described below are exemplary means for testing the effectiveness of identified compounds in binding Id without inhibiting Id binding partners and may be applied to all of the identified compounds.

Example I

Identification of Test Compounds 1.1 million compounds were screened using three dimensional E47-ID1 interaction mapping to identify small molecules that could potentially inhibit E47-Id1 interaction.

An Id1 binding site was determined and virtual screening against the solution Id1 structure performed. The Monte Carlo simulation for the complex of Id1 and the small compound (helical fragments fixed) was run for 1,000,000 steps and 100 conformations were collected and analyzed. The complex conformation with the best score and best total energy was selected for further analysis.

The top 3,000 compounds from the virtual screening were then further analyzed for ClogP<5, tPSA<80, Molecular Weight<600, and chemical and biochemical stability.

The 364 compounds identified by the in silico screen are listed in Table 1, below.

TABLE 1

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 1 | Sigma Aldrich (Salor) | 21333 | C21H27ClN6O3 | 446.94074 | RCL L11, 321-2 |
| 2 | Sigma Aldrich (Salor) | 38998 | C19H24O6 | 348.39953 | 2-methoxyethyl 5-(3,3-dimethyl-2-oxobutoxy)-2-methyl-1-benzofuran-3-carboxylate |
| 3 | Sigma Aldrich (Salor) | 9104 | C30H24N2O7 | 524.53498 | di-me 3-(3,4-di-meo-ph)7-(1-naphthoyl)pyrrolo(1,2-c)pyrimidine-5,6-dicarboxylate |
| 4 | Sigma Aldrich (Salor) | 5231 | C25H30N4O6S | 514.60505 | RCL L18,827-1 |
| 5 | Sigma Aldrich (Salor) | 8995 | C27H25FN2O6S | 524.5725 | RCL L19,192-2 |
| 6 | Sigma Aldrich (Salor) | 82634 | C19H25N5O3 | 371.4428 | RCL L21,483-3 |
| 7 | Sigma Aldrich (Salor) | 27903 | C24H34N6O2 | 438.57758 | RCL L34,410-9 |
| 8 | Sigma Aldrich (Salor) | 7476 | C27H31BrN2O5 | 543.46252 | RCL L34,794-9 |
| 9 | Sigma Aldrich (Salor) | 37368 | C26H29N3O7 | 495.53693 | RCL L34,836-8 |
| 10 | Sigma Aldrich (Salor) | 36895 | C28H33FN2O5 | 496.58401 | RCL L34,930-5 |
| 11 | Sigma Aldrich (Salor) | 7461 | C25H26BrFN2O5 | 533.39877 | RCL L35,342-6 |
| 12 | Sigma Aldrich (Salor) | 35120 | C19H21N5O2S | 383.47552 | N-(4-ethoxyphenyl)-2-((4-ET-5-(3-pyridinyl)-4H-1,2,4-triazol-3-yl)thio)acetamide |
| 13 | Sigma Aldrich (Salor) | 37803 | C19H18N4O3S2 | 414.50831 | ME 4-((((4-allyl-5-(2-thienyl)-4h-1,2,4-triazol-3-yl)thio)acetyl)amino)benzoate |
| 14 | Sigma Aldrich (Salor) | 37302 | C25H27FN2O6 | 470.50214 | RCL L42,816-7 |
| 15 | Sigma Aldrich (Salor) | 8158 | C32H27FN2O5 | 538.58079 | RCL L42,856-6 |
| 16 | Sigma Aldrich (Salor) | 18153 | C21H17N3O4S | 407.45134 | RCL L43,208-3 |
| 17 | Sigma Aldrich (Salor) | 8986 | C29H30N2O6 | 502.57225 | RCL L43,214-8 |
| 18 | Sigma Aldrich (Salor) | 37037 | C21H29N5O5 | 431.49578 | RCL R13,767-7 |
| 19 | Sigma Aldrich (Salor) | 37398 | C26H38O8 | 478.58796 | 3-beta,5-diacetoxy-17-alpha-ethoxycarbonyl-5-beta,14-beta-androstan-19-oic acid |
| 20 | Sigma Aldrich (Salor) | 31635 | C14H18ClN5O | 307.78546 | |
| 21 | Sigma Aldrich (Salor) | 51498 | C18H17NO5S | 359.40389 | 2,4-dimethoxybenzyl (2-oxo-1,3-benzothiazol-3(2h)-yl)acetate |
| 22 | Sigma Aldrich (Salor) | 51942 | C18H29NO4 | 323.43613 | 2-ethyl-4-(2-hydroxy-3-(isopropylamino)propoxy)-3,6-dimethylphenyl acetate |
| 23 | Sigma Aldrich (Salor) | 52552 | C18H21N7O3S | 415.47717 | RCL R60,176-4 |
| 24 | Sigma Aldrich (Salor) | 52789 | C25H22BrClN2O3 | 513.82269 | RCL R60,587-5 |
| 25 | Sigma Aldrich (Salor) | 57620 | C18H22O5 | 318.37304 | ethyl 5-(3,3-dimethyl-2-oxobutoxy)-2-methyl-1-benzofuran-3-carboxylate |
| 26 | Sigma Aldrich (Salor) | 62638 | C26H24N2O6 | 460.49098 | ethyl 7-benzoyl-3-(3,4,5-trimethoxyphenyl)pyrrolo(1,2-c)pyrimidine-5-carboxylate |
| 27 | Sigma Aldrich (Salor) | 63670 | C17H21N7OS | 371.46722 | RCL R77,075-2 |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 28 | Sigma Aldrich (Salor) | 67007 | C26H23ClN2O6 | 494.93601 | et 7-(4-cl-benzoyl)-3-(3,4,5-tri-meo-ph)pyrrolo(1,2-c)pyrimidine-5-carboxylate |
| 29 | Sigma Aldrich (Salor) | 67588 | C24H23N5O3 | 429.48261 | RCL R82,426-7 |
| 30 | Sigma Aldrich (Salor) | 69309 | C21H16FN3O4S | 425.44177 | RCL R84,320-2 |
| 31 | Sigma Aldrich (Salor) | 73610 | C23H21N3O4S | 435.50552 | RCL R89,190-8 |
| 32 | ChemDiv | 1630-0168 | C23H29NO5 | 399.49128 | 4-(3,5-Dimethoxy-phenyl)-2,7,7-trimethyl-5-oxo-1,4,5,6,7,8-hexahydro-quinoline-3 |
| 33 | ChemDiv | 1630-1220 | C24H31NO6 | 429.51777 | 2,7,7-Trimethyl-5-oxo-4-(3,4,5-trimethoxy-phenyl)-1,4,5,6,7,8-hexahydro-quinolin |
| 34 | ChemDiv | 2188-3775 | C23H20O8 | 424.41105 | 5-(acetyloxy)-3-(3,4-dihydro-2H-1,5-benzodioxepin-7-yl)-2-methyl-4-oxo-4H-chromen-7-yl acetate |
| 35 | ChemDiv | 2326-3307 | C25H26N2O4 | 418.49697 | ethyl 7-(4-methoxyphenyl)-2-methyl-5-oxo-4-pyridin-2-yl-1,4,5,6,7,8-hexahydroquinoline-3-carboxylate |
| 36 | ChemDiv | 2556-0150 | C26H25N3O5S | 491.57025 | methyl (2E)-5-[4-(acetyloxy)phenyl]-2-[4-(dimethylamino)benzylidene]-7-methyl-3-oxo-2,3-dihydro-5H-[1,3]thiazolo[3,2-a]pyrimidine-6-carboxylate |
| 37 | ChemDiv | 3165-0032 | C22H32O7 | 408.49614 | Structure contains non-supported carbohydrate derivative! |
| 38 | ChemDiv | 3175-0669 | C16H15N7O4 | 369.34245 | ethyl {5-[(4-methoxyphenyl)amino][1,2,5]oxadiazolo[3,4-e][1,2,4]triazolo[4,3-a]pyrazin-8-yl}acetate |
| 39 | ChemDiv | 3261-0890 | C26H27N3O2 | 413.52399 | N-{2-[(4-benzylpiperazin-1-yl)carbonyl]phenyl}-2-methylbenzamide |
| 40 | ChemDiv | 3261-1069 | C25H26N2O4S | 450.56097 | N-(2-ethoxyphenyl)-2-{[(4-methoxyphenyl)acetyl]amino}-5,6-dihydro-4H-cyclopenta[b]thiophene-3-carboxamide |
| 41 | ChemDiv | 3379-1141 | C27H27NO5 | 445.51994 | N-Benzo[1,3]dioxol-5-ylmethyl-N-(3-benzo[1,3]dioxol-5-yl-4-phenyl-butyl)-acetami |
| 42 | ChemDiv | 3381-0024 | C20H28N2O3 | 344.45776 | 3-Cyclopentyl-1-[4-(3-methoxy-benzoyl)-piperazin-1-yl]-propan-1-one |
| 43 | ChemDiv | 3381-0867 | C22H30N2O4 | 386.4954 | 1-(4-methoxybenzyl)-4-(2,4,5-trimethoxybenzyl)piperazine |
| 44 | ChemDiv | 3389-1127 | C25H21N5O3 | 439.47782 | N-{(1Z)-(benzoylamino)[(6-methoxy-4-methylquinazolin-2-yl)amino]methylene}benzamide |
| 45 | ChemDiv | 3389-2300 | C17H19N5O2 | 325.37328 | 2-[(6-ethoxy-4-methylquinazolin-2-yl)amino]-5,6-dimethylpyrimidin-4(1H)-one |
| 46 | ChemDiv | 3448-2775 | C22H24N2O6 | 412.44638 | Acetic acid 4-(2-amino-3-cyano-7,7-dimethyl-5-oxo-5,6,7,8-tetrahydro-4H-chromen- |
| 47 | ChemDiv | 3448-2800 | C15H13BrN2O4 | 365.18586 | 5-Bromo-furan-2-carboxylic acid [1-carbamoyl-2-(4-methoxy-phenyl)-vinyl]-amide |
| 48 | ChemDiv | 3448-4038 | C24H27N3O6 | 453.49929 | 4-(2-amino-3-cyano-7,7-dimethyl-5-oxo-5,6,7,8-tetrahydro-4H-chromen-4-yl)-2-methoxyphenyl morpholine-4-carboxylate |
| 49 | ChemDiv | 3448-5595 | C23H28N2O7S2 | 508.61681 | ethyl 2-{[4-methoxy-3-(morpholin-4-ylsulfonyl)benzoyl]amino}-4,5,6,7-tetrahydro-1-benzothiophene-3-carboxylate |
| 50 | ChemDiv | 3456-4126 | C21H23N5O3S | 425.51316 | N-{(1Z)-[(4,6-dimethylpyrimidin-2-yl)amino][(4-methoxyphenyl)amino]methylene}-4-methylbenzenesulfonamide |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 51 | ChemDiv | 3490-5511 | C24H24N2O5S | 452.53328 | ethyl 5-{[(2-methoxyphenyl)amino]carbonyl}-4-methyl-2-[(2-methylbenzoyl)amino]thiophene-3-carboxylate |
| 52 | ChemDiv | 3570-0584 | C18H22O5 | 318.37304 | ethyl 5-(3,3-dimethyl-2-oxobutoxy)-2-methyl-1-benzofuran-3-carboxylate |
| 53 | ChemDiv | 3628-0018 | C17H16N4O4S2 | 404.46947 | 2-[2-(4-Methyl-6-oxo-1,6-dihydro-pyrimidin-2-ylsulfanyl)-acetylamino]-benzothiaz |
| 54 | ChemDiv | 3647-0173 | C25H29N3O3 | 419.52818 | N~1~-2,3-dihydro-1H-cyclopenta[b]quinolin-9-yl-N~2~-[2-(3,4-dimethoxyphenyl)ethyl]-N~2~-methylglycinamide |
| 55 | ChemDiv | 3771-3242 | C23H19N3O5S | 449.48898 | 2-(1,3-dioxo-1,3-dihydro-2H-isoindol-2-yl)-N-(4-{[(4-methylphenyl)sulfonyl]amino}phenyl)acetamide |
| 56 | ChemDiv | 3772-2735 | C18H17F2NO5S | 397.40069 | ethyl 5-acetyl-2-{[(2,4-difluorophenoxy)acetyl]amino}-4-methylthiophene-3-carboxylate |
| 57 | ChemDiv | 3909-7622 | C20H21N3O4S | 399.47207 | ethyl 2,5-dimethyl-3-{2-[(3-methylphenyl)amino]-2-oxoethyl}-4-oxo-3,4-dihydrothieno[2,3-d]pyrimidine-6-carboxylate |
| 58 | ChemDiv | 3909-8437 | C19H18FN3O4S | 403.43541 | ethyl 4-[(4-fluorophenyl)amino]-2-(2-methoxy-2-oxoethyl)-5-methylthieno[2,3-d]pyrimidine-6-carboxylate |
| 59 | ChemDiv | 4056-0020 | C24H36O7 | 436.55032 | Structure contains non-supported carbohydrate derivative! |
| 60 | ChemDiv | 4103-0179 | C28H26ClNO5 | 491.97612 | [9-{2-[(4-chlorobenzyl)oxy]phenyl}-1,8-dioxo-2,3,4,5,6,7,8,9-octahydroacridin-10(1H)-yl]acetic acid |
| 61 | ChemDiv | 4239-0332 | C19H28N2O5 | 364.44541 | ethyl 1-{3-[(2,5-dimethoxyphenyl)amino]-3-oxopropyl}piperidine-4-carboxylate |
| 62 | ChemDiv | 4239-0638 | C18H26N2O4 | 334.41892 | ethyl 1-{3-[(2-methoxyphenyl)amino]-3-oxopropyl}piperidine-4-carboxylate |
| 63 | ChemDiv | 4333-2372 | C20H19N5O | 345.40733 | N-(4-ethoxyphenyl)-1-(4-methylphenyl)-1H-pyrazolo[3,4-d]pyrimidin-4-amine |
| 64 | ChemDiv | 4333-4418 | C25H29N3O7 | 483.52578 | 4-(2-amino-3-cyano-7,7-dimethyl-5-oxo-5,6,7,8-tetrahydro-4H-chromen-4-yl)-2,6-dimethoxyphenyl morpholine-4-carboxylate |
| 65 | ChemDiv | 4340-1254 | C24H19FN2O5S | 466.49183 | ethyl 2-[3-(4-fluorobenzoyl)-4-hydroxy-5-oxo-2-phenyl-2,5-dihydro-1H-pyrrol-1-yl]-4-methyl-1,3-thiazole-5-carboxylate |
| 66 | ChemDiv | 4340-2838 | C21H16FN3O4S | 425.44177 | 5-(4-Fluoro-phenyl)-3-hydroxy-4-(4-methoxy-benzoyl)-1-(5-methyl-[1,3,4]thiadiazo |
| 67 | ChemDiv | 4340-2840 | C21H16BrN3O4S | 486.34737 | 5-(4-bromophenyl)-3-hydroxy-4-(4-methoxybenzoyl)-1-(5-methyl-1,3,4-thiadiazol-2-yl)-1,5-dihydro-2H-pyrrol-2-one |
| 68 | ChemDiv | 4340-2841 | C21H16FN3O4S | 425.44177 | 5-(2-fluorophenyl)-3-hydroxy-4-(4-methoxybenzoyl)-1-(5-methyl-1,3,4-thiadiazol-2-yl)-1,5-dihydro-2H-pyrrol-2-one |
| 69 | ChemDiv | 4358-1468 | C23H24N2O5 | 408.45813 | ethyl 6-methoxy-4-{[4-(propoxycarbonyl)phenyl]amino}quinoline-3-carboxylate |
| 70 | ChemDiv | 4373-0609 | C20H17ClN2O6 | 416.82129 | (4-{(Z)-[1-(4-chlorobenzyl)-2,5-dioxoimidazolidin-4-ylidene]methyl}-2-methoxyphenoxy)acetic acid |
| 71 | ChemDiv | 4424-0281 | C27H25FN2O4 | 460.5097 | 5-(4-fluorophenyl)-3-hydroxy-4-(3-methyl-4-propoxybenzoyl)-1-(pyridin-3-ylmethyl)-1,5-dihydro-2H-pyrrol-2-one |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 72 | ChemDiv | 4530-7179 | C20H20N2O5 | 368.3928 | 4-Acetyl-5-(2,4-dimethoxy-phenyl)-3-hydroxy-1-pyridin-3-ylmethyl-1,5-dihydro-pyr |
| 73 | ChemDiv | 4530-7180 | C20H20N2O5 | 368.3928 | 4-Acetyl-5-(3,4-dimethoxy-phenyl)-3-hydroxy-1-pyridin-3-ylmethyl-1,5-dihydro-pyr |
| 74 | ChemDiv | 4554-6136 | C24H19N3O4 | 413.43673 | ethyl 4-[(4-isonicotinoyl-1-oxo-1,2-dihydroisoquinolin-3-yl)amino]benzoate |
| 75 | ChemDiv | 4568-7319 | C19H23NO7 | 377.39766 | 4-(3-Hydroxy-4-methoxy-phenyl)-1-(2-methoxy-ethyl)-1,4-dihydro-pyridine-3,5-dica |
| 76 | ChemDiv | 4781-0145 | C28H27ClN2O6 | 522.99019 | methyl N-{[1-(4-chlorophenyl)-7,7-dimethyl-2,5-dioxo-1,2,5,6,7,8-hexahydroquinolin-3-yl]carbonyl}tyrosinate |
| 77 | ChemDiv | 4884-9066 | C21H20N2O6 | 396.40335 | 4-[3-Hydroxy-4-(4-methoxy-benzoyl)-2-oxo-5-pyridin-3-yl-2,5-dihydro-pyrrol-1-yl] |
| 78 | ChemDiv | 4964-1881 | C22H28N2O6 | 416.47826 | 4-{[4-(3,5-dimethoxybenzoyl)piperazin-1-yl]methyl}-2,6-dimethoxyphenol |
| 79 | ChemDiv | 5088-1067 | C14H21N3O4S | 327.40517 | 5-Butyl-6-hydroxy-2-(2-morpholin-4-yl-2-oxo-ethylsulfanyl)-3H-pyrimidin-4-one |
| 80 | ChemDiv | 5174-4662 | C20H18N2O5 | 366.37686 | 3-{[3-(ethoxycarbonyl)-8-methoxyquinolin-4-yl]amino}benzoic acid |
| 81 | ChemDiv | 5225-5918 | C23H20N6O2S | 444.51885 | N-(2-methoxyphenyl)-5-methyl-7-pyridin-2-yl-2-thien-2-yl-4,7-dihydro[1,2,4]triazolo[1,5-a]pyrimidine-6-carboxamide |
| 82 | ChemDiv | 5300-0256 | C15H21N5O | 287.36752 | N~4~-(4-methoxyphenyl)-1,3,5-triazaspiro[5.5]undeca-1,3-diene-2,4-diamine |
| 83 | ChemDiv | 5308-0047 | C20H19F3N2O4 | 408.38063 | methyl 4-[4-(acetylamino)phenoxy]-2,3,5-trifluoro-6-pyrrolidin-1-ylbenzoate |
| 84 | ChemDiv | 5340-0106 | C23H23BrN2O5 | 487.35416 | ethyl 3-bromo-4-{[4-(ethoxycarbonyl)phenyl]amino}-2-methyl-5-oxo-1-phenyl-2,5-dihydro-1H-pyrrole-2-carboxylate |
| 85 | ChemDiv | 5504-0221 | C13H19N7OS | 321.40668 | 1-(2-{[4,6-bis(ethylamino)-1,3,5-triazin-2-yl]amino}-4-methyl-1,3-thiazol-5-yl)ethanone |
| 86 | ChemDiv | 5516-0713 | C20H18N4O5 | 394.39026 | 2-{5-[Bis-(5-hydroxy-3-methyl-1H-pyrazol-4-yl)-methyl]-furan-2-yl}-benzoic acid |
| 87 | ChemDiv | 5516-0721 | C20H18N4O5 | 394.39026 | 3-{5-[Bis-(5-hydroxy-3-methyl-1H-pyrazol-4-yl)-methyl]-furan-2-yl}-benzoic acid |
| 88 | ChemDiv | 5519-0769 | C17H16N2O2 | 280.32927 | 2-Methoxy-6-(quinolin-3-ylaminomethyl)-phenol |
| 89 | ChemDiv | 5593-2150 | C22H25N3O5S | 443.52565 | (2Z)-3-(3,4-dimethoxybenzyl)-2-[(4-methoxyphenyl)imino]-N-methyl-4-oxo-1,3-thiazinane-6-carboxamide |
| 90 | ChemDiv | 5645-0519 | C18H21N5O2 | 339.40037 | 2-(6-Ethoxy-4-methyl-quinazolin-2-ylamino)-5-ethyl-6-methyl-1H-pyrimidin-4-one |
| 91 | ChemDiv | 5782-5526 | C23H18ClNO4 | 407.85721 | 2-[(2-benzoyl-4-chlorophenyl)amino]-4-oxo-4-phenylbutanoic acid |
| 92 | ChemDiv | 5910-0128 | C19H21N5O2 | 351.41152 | 2-[(6-ethoxy-4-methylquinazolin-2-yl)amino]-5,6,7,8-tetrahydroquinazolin-4(1H)-one |
| 93 | ChemDiv | 5921-0100 | C20H29N3O2 | 343.47303 | 8-butyl-3,3-dimethyl-6-[(tetrahydrofuran-2-ylmethyl)amino]-3,4-dihydro-1H-pyrano[3,4-c]pyridine-5-carbonitrile |
| 94 | ChemDiv | 5948-0552 | C21H23NO6 | 385.42056 | 2-Amino-4-(4-methoxycarbonyl-phenyl)-7,7-dimethyl-5-oxo-5,6,7,8-tetrahydro-4H-ch |
| 95 | ChemDiv | 5969-0051 | C20H23NO4 | 341.41061 | isobutyl-2-benzyl-1-oxo-1,2,3,6,7,7a-hexahydro-3a,6-epoxyisoindole-7-carboxylate |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 96 | ChemDiv | 6047-0631 | C16H17N5O5 | 359.34439 | methyl 6-acetyl-7-(3-ethoxy-4-hydroxyphenyl)-4,7-dihydrotetrazolo[1,5-a]pyrimdine-5-carboxylate |
| 97 | ChemDiv | 6049-0384 | C25H25N5O7 | 507.5073 | N-{2-[(6,7-dimethoxyisoquinolin-1-yl)methyl]-4,5-dimethoxyphenyl}-1-methyl-4-nitro-1H-pyrazole-5-carboxamide |
| 98 | ChemDiv | 6049-1667 | C17H24N2O4S | 352.45583 | 4-{[3-(aminocarbonyl)-6-tert-butyl-4,5,6,7-tetrahydro-1-benzothien-2-yl]amino}-4-oxobutanoic acid |
| 99 | ChemDiv | 6049-1966 | C26H31N3O3 | 433.55527 | N-(3-morpholin-4-ylpropyl)-2-(4-propoxyphenyl)quinoline-4-carboxamide |
| 100 | ChemDiv | 6049-2161 | C20H19NO4 | 337.37873 | 2-(2,4-diethoxyphenyl)quinoline-4-carboxylic acid |
| 101 | ChemDiv | 6074-2661 | C20H22N4O2 | 350.42394 | N-(2,4-dimethoxyphenyl)-2-pyrrolidin-1-ylquinazolin-4-amine |
| 102 | ChemDiv | 6173-0372 | C20H19ClFN5O2S | 447.92213 | N-{(1Z)-[(3-chloro-4-fluorophenyl)amino][(4,6-dimethylpyrimidin-2-yl)amino]methylene}-1-phenylmethanesulfonamide |
| 103 | ChemDiv | 6186-3357 | C23H23N3O5 | 421.45686 | 2-{2-[4-(1,3-benzodioxol-5-ylmethyl)piperazin-1-yl]-1-methyl-2-oxoethyl}-1H-isoindole-1,3(2H)-dione |
| 104 | ChemDiv | 6203-0027 | C29H32N2O5 | 488.58879 | N-(4-butoxyphenyl)-1-(4-methoxyphenyl)-7,7-dimethyl-2,5-dioxo-1,2,5,6,7,8-hexahydroquinoline-3-carboxamide |
| 105 | ChemDiv | 6203-0030 | C26H25ClN2O4 | 464.95315 | N-(4-butoxyphenyl)-1-(4-chlorophenyl)-2,5-dioxo-1,2,5,6,7,8-hexahydroquinoline-3-carboxamide |
| 106 | ChemDiv | 6321-0474 | C19H20ClN5O | 369.85715 | 5-(4-chlorophenyl)-7-(4-ethoxyphenyl)-4,5,6,7-tetrahydro[1,2,4]triazolo[1,5-a]pyrimidin-2-amine |
| 107 | ChemDiv | 6321-0495 | C19H20BrN5O2 | 430.30755 | 5-(4-bromophenyl)-7-(3,4-dimethoxyphenyl)-4,5,6,7-tetrahydro[1,2,4]triazolo[1,5-a]pyrimidin-2-amine |
| 108 | ChemDiv | 8001-2649 | C23H29NO7 | 431.49008 | ethyl 2-amino-7,7-dimethyl-5-oxo-4-(3,4,5-trimethoxyphenyl)-5,6,7,8-tetrahydro-4H-chromene-3-carboxylate |
| 109 | ChemDiv | 8006-1511 | C23H22N2O6 | 422.44159 | Multiplicative nomenclature is not supported in current version! |
| 110 | ChemDiv | 8008-1642 | C20H22N2O6 | 386.40814 | 2-Amino-7,7-dimethyl-4-(4-nitro-phenyl)-5-oxo-5,6,7,8-tetrahydro-4H-chromene-3-c |
| 111 | ChemDiv | 8009-2594 | C22H25N3O4S | 427.52625 | ethyl 10-(3-morpholin-4-ylpropanoyl)-10H-phenothiazin-3-ylcarbamate |
| 112 | ChemDiv | 8010-3646 | C25H29N3O6 | 467.52638 | 4-(2-amino-3-cyano-7,7-dimethyl-5-oxo-5,6,7,8-tetrahydro-4H-chromen-4-yl)-2-ethoxyphenyl morpholine-4-carboxylate |
| 113 | ChemDiv | 8010-3952 | C21H19ClN2O4 | 398.84958 | N-{2-[3-(4-chlorobenzoyl)-4-hydroxy-5-oxo-2-phenyl-2,5-dihydro-1H-pyrrol-1-yl]ethyl}acetamide |
| 114 | ChemDiv | 8010-4802 | C17H18N2O3 | 298.34461 | (3aR,7aS)-2-{[(4-acetylphenyl)amino]methyl}-3a,4,7,7a-tetrahydro-1H-isoindole-1,3(2H)-dione |
| 115 | ChemDiv | 8010-5568 | C21H25N3O4 | 383.4511 | 2-Azepan-1-yl-N-(2-ethoxy-phenyl)-5-nitro-benzamide |
| 116 | ChemDiv | 8011-2013 | C24H22N2O5S | 450.51734 | 4-(2-amino-3-cyano-7,7-dimethyl-5-oxo-5,6,7,8-tetrahydro-4H-chromen-4-yl)-2-methoxyphenyl thiophene-2-carboxylate |
| 117 | ChemDiv | 8011-9076 | C25H23N3O7S | 509.54196 | 4-(2-amino-3-cyano-7,7-dimethyl-5-oxo-5,6,7,8-tetrahydro-4H- |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| | | | | | chromen-4-yl)-2-ethoxy-6-nitrophenyl thiophene-2-carboxylate |
| 118 | ChemDiv | 8011-9794 | C23H21ClN2O3 | 408.88842 | N'-acetyl-N'-(3-chloro-4-methylphenyl)-2-hydroxy-2,2-diphenylacetohydrazide |
| 119 | ChemDiv | 8012-0505 | C27H22N2O7 | 486.48559 | 4-[2-amino-3-cyano-7-(2-furyl)-5-oxo-5,6,7,8-tetrahydro-4H-chromen-4-yl]-2-ethoxyphenyl 2-furoate |
| 120 | ChemDiv | 8012-4962 | C23H22FN3O5 | 439.44729 | dimethyl 2-({(Z)-[1-(4-fluorophenyl)-5-oxo-3-propyl-1,5-dihydro-4H-pyrazol-4-ylidene]methyl}amino)terephthalate |
| 121 | ChemDiv | 8012-9025 | C23H27N9O4 | 493.52954 | 8-[(4-amino-6-morpholin-4-yl-1,3,5-triazin-2-yl)methoxy]-1,3-dimethyl-7-(4-methylbenzyl)-3,7-dihydro-1H-purine-2,6-dione |
| 122 | ChemDiv | C053-0437 | C21H22N2O5 | 382.41989 | ethyl 4-[(3,4-dimethoxyphenyl)amino]-8-methoxyquinoline-3-carboxylate |
| 123 | ChemDiv | C066-0774 | C31H33N3O6 | 543.62516 | ethyl 4-{[2,3-bis(4-methoxyphenyl)-1-oxo-1,2,3,4-tetrahydroisoquinolin-4-yl]carbonyl}piperazine-1-carboxylate |
| 124 | ChemDiv | C094-0186 | C21H23N3O6 | 413.43396 | N~2~-acetyl-N~1~-[2-(2,3-dihydro-1,4-benzodioxin-6-ylamino)-1-(4-methoxyphenyl)-2-oxoethyl]glycinamide |
| 125 | ChemDiv | C094-1489 | C22H32N2O4 | 388.51134 | ethyl 1-[2-(cyolopentylamino)-1-(4-methoxyphenyl)-2-oxoethyl]piperidine-4-carboxylate |
| 126 | ChemDiv | C094-1545 | C20H30N2O2 | 330.4743 | N-cyclohexyl-2-(4-methoxyphenyl)-2-piperidin-1-ylacetamide |
| 127 | ChemDiv | C094-2389 | C20H29N3O7 | 423.47003 | N-cyclohexyl-2-[(2,2-dimethoxyethyl)(methyl)amino]-2-(6-nitro-1,3-benzodioxol-5-yl)acetamide |
| 128 | ChemDiv | C094-2391 | C18H23N3O5 | 361.40111 | N-cyclopentyl-2-(6-nitro-1,3-benzodioxol-5-yl)-2-pyrrolidin-1-ylacetamide |
| 129 | ChemDiv | C094-2399 | C22H25N3O5 | 411.46165 | 2-[benzyl(methyl)amino]-N-cyclopentyl-2-(6-nitro-1,3-benzodioxol-5-yl)acetamide |
| 130 | ChemDiv | C094-2425 | C19H27N3O7 | 409.44294 | N-cyclopentyl-2-[(2,2-dimethoxyethyl)(methyl)amino]-2-(6-nitro-1,3-benzodioxol-5-yl)acetamide |
| 131 | ChemDiv | C096-0455 | C23H32N4O6S2 | 524.66269 | ethyl 1-{[6-methyl-5-[(4-methylpiperidin-1-yl)sulfonyl]-4-oxothieno[2,3-d]pyrimidin-3(4H)-yl]acetyl}piperidine-4-carboxylate |
| 132 | ChemDiv | C096-1176 | C22H26N2O4 | 382.46352 | 3-(4-methoxyphenyl)-N-(3-methoxypropyl)-2-methyl-1-oxo-1,2,3,4-tetrahydroisoquinoline-4-carboxamide |
| 133 | ChemDiv | C096-1437 | C31H34FN3O4 | 531.63273 | 2-(4-fluorobenzyl)-3-(4-methoxyphenyl)-N-(3-morpholin-4-ylpropyl)-1-oxo-1,2,3,4-tetrahydroisoquinoline-4-carboxamide |
| 134 | ChemDiv | C098-0636 | C27H26N4O5 | 486.53207 | ethyl (2Z)-2-[(2-methylbenzoyl)imino]-5-oxo-1-(tetrahydrofuran-2-ylmethyl)-1,5-dihydro-2H-dipyrido[1,2-a:2',3'-d]pyrimidine-3-carboxylate |
| 135 | ChemDiv | C102-0192 | C15H18N4O3 | 302.33571 | methyl 4-[(6-tert-butyl-5-oxo-4,5-dihydro-1,2,4-triazin-3-yl)amino]benzoate |
| 136 | ChemDiv | C115-0426 | C27H25F3N2O5 | 514.5059 | 6,7-dimethoxy-3-(4-methoxyphenyl)-2-methyl-1-oxo-N-[3-(trifluoromethyl)phenyl]-1,2,3,4-tetrahydroisoquinoline-4-carboxamide |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 137 | ChemDiv | C115-0432 | C26H24ClFN2O5 | 498.94298 | N-(3-chloro-4-fluorophenyl)-6,7-dimethoxy-3-(4-methoxyphenyl)-2-methyl-1-oxo-1,2,3,4-tetrahydroisoquinoline-4-carboxamide |
| 138 | ChemDiv | C115-0450 | C27H25F3N2O5 | 514.5059 | 6,7-dimethoxy-3-(4-methoxyphenyl)-2-methyl-1-oxo-N-[4-(trifluoromethyl)phenyl]-1,2,3,4-tetrahydroisoquinoline-4-carboxamide |
| 139 | ChemDiv | C115-0452 | C28H28N2O7 | 504.54456 | N-2,3-dihydro-1,4-benzodioxin-6-yl-6,7-dimethoxy-3-(4-methoxyphenyl)-2-methyl-1-oxo-1,2,3,4-tetrahydroisoquinoline-4-carboxamide |
| 140 | ChemDiv | C115-0485 | C24H30N2O5 | 426.5171 | N-butyl-6,7-dimethoxy-3-(4-methoxyphenyl)-2-methyl-1-oxo-1,2,3,4-tetrahydroisoquinoline-4-carboxamide |
| 141 | ChemDiv | C125-0425 | C24H22ClN3O4 | 451.91364 | N-(3-chlorophenyl)-6,7-dimethoxy-2-methyl-1-oxo-3-pyridin-3-yl-1,2,3,4-tetrahydroisoquinoline-4-carboxamide |
| 142 | ChemDiv | C125-0426 | C25H22F3N3O4 | 485.46699 | 6,7-dimethoxy-2-methyl-1-oxo-3-pyridin-3-yl-N-[3-(trifluoromethyl)phenyl]-1,2,3,4-tetrahydroisoquinoline-4-carboxamide |
| 143 | ChemDiv | C125-0430 | C24H29N3O4 | 423.51643 | N-cyclohexyl-6,7-dimethoxy-2-methyl-1-oxo-3-pyridin-3-yl-1,2,3,4-tetrahydroisoquinoline-4-carboxamide |
| 144 | ChemDiv | C125-0434 | C25H24ClN3O5 | 481.94013 | N-(3-chloro-4-methoxyphenyl)-6,7-dimethoxy-2-methyl-1-oxo-3-pyridin-3-yl-1,2,3,4-tetrahydroisoquinoline-4-carboxamide |
| 145 | ChemDiv | C125-0435 | C26H27N3O6 | 477.52159 | N-(2,4-dimethoxyphenyl)-6,7-dimethoxy-2-methyl-1-oxo-3-pyridin-3-yl-1,2,3,4-tetrahydroisoquinoline-4-carboxamide |
| 146 | ChemDiv | C125-0445 | C25H25N3O5 | 447.4951 | 6,7-dimethoxy-N-(3-methoxyphenyl)-2-methyl-1-oxo-3-pyridin-3-yl-1,2,3,4-tetrahydroisoquinoline-4-carboxamide |
| 147 | ChemDiv | C125-0447 | C27H29N3O7 | 507.54808 | 6,7-dimethoxy-2-methyl-1-oxo-3-pyridin-3-yl-N-(3,4,5-trimethoxyphenyl)-1,2,3,4-tetrahydroisoquinoline-4-carboxamide |
| 148 | ChemDiv | C125-0450 | C25H22F3N3O4 | 485.46699 | 6,7-dimethoxy-2-methyl-1-oxo-3-pyridin-3-yl-N-[4-(trifluoromethyl)phenyl]-1,2,3,4-tetrahydroisoquinoline-4-carboxamide |
| 149 | ChemDiv | C125-0451 | C25H24BrN3O4 | 510.39173 | N-(4-bromo-2-methylphenyl)-6,7-dimethoxy-2-methyl-1-oxo-3-pyridin-3-yl-1,2,3,4-tetrahydroisoquinoline-4-carboxamide |
| 150 | ChemDiv | C125-0452 | C26H25N3O6 | 475.50565 | N-2,3-dihydro-1,4-benzodioxin-6-yl-6,7-dimethoxy-2-methyl-1-oxo-3-pyridin-3-yl-1,2,3,4-tetrahydroisoquinoline-4-carboxamide |
| 151 | ChemDiv | C125-0472 | C26H33N3O4 | 451.57061 | N-(2,3-dimethylcyclohexyl)-6,7-dimethoxy-2-methyl-1-oxo-3-pyridin-3-yl-1,2,3,4-tetrahydroisoquinoline-4-carboxamide |
| 152 | ChemDiv | C125-0490 | C24H32N4O4 | 440.54704 | N-[2-(diethylamino)ethyl]-6,7-dimethoxy-2-methyl-1-oxo-3-pyridin-3-yl-1,2,3,4- |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 153 | ChemDiv | C125-0515 | C27H27N3O6 | 489.53274 | ethyl 2-{[(6,7-dimethoxy-2-methyl-1-oxo-3-pyridin-3-yl-1,2,3,4-tetrahydroisoquinolin-4-yl)carbonyl]amino}benzoate |
| 154 | ChemDiv | C125-0531 | C26H26ClN3O5 | 495.96722 | N-(4-chloro-2-methoxy-5-methylphenyl)-6,7-dimethoxy-2-methyl-1-oxo-3-pyridin-3-yl-1,2,3,4-tetrahydroisoquinoline-4-carboxamide |
| 155 | ChemDiv | C125-0540 | C28H38N4O4 | 494.63946 | N-[3-(3,5-dimethylpiperidin-1-yl)propyl]-6,7-dimethoxy-2-methyl-1-oxo-3-pyridin-3-yl-1,2,3,4-tetrahydroisoquinoline-4-carboxamide |
| 156 | ChemDiv | C128-0085 | C23H24N4O3 | 404.47273 | 1-({1-[(4-methoxyphenyl)amino]isoquinolin-4-yl}carbonyl)piperidine-4-carboxamide |
| 157 | ChemDiv | C138-0489 | C24H31N3O4S | 457.59637 | N-[(1-ethylpyrrolidin-2-yl)methyl]-6,7-dimethoxy-2-methyl-1-oxo-3-thien-2-yl-1,2,3,4-tetrahydroisoquinoline-4-carboxamide |
| 158 | ChemDiv | C138-0491 | C23H29N3O5S | 459.56868 | 6,7-dimethoxy-2-methyl-N-(2-morpholin-4-ylethyl)-1-oxo-3-thien-2-yl-1,2,3,4-tetrahydroisoquinoline-4-carboxamide |
| 159 | ChemDiv | C168-0237 | C22H28N2O6 | 416.47826 | ethyl 1-[(2-ethyl-6,7-dimethoxy-1-oxo-1,2-dihydroisoquinolin-4-yl)carbonyl]piperidine-3-carboxylate |
| 160 | ChemDiv | C168-0239 | C23H24N2O6 | 424.45753 | ethyl 2-{[(2-ethyl-6,7-dimethoxy-1-oxo-1,2-dihydroisoquinolin-4-yl)carbonyl]amino}benzoate |
| 161 | ChemDiv | C169-0220 | C20H16N4O3 | 360.37552 | 2-[3-(2,3-dihydro-1,4-benzodioxin-6-ylamino)imidazo[1,2-a]pyrazin-2-yl]phenol |
| 162 | ChemDiv | C186-0404 | C24H34N4O6S2 | 538.68978 | ethyl 1-{[5-[(3,5-dimethylpiperidin-1-yl)sulfonyl]-6-methyl-4-oxothieno[2,3-d]pyrimidin-3(4H)-yl]acetyl}piperidine-4-carboxylate |
| 163 | ChemDiv | C189-0091 | C22H24N2O5S2 | 460.57498 | ethyl 2-({2-[(1-methyl-1H-indol-3-yl)sulfonyl]propanoyl}amino)-5,6-dihydro-4H-cyclopenta[b]thiophene-3-carboxylate |
| 164 | ChemDiv | C197-0060 | C24H30N2O4S | 442.5817 | N-butyl-6,7-dimethoxy-2-methyl-3-[4-(methylthio)phenyl]-1-oxo-1,2,3,4-tetrahydroisoquinoline-4-carboxamide |
| 165 | ChemDiv | C202-0368 | C18H23N5O2S | 373.48031 | pentyl 5-methyl-7-[4-(methylthio)phenyl]-4,7-dihydrotetrazolo[1,5-a]pyrimidine-6-carboxylate |
| 166 | ChemDiv | C243-0098 | C21H19N3O3S | 393.46788 | N-(4-butoxyphenyl)-4-oxo-4H-pyrido[1,2-a]thieno[2,3-d]pyrimidine-2-carboxamide |
| 167 | ChemDiv | C247-0101 | C28H31NO7 | 493.56177 | (11Z)-11-[(2E)-1-hydroxy-3-(2,3,4-trimethoxyphenyl)prop-2-enylidene]-5-methoxy-1,2,3,4,9,9a-hexahydro-4a,9-(epiminoethano)xanthen-12-one |
| 168 | ChemDiv | C257-0244 | C27H28N2O4 | 444.53521 | 2-(4-ethoxy-3-methoxybenzyl)-3-oxo-N-(2-phenylethyl)isoindoline-1-carboxamide |
| 169 | ChemDiv | C258-0518 | C24H29N3O4S | 455.58043 | 2-[3-(3,4-dimethylphenyl)-2,4-dioxo-3,4,6,7,8,9-hexahydro-2H-cyclohepta[4,5]thieno[2,3-d]pyrimidin-1(5H)-yl]-N-(2-methoxyethyl)acetamide |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 170 | ChemDiv | C260-1054 | C25H21N5O5 | 471.47662 | 3-[2,4-dioxo-1-[(4-oxo-4H-pyrido[1,2-a]pyrimidin-2-yl)methyl]-1,4-dihydroquinazolin-3(2H)-yl]-N-(2-furylmethyl)propanamide |
| 171 | ChemDiv | C260-1202 | C27H27N3O4 | 457.53394 | N-(2-methoxybenzyl)-3-[1-(4-methylbenzyl)-2,4-dioxo-1,4-dihydroquinazolin-3(2H)-yl]propanamide |
| 172 | ChemDiv | C260-1235 | C29H27N5O5 | 525.56904 | 4-[2,4-dioxo-1-[(4-oxo-4H-pyrido[1,2-a]pyrimidin-2-yl)methyl]-1,4-dihydroquinazolin-3(2H)-yl]-N-(2-methoxybenzyl)butanamide |
| 173 | ChemDiv | C260-1244 | C30H29N5O5 | 539.59613 | N-(2-methoxybenzyl)-4-[1-[(6-methyl-4-oxo-4H-pyrido[1,2-a]pyrimidin-2-yl)methyl]-2,4-dioxo-1,4-dihydroquinazolin-3(2H)-yl]butanamide |
| 174 | ChemDiv | C260-1680 | C24H22FN3O4 | 435.45904 | 4-[1-(2-fluorobenzyl)-2,4-dioxo-1,4-dihydroquinazolin-3(2H)-yl]-N-(2-furylmethyl)butanamide |
| 175 | ChemDiv | C260-1990 | C26H21N3O6 | 471.47377 | N-(4-acetylphenyl)-2-[3-(1,3-benzodioxol-5-ylmethyl)-2,4-dioxo-3,4-dihydroquinazolin-1(2H)-yl]acetamide |
| 176 | ChemDiv | C260-3049 | C23H23BrN4O4 | 499.36816 | Multiplicative nomenclature is not supported in current version! |
| 177 | ChemDiv | C276-0235 | C22H27NO5 | 385.46419 | ethyl 6-(2,5-dimethoxyphenyl)-4-oxo-3-propyl-4,5,6,7-tetrahydro-1H-indole-2-carboxylate |
| 178 | ChemDiv | C276-0289 | C21H25NO4 | 355.4377 | 2-isopropoxyethyl 3-methyl-4-oxo-6-phenyl-4,5,6,7-tetrahydro-1H-indole-2-carboxylate |
| 179 | ChemDiv | C294-0457 | C30H31N3O5 | 513.59867 | N-(2,5-dimethoxybenzyl)-3-(1H-indol-3-yl)-2-(2-methoxyethyl)-1-oxo-1,2,3,4-tetrahydroisoquinoline-4-carboxamide |
| 180 | ChemDiv | C294-0634 | C27H27N3O3S | 473.59854 | 2-(2-methoxyethyl)-3-(1-methyl-1H-indol-3-yl)-1-oxo-N-(thien-2-ylmethyl)-1,2,3,4-tetrahydroisoquinoline-4-carboxamide |
| 181 | ChemDiv | C294-0693 | C31H33N3O5 | 527.62576 | N-(2,5-dimethoxybenzyl)-2-(2-methoxyethyl)-3-(1-methyl-1H-indol-3-yl)-1-oxo-1,2,3,4-tetrahydroisoquinoline-4-carboxamide |
| 182 | ChemDiv | C294-0708 | C31H33N3O4 | 511.62636 | N-(4-ethoxybenzyl)-2-(2-methoxyethyl)-3-(1-methyl-1H-indol-3-yl)-1-oxo-1,2,3,4-tetrahydroisoquinoline-4-carboxamide |
| 183 | ChemDiv | C358-0073 | C28H28N2O5 | 472.54576 | N-(4-ethoxyphenyl)-10,11-dimethoxy-8-oxo-5,8,13,13a-tetrahydro-6H-isoquino[3,2-a]isoquinoline-13-carboxamide |
| 184 | ChemDiv | C387-0015 | C23H21N3O4 | 403.44152 | 2-[(3,4-dimethoxyphenyl)amino]-N-(2-furylmethyl)quinoline-4-carboxamide |
| 185 | ChemDiv | C387-0156 | C23H27N3O3 | 393.48994 | N-(3-isopropoxypropyl)-2-[(4-methoxyphenyl)amino]quinoline-4-carboxamide |
| 186 | ChemDiv | C387-0265 | C25H28N4O4 | 448.52631 | 2-[(2,4-dimethoxyphenyl)amino]-N-[3-(2-oxopyrrolidin-1-yl)propyl]quinoline-4-carboxamide |
| 187 | ChemDiv | C387-0328 | C24H27N3O3 | 405.50109 | 4-(azepan-1-ylcarbonyl)-N-(2,4-dimethoxyphenyl)quinolin-2-amine |
| 188 | ChemDiv | C387-0352 | C26H29N3O5 | 463.53813 | ethyl 1-({2-[(2,4-dimethoxyphenyl)amino]quinolin-4-yl}carbonyl)piperidine-3-carboxylate |
| 189 | ChemDiv | C387-1226 | C22H25N3O4 | 395.46225 | 2-[(2,5-dimethoxyphenyl)amino]-N-(3-methoxypropyl)quinoline-4-carboxamide |
| 190 | ChemDiv | C387-1542 | C25H27N3O3S | 449.57624 | ethyl 1-[(2-{3-(methylthio)phenyl]amino}quinolin- |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| | | | | | 4-yl)carbonyl]piperidine-3-carboxylate |
| 191 | ChemDiv | C387-1571 | C26H32N4O2 | 432.57054 | 2-[(4-isopropylphenyl)amino]-N-(3-morpholin-4-ylpropyl)quinoline-4-carboxamide |
| 192 | ChemDiv | C387-1581 | C24H29N3O2 | 391.51763 | N-(3-ethoxypropyl)-2-[(4-isopropylphenyl)amino]quinoline-4-carboxamide |
| 193 | ChemDiv | C389-0285 | C24H30N2O4 | 410.5177 | N-[2-(3,4-diethoxyphenyl)ethyl]-4-methyl-3-(2-oxopyrrolidin-1-yl)benzamide |
| 194 | ChemDiv | C444-0317 | C17H28N2O2 | 292.42491 | 4-acetyl-N,N-dibutyl-3,5-dimethyl-1H-pyrrole-2-carboxamide |
| 195 | ChemDiv | C457-0275 | C18H19N3O2S | 341.43503 | N-(4-butylphenyl)-3-methyl-5-oxo-5H-[1,3]thiazolo[3,2-a]pyrimidine-6-carboxamide |
| 196 | ChemDiv | C470-0206 | C21H27ClN6O3 | 446.94074 | 7-(4-chlorobenzyl)-8-{[4-(2-hydroxyethyl)piperazin-1-yl]methyl}-1,3-dimethyl-3,7-dihydro-1H-purine-2,6-dione |
| 197 | ChemDiv | C470-0604 | C18H29N5O3 | 363.46353 | 8-[(3,5-dimethylpiperidin-1-yl)methyl]-7-(3-hydroxypropyl)-1,3-dimethyl-3,7-dihydro-1H-purine-2,6-dione |
| 198 | ChemDiv | C517-2632 | C21H24N4O4S | 428.51383 | N~2~-[(3,5-dimethyl-1H-pyrazol-4-yl)sulfonyl]-N~2~-(4-methoxyphenyl)-N~1~-(4-methylphenyl)glycinamide |
| 199 | ChemDiv | C547-0792 | C26H29N3O5 | 463.53813 | 4-{4-[4-(1,3-benzodioxol-5-ylmethyl)piperazin-1-yl]-4-oxobutoxy}-1-methylquinolin-2(1H)-one |
| 200 | ChemDiv | C610-0163 | C20H22N4O5S | 430.48614 | methyl 2-{[2-(4-methoxyphenyl)-6,8-dimethyl-5,7-dioxo-5,6,7,8-tetrahydropyrimido[4,5-d]pyrimidin-4-yl]thio}butanoate |
| 201 | ChemDiv | C692-0377 | C21H25ClN6O4 | 460.9242 | ethyl 4-{[7-(2-chlorobenzyl)-3-methyl-2,6-dioxo-2,3,6,7-tetrahydro-1H-purin-8-yl]methyl}piperazine-1-carboxylate |
| 202 | ChemDiv | C736-0606 | C21H24N6O2 | 392.46443 | 8,9-dimethoxy-N-(3-methylbutyl)-2-pyridin-3-yl[1,2,4]triazolo[1,5-c]quinazolin-5-amine |
| 203 | ChemDiv | K216-1622 | C25H19N3O3 | 409.44848 | 2,3-di-2-furyl-N-(2-phenylethyl)quinoxaline-6-carboxamide |
| 204 | ChemDiv | K221-3327 | C22H31N3O5 | 417.50947 | N-cycloheptyl-3-(6,7-diethoxy-2,4-dioxo-1,4-dihydroquinazolin-3(2H)-yl)propanamide |
| 205 | ChemDiv | K263-0500 | C24H24FN3O3S2 | 485.60358 | N-(4-fluorophenyl)-2-{[3-(3-isopropoxypropyl)-4-oxo-3,4-dihydro[1]benzothieno[3,2-d]pyrimidin-2-yl]thio}acetamide |
| 206 | ChemDiv | K279-0756 | C30H26N6O4S | 566.64352 | N-(4-methoxybenzyl)-3-(3-oxo-5-{[(4-oxo-4H-pyrido[1,2-a]pyrimidin-2-yl)methyl]thio}-2,3-dihydroimidazo[1,2-c]quinazolin-2-yl)propanamide |
| 207 | ChemDiv | K284-0633 | C26H23N3O5S | 489.55431 | 2-{[3-(1,3-benzodioxol-5-ylmethyl)-4-oxo-3,4-dihydroquinazolin-2-yl]thio}-N-(4-ethoxyphenyl)acetamide |
| 208 | ChemDiv | K402-0190 | C21H19N5O3 | 389.41728 | ethyl 4-{[1-(4-methoxyphenyl)-1H-pyrazolo[3,4-d]pyrimidin-4-yl]amino}benzoate |
| 209 | ChemDiv | K402-0349 | C21H21N5O2 | 375.43382 | N-(2,4-dimethoxyphenyl)-1-(2,4-dimethylphenyl)-1H-pyrazolo[3,4-d]pyrimidin-4-amine |
| 210 | ChemDiv | K405-0017 | C24H26N4O | 386.50102 | N-(3-isopropoxypropyl)-5,7-diphenyl-7H-pyrrolo[2,3-d]pyrimidin-4-amine |
| 211 | ChemDiv | K405-0080 | C22H21ClN4O2 | 408.89127 | 2-(2-{[7-(4-chlorophenyl)-5-phenyl-7H-pyrrolo[2,3-d]pyrimidin-4-yl]amino}ethoxy)ethanol |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 212 | ChemDiv | K405-0190 | C23H24N4O2 | 388.47333 | 2-(2-{[7-(3-methylphenyl)-5-phenyl-7H-pyrrolo[2,3-d]pyrimidin-4-yl]amino}ethoxy)ethanol |
| 213 | ChemDiv | K405-0202 | C26H27N5O | 425.53799 | 1-(3-{[7-(3-methylphenyl)-5-phenyl-7H-pyrrolo[2,3-d]pyrimidin-4-yl]amino}propyl)pyrrolidin-2-one |
| 214 | ChemDiv | K407-0099 | C28H31NO7 | 493.56177 | 2-(3,4-dimethoxybenzoyl)-6,7-dimethoxy-1-[(2-methoxyphenoxy)methyl]-1,2,3,4-tetrahydroisoquinoline |
| 215 | ChemDiv | K407-0271 | C26H26N2O6 | 462.50692 | 6,7-dimethoxy-1-[(4-nitrophenoxy)methyl]-2-(phenylacetyl)-1,2,3,4-tetrahydroisoquinoline |
| 216 | ChemDiv | K407-0274 | C28H29NO6 | 475.54643 | methyl 4-{[6,7-dimethoxy-2-(phenylacetyl)-1,2,3,4-tetrahydroisoquinolin-1-yl]methoxy}benzoate |
| 217 | ChemDiv | K407-0333 | C28H31NO6 | 477.56237 | 6,7-dimethoxy-1-[(4-methoxyphenoxy)methyl]-2-(2-phenoxypropanoyl)-1,2,3,4-tetrahydroisoquinoline |
| 218 | ChemDiv | K412-0053 | C22H21N5O3S3 | 499.63637 | 2-({2-[5-(4-methoxyphenyl)-3-thien-2-yl-4,5-dihydro-1H-pyrazol-1-yl]-2-oxoethyl}thio)-6,7-dihydro[1,3,4]thiadiazolo[3,2-a][1,3]diazepin-8(5H)-one |
| 219 | ChemDiv | K617 0168 | C31H33N3O7 | 559.62456 | 4-methoxy-N-[(Z)-1-[(8-oxo-1,5,6,8-tetrahydro-2H-1,5-methanopyrido[1,2-a][1,5]diazocin-3(4H)-yl)carbonyl]-2-(3,4,5-trimethoxyphenyl)vinyl]benzamide |
| 220 | ChemDiv | K781-0094 | C19H22N2O6 | 374.39699 | ethyl 4-{[2-(3,4-dimethoxyphenyl)ethyl]amino}-3-nitrobenzoate |
| 221 | ChemDiv | K781-3613 | C25H27N3O2S | 433.57684 | 2-({2-[(4-isopropylphenyl)amino]-2-oxoethyl}thio)-N-(4-methylbenzyl)nicotinamide |
| 222 | ChemDiv | K784-5891 | C24H34N2O4 | 414.54958 | 4-cyclopentyl-3-(3,4-dimethoxyphenyl)-1-(4-methylcyclohexyl)piperazine-2,5-dione |
| 223 | ChemDiv | K784-7016 | C23H30N4O3 | 410.52055 | methyl 2-(4-butoxyphenyl)-3-(cyclohexylamino)-1H-imidazo[1,2-b]pyrazole-7-carboxylate |
| 224 | ChemDiv | K784-7165 | C24H28N2O3 | 392.50236 | 4-cyclopentyl-3-(4-methoxyphenyl)-1-(2-phenylethyl)piperazine-2,5-dione |
| 225 | ChemDiv | K786-2097 | C26H26N2O4 | 430.50812 | 2-benzyl-N-[2-(3,4-dimethoxyphenyl)ethyl]-3-oxoisoindoline-1-carboxamide |
| 226 | ChemDiv | K786-3679 | C19H18BrClN2O4 | 453.72331 | N-(5-bromo-2-methoxybenzyl)-2-(6-chloro-3-oxo-2,3-dihydro-4H-1,4-benzoxazin-4-yl)propanamide |
| 227 | ChemDiv | K786-6361 | C19H24N2O5 | 360.41353 | ethyl 1-[3-(3-oxo-2,3-dihydro-4H-1,4-benzoxazin-4-yl)propanoyl]piperidine-3-carboxylate |
| 228 | ChemDiv | K786-6722 | C20H22N2O5 | 370.40874 | N-(4-ethoxy-3-methoxybenzyl)-2-(3-oxo-2,3-dihydro-4H-1,4-benzoxazin-4-yl)acetamide |
| 229 | ChemDiv | K788-3854 | C28H28N4O3S | 500.62436 | N-[4-(dimethylamino)phenyl]-2-[11-oxo-8-(pyrrolidin-1-ylcarbonyl)dibenzo[b,f][1,4]thiazepin-10(11H)-yl]acetamide |
| 230 | ChemDiv | K788-3874 | C28H27N3O4S | 501.60909 | N-(4-ethoxyphenyl)-2-[11-oxo-8-(pyrrolidin-1-ylcarbonyl)dibenzo[b,f][1,4]thiazepin-10(11H)-yl]acetamide |
| 231 | ChemDiv | K788-3891 | C28H27N3O3S | 485.60969 | N-(4-ethylphenyl)-2-[11-oxo-8-(pyrrolidin-1-ylcarbonyl)dibenzo[b,f][1,4]thiazepin-10(11H)-yl]acetamide |
| 232 | ChemDiv | K788-4908 | C30H30N4O5 | 526.5974 | 4-{[4-(1,3-benzodioxol-5-ylmethyl)piperazin-1-yl]carbonyl}- |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 233 | ChemDiv | K788-4912 | C26H25N3O4 | 443.50685 | N-(2,4-dimethoxyphenyl)quinolin-2-amine 2-[(2,4-dimethoxyphenyl)amino]-N-(2-methoxybenzyl)quinoline-4-carboxamide |
| 234 | ChemDiv | K788-6626 | C28H27N3O6S | 533.60789 | N-(2,4-dimethoxyphenyl)-2-[8-(morpholin-4-ylcarbonyl)-11-oxodibenzo[b,f][1,4]thiazepin-10(11H)-yl]acetamide |
| 235 | ChemDiv | K788-6627 | C29H29N3O4S | 515.63618 | N-(4-isopropylphenyl)-2-[8-(morpholin-4-ylcarbonyl)-11-oxodibenzo[b,f][1,4]thiazepin-10(11H)-yl]acetamide |
| 236 | ChemDiv | K824-0044 | C19H18FN3O4S | 403.43541 | ethyl 4-[(2-fluorophenyl)amino]-2-(2-methoxy-2-oxoethyl)-5-methylthieno[2,3-d]pyrimidine-6-carboxylate |
| 237 | ChemDiv | K824-0098 | C17H23N3O4S | 365.45456 | ethyl 4-(butylamino)-2-(2-methoxy-2-oxoethyl)-5-methylthieno[2,3-d]pyrimidine-6-carboxylate |
| 238 | ChemDiv | K832-0411 | C20H23N5O3 | 381.43801 | 5-(4-methylphenyl)-7-(2,3,4-trimethoxyphenyl)-4,5,6,7-tetrahydrotetrazolo[1,5-a]pyrimidine |
| 239 | ChemDiv | K832-0886 | C19H20BrN5O3 | 446.30695 | 5-(4-bromophenyl)-7-(2,3,4-trimethoxyphenyl)-4,5,6,7-tetrahydrotetrazolo[1,5-a]pyrimidine |
| 240 | ChemDiv | K832-2851 | C21H22N4O3 | 378.43449 | 7-(2,5-dimethoxyphenyl)-5-(4-ethoxyphenyl)-4,7-dihydro[1,2,4]triazolo[1,5-a]pyrimidine |
| 241 | ChemDiv | K832-2919 | C21H24N4O2 | 364.45103 | 7-(2,5-dimethoxyphenyl)-5-(4-ethylphenyl)-4,5,6,7-tetrahydro[1,2,4]triazolo[1,5-a]pyrimidine |
| 242 | ChemDiv | K832-2942 | C20H23N5O2 | 365.43861 | 7-(2,5-dimethoxyphenyl)-5-(4-ethylphenyl)-4,5,6,7-tetrahydrotetrazolo[1,5-a]pyrimidine |
| 243 | ChemDiv | K837-0595 | C25H26ClNO5 | 455.94267 | diethyl 4-(3-chlorophenyl)-1-(4-methoxybenzyl)-1,4-dihydropyridine-3,5-dicarboxylate |
| 244 | ChemDiv | R052-1612 | C16H15F3N2O3S | 372.36875 | ethyl 2-amino-4-methyl-5-({[2-(trifluoromethyl)phenyl]amino}carbonyl)thiophene-3-carboxylate |
| 245 | Maybridge | SPB 04150 | C20H17ClN2O4S | 416.88649 | 1-(4-chlorophenyl)-2-{[4-hydroxy-5-(4-methoxyphenoxy)-6-methylpyrimidin-2-yl]thio}ethan-1-one |
| 246 | Maybridge | JP 00593 | C19H21FN2O5S | 408.45202 | ethyl 3-{[(4-fluorophenyl)sulfonyl]amino}-4-morpholinobenzoate |
| 247 | Maybridge | BTB 07353 | C28H28F6O6S2 | 638.65016 | 2,5-di(tert-butyl)-4-({[4-(trifluoromethyl)phenyl]sulfonyl}oxy)phenyl 4-(trifluoromethyl)benzene-1-sulfonate |
| 248 | Maybridge | SPB 04151 | C21H20N2O5S | 412.46795 | 2-{[4-hydroxy-5-(4-methoxyphenoxy)-6-methylpyrimidin-2-yl]thio}-1-(4-methoxyphenyl)ethan-1-one |
| 249 | Maybridge | RJC 00532 | C16H14N2O5 | 314.30038 | Ethyl 3-hydroxy-5-methyl-6-oxo-1-phenyl-1,6-dihydropyrano[2,3-c]pyrazole-4-carboxylate |
| 250 | Maybridge | SCR 00426 | C19H21ClN2O4S | 408.90722 | 1-(1,3-benzodioxol-5-ylmethyl)-4-[(4-chlorobenzyl)sulfonyl]piperazine |
| 251 | Maybridge | RJC 03582 | C22H23NO2 | 333.43411 | 1-benzyl-3-butyl-4-hydroxy-6-phenylpyridin-2(1H)-one |
| 252 | Maybridge | HTS 03876 | C18H18N2OS | 310.42096 | N'-(4-isopropylphenyl)-1-benzothiophene-2-carbohydrazide |
| 253 | Maybridge | RJF 00063 | C16H21N3O4 | 319.36347 | ethyl 5-[4-(2-methoxyethoxy)anilino]-3-methyl-1H-pyrazole-4-carboxylate |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 254 | Maybridge | CD 02465 | C26H22ClN3O4S | 507.99994 | 2-({5-[({[3-(2-chlorophenyl)-5-methylisoxazol-4-yl]carbonyl}oxy)ethanimidoyl]-2-methoxybenzyl}thio)pyridine |
| 255 | Maybridge | HTS 09625 | C24H18N2O3S | 414.48666 | [2-(2,3-dihydro-1,4-benzodioxin-6-ylamino)-4-phenyl-1,3-thiazol-5-yl](phenyl)methanone |
| 256 | Maybridge | HTS 04710 | C21H16F3N3OS2 | 447.50437 | 2-(1,3-benzothiazol-2-ylsulfanyl)-1-[1-(trifluoromethyl)-1,3,4,9-tetrahydro-2H-beta-carbolin-2-yl]-1-ethanone |
| 257 | Maybridge | HTS 10133 | C24H17FN2O3S | 432.47709 | [2-(2,3-dihydro-1,4-benzodioxin-6-ylamino)-4-phenyl-1,3-thiazol-5-yl](4-fluorophenyl)methanone |
| 258 | Maybridge | GK 02954 | C17H18F3N3O2 | 353.34711 | |
| 259 | Maybridge | S 06468 | C12H11N5O4S | 321.31657 | ethyl 6-methyl-3-(5-nitro-2-thienyl)-1H-pyrazolo[5,1-c][1,2,4]triazole-7-carboxylate, 80 < 90% |
| 260 | Maybridge | RH 00944 | C18H18F3N3O5 | 413.35646 | diethyl 2-({2-methyl-4-[5-(trifluoromethyl)-1,3,4-oxadiazol-2-yl]anilino}methylidene)malonate |
| 261 | Maybridge | GK 02097 | C20H18F3N3O3 | 405.37996 | 2-furylmethyl 2-(4-isopropylanilino)-4-(trifluoromethyl)pyrimidine-5-carboxylate |
| 262 | Chembridge | 5136148 | C23H29NO5 | 399.49128 | 4-(3,5-dimethoxyphenyl)-2,7,7-trimethyl-5-oxo-1,4,5,6,7,8-hexahydro-3-quinolinecarboxylate |
| 263 | Chembridge | 5237650 | C24H25NO3 | 375.47175 | N-[2-(3,4-dimethoxyphenyl)ethyl]-2,2-diphenylacetamide |
| 264 | Chembridge | 5274702 | C20H25NO5 | 359.42595 | 3-butyryl-4-{[2-(3,4-dimethoxyphenyl)ethyl]amino}-6-methyl-2H-pyran-2-one |
| 265 | Chembridge | 5397470 | C22H28N2O6 | 416.47826 | 4-{[4-(3,5-dimethoxybenzoyl)-1-piperazinyl]methyl}-2,6-dimethoxyphenol |
| 266 | Chembridge | 5454616 | C17H19NO5 | 317.34468 | 1,3-benzodioxol-5-yl(2,3,4-trimethoxybenzyl)amine |
| 267 | Chembridge | 5469236 | C15H19NO4 | 277.32298 | ethyl 6-[(dimethylamino)methyl]-5-hydroxy-2-methyl-1-benzofuran-3-carboxylate |
| 268 | Chembridge | 5532093 | C24H27NO3 | 377.48769 | (1,2-diphenylethyl)(2,3,4-trimethoxybenzyl)amine |
| 269 | Chembridge | 5561979 | C23H24N2O4S | 424.52273 | N-(2-methoxyethyl)-4-{[phenyl(phenylsulfonyl)amino]methyl}benzamide |
| 270 | Chembridge | 5575070 | C22H21ClN2O4S | 444.94067 | N'-(4-chloro-2-methylphenyl)-N$^2$-(4-methoxyphenyl)-N$^2$-(phenylsulfonyl)glycinamide |
| 271 | Chembridge | 5615299 | C25H25ClO6 | 456.9274 | 2-[6-(2-chlorobenzoyl)-3,4-dimethoxy-2,4-cyclohexadien-1-yl]-1-(3,4-dimethoxyphenyl)ethanone |
| 272 | Chembridge | 5664540 | C21H24N2O4 | 368.43643 | 1-(4-ethoxyphenyl)-3-{[2-(4-methoxyphenyl)ethyl]amino}-2,5-pyrrolidinedione |
| 273 | Chembridge | 5807980 | C23H22N2O3 | 374.44339 | (1-benzyl-1H-benzimidazol-2-yl)(3,4-dimethoxyphenyl)methanol |
| 274 | Chembridge | 5837287 | C18H18Cl2N2O3 | 381.26176 | N-(4-{[2-(2,4-dichlorophenoxy)acetyl]amino}phenyl)butanamide |
| 275 | Chembridge | 5844263 | C20H24N2O3 | 340.42588 | N-(4-{[2-(3,4-dimethylphenoxy)acetyl]amino}phenyl)butanamide |
| 276 | Chembridge | 5848239 | C20H28N2O3 | 344.45776 | 1-(3-cyclopentylpropanoyl)-4-(3-methoxybenzoyl)piperazine |
| 277 | Chembridge | 5848275 | C19H22N2O3 | 326.39879 | N-(4-{[2-(2,4-dimethylphenoxy)acetyl]amino}phenyl)propanamide |
| 278 | Chembridge | 5883990 | C22H30N2O4 | 386.4954 | 1-(4-methoxybenzyl)-4-(2,4,5-trimethoxybenzyl)piperazine |
| 279 | Chembridge | 5916567 | C25H29N3O2 | 403.52878 | 3-benzyl-5,5-diethyl-2-[(2-hydroxyethyl)amino]-5,6-dihydrobenzo[h]quinazolin-4(3H)-one |
| 280 | Chembridge | 5931427 | C21H22BrFN2O4 | 465.32289 | ethyl 4-[4-(3-bromo-4-methoxybenzoyl)-2-fluorophenyl]-1-piperazinecarboxylate |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 281 | Chembridge | 5936409 | C18H30N2O2 | 306.452 | 4-{2-[(4-methoxybenzyl)amino]ethyl}-1,2,5-trimethyl-4-piperidinol |
| 282 | Chembridge | 5950114 | C27H24ClN3O3S | 506.02763 | 4-{[(5-chloro-2-methylphenyl)(phenylsulfonyl)amino]methyl}-N-(2-pyridinylmethyl)benzamide |
| 283 | Chembridge | 5954963 | C26H27ClN2O4S | 499.03309 | 4-{[(5-chloro-2-methylphenyl)(phenylsulfonyl)amino]methyl}-N-(tetrahydro-2-furanylmethyl)benzamide |
| 284 | Chembridge | 5955255 | C27H24ClN3O3S | 506.02763 | 4-{[(5-chloro-2-methylphenyl)(phenylsulfonyl)amino]methyl}-N-(3-pyridinylmethyl)benzamide |
| 285 | Chembridge | 5997558 | C23H32N2O6 | 432.52129 | 2,6-dimethoxy-4-{[4-(2,3,4-trimethoxybenzyl)-1-piperazinyl]methyl}phenol ethanedioate (salt) |
| 286 | Chembridge | 6009310 | C19H21N3O3 | 339.39752 | 3-ethyl-1-[(4-methoxyphenyl)acetyl]-5-(4-pyridinyl)-4,5-dihydro-1H-pyrazol-5-ol |
| 287 | Chembridge | 6047903 | C16H15F3N2O3S | 372.36875 | ethyl 2-amino-4-methyl-5-({[2-(trifluoromethyl)phenyl]amino}carbonyl)-3-thiophenecarboxylate |
| 288 | Chembridge | 6051034 | C18H20N2O4 | 328.3711 | methyl 4-{[(3,5-dioxo-4-azatricyclo[5.2.1.0$^{2,6}$]dec-4-yl)methyl]amino}benzoate |
| 289 | Chembridge | 6065252 | C24H23NO3 | 373.45581 | N-[bis(4-methoxyphenyl)methyl]-3-phenylacrylamide |
| 290 | Chembridge | 6073261 | C26H27N3O2 | 413.52399 | N-{2-[(4-benzyl-1-piperazinyl)carbonyl]phenyl}-2-methylbenzamide |
| 291 | Chembridge | 6075947 | C25H26N2O4S | 450.56097 | N-(2-ethoxyphenyl)-2-{[(4-methoxyphenyl)acetyl]amino}-5,6-dihydro-4H-cyclopenta[b]thiophene-3-carboxamide |
| 292 | Chembridge | 6076669 | C19H19ClN2O3 | 358.82788 | 5-(4-chlorophenyl)-1-[(4-methoxyphenyl)acetyl]-3-methyl-4,5-dihydro-1H-pyrazol-5-ol |
| 293 | Chembridge | 6077558 | C24H25ClN2O4S | 472.99485 | 4-({(3-chlorophenyl)[(4-methylphenyl)sulfonyl]amino}methyl)-N-(2-methoxyethyl)benzamide |
| 294 | Chembridge | 6132356 | C20H19NO4 | 337.37873 | 2-(2,4-diethoxyphenyl)-4-quinolinecarboxylic acid |
| 295 | Chembridge | 6144063 | C21H20ClNO | 337.85265 | 2-(benzylamino)-1-(4-chlorophenyl)-1-phenylethanol |
| 296 | Chembridge | 6166020 | C23H23NO4 | 377.44406 | N-benzyl-2-hydroxy-2,2-bis(4-methoxyphenyl)acetamide |
| 297 | Chembridge | 6197905 | C21H22N2O4 | 366.42049 | ethyl 4-[(4-methoxyphenyl)amino]-2-methyl-5-oxo-1-phenyl-2,5-dihydro-1H-pyrrole-2-carboxylate |
| 298 | Chembridge | 6237955 | C19H24O6 | 348.39953 | 2-methoxyethyl 5-(3,3-dimethyl-2-oxobutoxy)-2-methyl-1-benzofuran-3-carboxylate |
| 299 | Chembridge | 6239693 | C19H32ClNO4 | 373.92419 | 1-[2-hydroxy-3-(3-methoxyphenoxy)propyl]-2,2,6,6-tetramethyl-4-piperidinol hydrochloride |
| 300 | Chembridge | 6398556 | C20H26N2O3S | 374.50582 | 5-{2-[(4-ethoxyphenyl)amino]-1,3-thiazol-4-yl}-3-isobutyl-5-methyldihydro-2(3H)-furanone |
| 301 | Chembridge | 6517002 | C23H19Cl2N3O2 | 440.33278 | ethyl 3-{[2-(2-chlorophenyl)-4-quinazolinyl]amino}benzoate |
| 302 | Chembridge | 6539631 | C19H28N2O5 | 364.44541 | ethyl 1-{3-[(2,5-dimethoxyphenyl)amino]-3-oxopropyl}-4-piperidinecarboxylate hydrochloride |
| 303 | Chembridge | 6559617 | C18H26N2O4 | 334.41892 | ethyl 1-{3-[(2-methoxyphenyl)amino]-3-oxopropyl}-4-piperidinecarboxylate |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 304 | Chembridge | 6568495 | C20H34N2O2 | 334.50618 | 4-{2-[(4-isopropoxybenzyl)amino]ethyl}-1,2,5-trimethyl-4-piperidinol |
| 305 | Chembridge | 6579234 | C27H37N3O3 | 451.61424 | 1-{[1-(4-ethoxybenzyl)-4-piperidinyl]carbonyl}-4-(2-ethoxyphenyl)piperazine oxalate |
| 306 | Chembridge | 6606368 | C13H16N2O3S | 280.34807 | ethyl 4-{[(propionylamino)carbonothioyl]amino}benzoate |
| 307 | Chembridge | 6624938 | C26H29NO5S | 467.58873 | 2-ethoxyethyl 4-(4-methoxyphenyl)-2-methyl-5-oxo-7-(2-thienyl)-1,4,5,6,7,8-hexahydro-3-quinolinecarboxylate |
| 308 | Chembridge | 6690798 | C21H24N2O5S | 416.49983 | 3-hydroxy-5-(5-methyl-2-furyl)-1-[3-(4-morpholinyl)propyl]-4-(2-thienylcarbonyl)-1,5-dihydro-2H-pyrrol-2-one |
| 309 | Chembridge | 6719665 | C18H20N2O3 | 312.3717 | N-[2-(acetylamino)phenyl]-2-(2,5-dimethylphenoxy)acetamide |
| 310 | Chembridge | 6893126 | C24H21NO5 | 403.43867 | 4-{2-[2-(4-methoxyphenyl)-2-oxoethoxy]phenyl}-4-azatricyclo[5.2.1.0$^{2,6}$]dec-8-ene-3,5-dione |
| 311 | Chembridge | 6940504 | C25H30N2O5 | 438.52825 | 1-[2-(dimethylamino)ethyl]-5-(2-ethoxyphenyl)-3-hydroxy-4-(4-methoxy-3-methylbenzoyl)-1,5-dihydro-2H-pyrrol-2-one |
| 312 | Chembridge | 6948667 | C27H29NO4 | 431.53648 | N-[3-(1,3-benzodioxol-5-yl)-3-(2-methoxyphenyl)propyl]-N-benzylpropanamide |
| 313 | Chembridge | 6949401 | C22H21ClN2O3 | 396.87727 | 2-[1-(4-chlorobenzoyl)-5-methoxy-2-methyl-1H-indol-3-yl]-N-cyclopropylacetamide |
| 314 | Chembridge | 6963276 | C19H20Cl2N2O | 363.29005 | 6-chloro-2-methyl-N-(4-propoxyphenyl)-4-quinolinamine hydrochloride |
| 315 | Chembridge | 6963648 | C24H22N2O3S | 418.51854 | 2-[(2-cyanophenyl)thio]-N-[2-(3,4-dimethoxyphenyl)ethyl]benzamide |
| 316 | Chembridge | 7004747 | C25H25N3O3 | 415.4963 | 7-[(4-ethoxy-3-methoxyphenyl)(2-pyridinylamino)methyl]-2-methyl-8-quinolinol |
| 317 | Chembridge | 7111754 | C22H22O6 | 382.41704 | Methyl {7-[(3-methoxybenzyl)oxy]-4,8-dimethyl-2-oxo-2H-chromen-3-yl}acetate |
| 318 | Chembridge | 7170542 | C24H21NO3 | 371.43987 | N-(3-acetylphenyl)-3-(4-methoxyphenyl)-2-phenylacrylamide |
| 319 | Chembridge | 7192079 | C22H25N3O4 | 395.46225 | 4-(2,4-dimethoxyphenyl)-N-(2,5-dimethylphenyl)-6-methyl-2-oxo-1,2,3,4-tetrahydro-5-pyrimidinecarboxamide |
| 320 | Chembridge | 7196183 | C15H21N5O | 287.36752 | N$^4$-(3-methoxyphenyl)-1,3,5-triazaspiro[5.5]undeca-1,3-diene-2,4-diamine |
| 321 | Chembridge | 7303602 | C23H23N3O5 | 421.45686 | 2-{2-[4-(1,3-benzodioxol-5-ylmethyl)-1-piperazinyl]-1-methyl-2-oxoethyl}-1H-isoindole-1,3(2H)-dione |
| 322 | Chembridge | 7313366 | C26H23ClN2O5 | 478.93661 | N-(4-chloro-2,5-dimethoxyphenyl)-2-(2,4-dimethoxyphenyl)-4-quinolinecarboxamide |
| 323 | Chembridge | 7329511 | C19H21ClN2O3 | 360.84382 | N-(4-{[(4-chloro-3-methylphenoxy)acetyl]amino}phenyl)-2-methylpropanamide |
| 324 | Chembridge | 7370007 | C20H18O6 | 354.36286 | ethyl 7-methoxy-3-(2-methoxyphenyl)-4-oxo-4H-chromene-2-carboxylate |
| 325 | Chembridge | 7383785 | C21H21N5O3 | 391.43322 | 1-(3-methylphenyl)-N-(3,4,5-trimethoxyphenyl)-1H-pyrazolo[3,4-d]pyrimidin-4-amine |
| 326 | Chembridge | 7390308 | C21H25N3O3 | 367.4517 | N-(tert-butyl)-2-{[4-(propionylamino)benzoyl]amino}benzamide |
| 327 | Chembridge | 7482541 | C19H22N2O4 | 342.39819 | N-[2-(butyrylamino)phenyl]-2,4-dimethoxybenzamide |
| 328 | Chembridge | 7490085 | C23H23N3O4 | 405.45746 | 4-(2,5-dimethylbenzoyl)-5-(2-furyl)-3-hydroxy-1-[3-(1H-imidazol-1- |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| | | | | | yl)propyl]-1,5-dihydro-2H-pyrrol-2-one |
| 329 | Chembridge | 7501087 | C21H22N4O3S | 410.49849 | ethyl 4-({[(4-ethyl-5-phenyl-4H-1,2,4-triazol-3-yl)thio]acetyl}amino)benzoate |
| 330 | Chembridge | 7534689 | C20H18ClF3N4O2S | 470.90426 | N-[2-chloro-5-(trifluoromethyl)phenyl]-2-{[5-(4-methoxybenzyl)-4-methyl-4H-1,2,4-triazol-3-yl]thio}acetamide |
| 331 | Chembridge | 7543525 | C22H24N2O3S | 396.51218 | N-{2-[(2-methoxyphenyl)amino]-2-phenylethyl}-4-methylbenzenesulfonamide |
| 332 | Chembridge | 7568257 | C23H21NO4 | 375.42812 | benzyl 3-benzyl-4-oxo-10-oxa-3-azatricyclo[5.2.1.0$^{1,5}$]dec-8-ene-6-carboxylate |
| 333 | Chembridge | 7584855 | C27H32N2O5S | 496.63049 | N$^2$-[(3,4-dimethoxyphenyl)sulfonyl]-N$^2$-(3,5-dimethylphenyl)-N$^1$-mesitylglycinamide |
| 334 | Chembridge | 7630860 | C21H27NO6 | 389.45244 | dimethyl 1-butyl-4-(2,4-dimethoxyphenyl)-1,4-dihydro-3,5-pyridinedicarboxylate |
| 335 | Chembridge | 7649230 | C24H20N2O4S | 432.502 | 3-hydroxy-4-[(2-methyl-2,3-dihydro-1-benzofuran-5-yl)carbonyl]-1-(3-pyridinylmethyl)-5-(2-thienyl)-1,5-dihydro-2H-pyrrol-2-one |
| 336 | Chembridge | 7653646 | C21H25BrN2O4 | 449.3484 | N-(4-{[(2-bromo-4,6-dimethylphenoxy)acetyl]amino}-2-methoxyphenyl)-2-methylpropanamide |
| 337 | Chembridge | 7655251 | C29H22ClFN2O3 | 500.96169 | 2-amino-4-{3-[(2-chloro-6-fluorobenzyl)oxy]phenyl}-5-oxo-7-phenyl-5,6,7,8-tetrahydro-4H-chromene-3-carbonitrile |
| 338 | Chembridge | 7656312 | C19H25N3O3S | 375.4934 | ethyl {[5-cyano-3,3-dimethyl-8-(1-pyrrolidinyl)-3,4-dihydro-1H-pyrano[3,4-c]pyridin-6-yl]thio}acetate |
| 339 | Chembridge | 7662629 | C23H24F3N5O2S | 491.53923 | N-(2-methyl-1-{4-methyl-5-[(2-oxo-2-{[3-(trifluoromethyl)phenyl]amino}ethyl)thio]-4H-1,2,4-triazol-3-yl}propyl)benzamide |
| 340 | Chembridge | 7665893 | C20H19ClN4O3S | 430.91643 | ethyl 4-[({[5-(4-chlorophenyl)-4-methyl-4H-1,2,4-triazol-3-yl]thio}acetyl)amino]benzoate |
| 341 | Chembridge | 7670127 | C21H25ClN2O4 | 404.8974 | N-(4-{[(4-chloro-3,5-dimethylphenoxy)acetyl]amino}-2-methoxyphenyl)-2-methylpropanamide |
| 342 | Chembridge | 7673541 | C15H31NO3 | 273.41922 | 1-(2-hydroxy-3-isopropoxypropyl)-2,2,6,6-tetramethyl-4-piperidinol |
| 343 | Chembridge | 7677946 | C19H19ClN4O2 | 370.84188 | 5-(4-chlorophenyl)-7-(3,4-dimethoxyphenyl)-4,5,6,7-tetrahydro[1,2,4]triazolo[1,5-a]pyrimidine |
| 344 | Chembridge | 7678233 | C18H26N6 | 326.44812 | 6-(1-azepanylmethyl)-N-(2,4-dimethylphenyl)-1,3,5-triazine-2,4-diamine |
| 345 | Chembridge | 7689705 | C23H26ClN5O2S | 472.01297 | N-{1-[5-({2-[(3-chloro-4-methylphenyl)amino]-2-oxoethyl}thio)-4-ethyl-4H-1,2,4-triazol-3-yl]ethyl}-2-methylbenzamide |
| 346 | Chembridge | 7714700 | C18H20N2O | 280.3729 | 1-(2-biphenylylcarbonyl)-4-methylpiperazine |
| 347 | Chembridge | 7715697 | C27H25NO5 | 443.504 | benzyl 7-(2-furyl)-2-methyl-4-(5-methyl-2-furyl)-5-oxo-1,4,5,6,7,8-hexahydro-3-quinolinecarboxylate |
| 348 | Chembridge | 7723636 | C24H17FN2O5 | 432.41189 | 4-(1,3-benzodioxol-5-ylcarbonyl)-5-(3-fluorophenyl)-3-hydroxy-1-(3-pyridinylmethyl)-1,5-dihydro-2H-pyrrol-2-one |

TABLE 1-continued

Chemical compounds identified by E47-ID1 interaction mapping as potentially inhibiting E47-Id1 interaction.

| Compound | Vendor | ID | Formula | MW | CHEMICAL NAME |
|---|---|---|---|---|---|
| 349 | Chembridge | 7726611 | C19H20N2O3S | 356.44685 | N-(6-propoxy-1,3-benzothiazol-2-yl)-2,3,3a,7a-tetrahydro-1-benzofuran-2-carboxamide |
| 350 | Chembridge | 7728025 | C17H20N2O3 | 300.36055 | 2-(3-acetyl-1H-indol-1-yl)-N-(tetrahydro-2-furanylmethyl)acetamide |
| 351 | Chembridge | 7729039 | C25H25F3N2O5S | 522.5476 | $N^2$-[(3,4-dimethoxyphenyl)sulfonyl]-$N^2$-(3,5-dimethylphenyl)-$N^1$-[2-(trifluoromethyl)phenyl]glycinamide |
| 352 | Chembridge | 7744840 | C24H23ClN2O6 | 470.91371 | 4-(1,3-benzodioxol-5-ylcarbonyl)-5-(3-chlorophenyl)-3-hydroxy-1-[2-(4-morpholinyl)ethyl]-1,5-dihydro-2H-pyrrol-2-one |
| 353 | Chembridge | 7770069 | C21H18N2O4S | 394.45261 | methyl 4-({phenyl[(phenylsulfonyl)imino]methyl}amino)benzoate |
| 354 | Chembridge | 7782335 | C20H22Cl2N2O4 | 425.31534 | 2-(2,4-dichlorophenoxy)-N-[4-(isobutyrylamino)-3-methoxyphenyl]propanamide |
| 355 | Chembridge | 7784009 | C23H18FNO4S | 423.46661 | 3-{3-[(4-fluorobenzyl)oxy]-4-methoxyphenyl}-2-(phenylsulfonyl)acrylonitrile |
| 356 | Chembridge | 7817032 | C21H21ClN4O3S | 444.94352 | ethyl 4-[({[5-(3-chlorophenyl)-4-ethyl-4H-1,2,4-triazol-3-yl]thio}acetyl)amino]benzoate |
| 357 | Chembridge | 7845520 | C23H24FN3O3 | 409.46443 | ethyl 1-{[3-(4-fluorophenyl)-4-oxo-3,4-dihydro-2-quinazolinyl]methyl}-4-piperidinecarboxylate |
| 358 | Chembridge | 7852329 | C18H22N2O4S2 | 394.51504 | $N^2$-(3-methoxyphenyl)-$N^2$-(methylsulfonyl)-$N^1$-[2-(phenylthio)ethyl]glycinamide |
| 359 | Chembridge | 7853369 | C23H17NO3 | 355.39684 | N-(2-oxo-2H-chromen-6-yl)-2,2-diphenylacetamide |
| 360 | Chembridge | 7853558 | C24H17NO5 | 399.40679 | 4-benzoyl-2-methylphenyl (1,3-dioxo-1,3-dihydro-2H-isoindol-2-yl)acetate |
| 361 | Chembridge | 7875496 | C19H20N4O3S2 | 416.52425 | ethyl 4-[({[4-ethyl-5-(2-thienyl)-4H-1,2,4-triazol-3-yl]thio}acetyl)amino]benzoate |
| 362 | Chembridge | 7877880 | C23H24N2O5 | 408.45813 | 2-hydroxy-2,2-bis(3-methoxyphenyl)-N'-(4-methoxyphenyl)acetohydrazide |
| 363 | Chembridge | 7908155 | C22H28N2O2 | 352.48066 | 3-[(2-ethylbutanoyl)amino]-N-(2-isopropylphenyl)benzamide |
| 364 | Chembridge | 7918425 | C21H29N3O4S | 419.54698 | ethyl 4-{[5-cyano-3,3-dimethyl-8-(4-morpholinyl)-3,4-dihydro-1H-pyrano[3,4-c]pyridin-6-yl]thio}butanoate |

Example II

Design of Synthetic Peptides

The E47 molecule from an X-ray of the structure of an E47-Id1 heterodimer was used as a template for peptide design. The peptides were designed to form leucine-zipper type dimers with Id1 (but not with E47), which could be stabilized by introduction of polar or charged side chains forming inter-molecular H-bonds and salt bridges with Id1. The designed peptides were deemed to have significant probability of retaining an α-helical conformation in solution. For certain peptides, the helical propensity of peptides was enhanced by introduction of polar or charged side chains to form intra-molecular H-bonds and salt bridges at positions that did not interact with Id1. Only peptides containing natural amino acids only were considered.

Multiple dynamics simulations were performed for the model of Id1-peptide complex in order to assess stability of the proposed peptide and dimer structure. The simulations were carried out in vacuum at 300° K with the AMBER-94 force field. Positional constraints were applied to maintain backbone atoms of Id1 close to the coordinated of crystal structure; side chain atoms of Id1 and all atoms of the peptide were not constrained. During the 40 picosecond equilibration and 300 picosecond acquisition simulations, the structure of the dimer retained close to the initial model with relatively small fluctuation in potential energy. The peptide maintained an α-helical structure during entire multiple dynamics trajectory. Root mean square deviations between peptide positions in the initial model and in the final multiple dynamics structure was 0.50 Å for $C^α$ atoms and 0.74 Å for all heavy atoms. The inter-molecular H-bonds anchoring the peptide to Id1 were calculated to remain stable during the multiple dynamics simulations.

Twelve peptides (Table 2) that met the required criteria were identified as potential anti-Id compounds.

TABLE 2

Twelve synthetic peptides that were created using the E47 molecule from an X-ray of the structure of E47- Id1 heterodimer as a template for peptide design.

| Compound | Vendor | ID | Catalogue # | CHEMICAL NAME |
| --- | --- | --- | --- | --- |
| 1 | AngioGenex | 914041282 | P1 | ELLILQRLVQVILALQ-OH |
| 2 | AngioGenex | 914041283 | P2 | ELLFLQRLVQLILALQ-OH |
| 3 | AngioGenex | 914041284 | P3 | ELLFLQALVQLILALQ-OH |
| 4 | AngioGenex | 914041285 | P4 | ELLFLQRLVQLIEALQ-OH |
| 5 | AngioGenex | 914041287 | P5 | DLLLLQRLVQLIEALQ-OH |
| 6 | AngioGenex | 914041286 | P6 | DLLFLQRLVQLIEALQ-OH |
| 7 | AngioGenex | 914041288 | P7 | ELKFLQRLVQLIEALQ-OH |
| 8 | AngioGenex | 914041289 | P8 | ELEFLQRLVQLIEALQ-OH |
| 9 | AngioGenex | 914041290 | P9 | ELEFLQRLVDLIEKLQ-OH |
| 10 | AngioGenex | 914041291 | P10 | DLEFLQRLVDLIEKLQ-OH |
| 11 | AngioGenex | 914041292 | P11 | ELKFLQRLVDLIEKLQ-OH |
| 12 | AngioGenex | 914041293 | P12 | ELKFLQRLVDLIEKLE-OH |

The identified peptides were then subjected to further testing and analysis using the gel shift and cellular assays described in further detail in the examples that follow.

Example III

Gel Shift Assays of Identified Proteins

Gel shift assays were performed using the 376 small molecules identified in the in silico drug screen and peptide synthesis. The identified compounds were then dissolved in 5% DMSO to a concentration of 100 μm and reacted in binding mixtures that contained E47, Id1 and Mck. As controls, recombinant human E47 was used in a standard binding reaction that contained $^{32}$P labeled MCK double stranded oligonucleotides containing consensus E-Box response element (MCK-5' TTG ATC CCC CCA ACA CCT GCT GCC TGA AGC T (SEQ ID NO. 1)) and 100 ng of Id1 was added to a standard binding reaction using E47 and p32 labeled MCK. After 30 minutes of incubation, the reaction mixtures were resolved on a 5% non-denaturing polyacrylamide gel and autoradiographed. The bound E47-MCK resulted in a shifted band whereas the unbound MCK migrated to the bottom of the gel. The reaction mixture containing Id1 and E47 and MCK showed a failure of E47 to bind to MCK. If the identified molecules were capable of inhibiting Id1, the gel shift assay showed a shifted band of bound E47-MCK. The presence of shifted band also suggests that the small molecules have no effect on the interaction between E47 and MCK, a critical observation that demonstrates the absence of any non-specific effect of small molecules on the normal bHLH mediated transcriptional pathway. An exemplary assay is shown in FIG. 1.

Of the 376 small molecules identified in the in silico drug screen, the 17 in Table 3 were identified as demonstrating the most pronounced anti-Id activity in the gel shift assay. These molecules resulted in the gel shift in the presence of E47, Id1 and MCK.

TABLE 3

Compounds showing the most pronounced anti-Id activity in the gel shift assay.

| Compound | Vendor | ID | Formula | MW | CHEMICAL NAME |
| --- | --- | --- | --- | --- | --- |
| 43 | ChemDiv | 3381-0867 | C22H30N2O4 | 386.4954 | 1-(4-methoxybenzyl)-4-(2,4,5-trimethoxybenzyl)piperazine |
| 118 | ChemDiv | 8011-9794 | C23H21ClN2O3 | 408.88842 | N'-acetyl-N'-(3-chloro-4-methylphenyl)-2-hydroxy-2,2-diphenylacetohydrazide |
| 142 | ChemDiv | C125-0426 | C25H22F3N3O4 | 485.46699 | 6,7-dimethoxy-2-methyl-1-oxo-3-pyridin-3-yl-N-[3-(trifluoromethyl)phenyl]-1,2,3,4-tetrahydroisoquinoline-4-carboxamide |
| 169 | ChemDiv | C258-0518 | C24H29N3O4S | 455.58043 | 2-[3-(3,4-dimethylphenyl)-2,4-dioxo-3,4,6,7,8,9-hexahydro-2H-cyclohepta[4,5]thieno[2,3-d]pyrimidin-1(5H)-yl]-N-(2-methoxyethyl)acetamide |
| 194 | ChemDiv | C444-0317 | C17H28N2O2 | 292.42491 | 4-acetyl-N,N-dibutyl-3,5-dimethyl-1H-pyrrole-2-carboxamide |
| 235 | ChemDiv | K788-6627 | C29H29N3O4S | 515.63618 | N-(4-isopropylphenyl)-2-[8-(morpholin-4-ylcarbonyl)-11-oxodibenzo[b,f][1,4]thiazepin-10(11H)-yl]acetamide |

TABLE 3-continued

Compounds showing the most pronounced anti-Id activity in the gel shift assay.

| Compound | Vendor | ID | Formula | MW | CHEMICAL NAME |
|---|---|---|---|---|---|
| 302 | Chembridge | 6539631 | C19H28N2O5 | 364.44541 | ethyl 1-{3-[(2,5-dimethoxyphenyl)amino]-3-oxopropyl}-4-piperidinecarboxylate hydrochloride |
| 287 | Chembridge | 6047903 | C16H15F3N2O3S | 372.36875 | ethyl 2-amino-4-methyl-5-({[2-(trifluoromethyl)phenyl]amino}carbonyl)-3-thiophenecarboxylate |
| 312 | Chembridge | 6948667 | C27H29NO4 | 431.53648 | N-[3-(1,3-benzodioxol-5-yl)-3-(2-methoxyphenyl)propyl]-N-benzylpropanamide |
| 317 | Chembridge | 7111754 | C22H22O6 | 382.41704 | Methyl {7-[(3-methoxybenzyl)oxy]-4,8-dimethyl-2-oxo-2H-chromen-3-yl}acetate |
| 249 | Maybridge | RJC 00532 | C16H14N2O5 | 314.30038 | Ethyl 3-hydroxy-5-methyl-6-oxo-1-phenyl-1,6-dihydropyrano[2,3-c]pyrazole-4-carboxylate |
| 250 | Maybridge | SCR 00426 | C19H21ClN2O4S | 408.90722 | 1-(1,3-benzodioxol-5-ylmethyl)-4-[(4-chlorobenzyl)sulfonyl]piperazine |
| 252 (Agx-8) | Maybridge | HTS 03876 | C18H18N2OS | 310.42096 | N'-(4-isopropylphenyl)-1-benzothiophene-2-carbohydrazide |
| 8 | Sigma Aldrich (Salor) | 7476 | C27H31BrN2O5 | 543.46252 | RCL L34,794-9 |
| 10 | Sigma Aldrich (Salor) | 36895 | C28H33FN2O5 | 496.58401 | RCL L34,930-5 |
| 11 | Sigma Aldrich (Salor) | 7461 | C25H26BrFN2O5 | 533.39877 | RCL L35,342-6 |
| 364 | AngioGenex | 914041290 | | | ELEFLQRLVDLIEKLQ-OH |

The use of the molecules in Table 3 resulted in the gel shift in the presence of E47, Id1 and E box. These 17 molecules were subjected to an additional gel shift assay to ensure repeatability and consistency of results. All of these compounds resulted in a hit (i.e., inhibited in the gel shift assay) suggesting that these selected compounds were capable of blocking Id1-E47 interaction. Based on the intensity of the gel shift (considered as equivalent to potency in inhibiting Id1-E47 interaction), two small molecules: N'-(4-isopropylphenyl)-1-benzothiophene-2-carbohydrazide and N-[3-(1,3-benzodioxol-5-yl)-3-(2-methoxyphenyl)propyl]-N-benzylpropanamide were selected for further testing. However, all 376 molecules in Tables 1, 2 and specifically all 17 molecules listed in Table 3 are considered as potential inhibitors of Id1-E47 interactions.

N'-(4-isopropylphenyl)-1-benzothiophene-2-carbohydrazide (HTS 03876, Maybridge) and N-[3-(1,3-benzodioxol-5-yl)-3-(2-methoxyphenyl)propyl]-N-benzylpropanamide (6958667, Chembridge) were identified based on their ability to restore the binding between E47-MCK in the presence of Id1. The ability of these molecules to block E47-Id1 interaction was confirmed at least twice in a similar assay before analyzing their effects on cell based assays. In addition, the effect of both compounds demonstrated dose-proportionality in the gel shift assay.

Example IV

Effects of Identified Small Molecules on Cancer Cell Lines

Prostate cancer cell lines DU145 and PC3 (in 10% BCS) were obtained from American Type Culture Collection (Rockville, Md.). The cells were cultured in Ham's F12 (Gibco, Carlsbad, Calif.) medium containing 10% BCS (Hyclone, Logan, Utah) and appropriate antibiotics (pen/strep, fungizaone, and gentamycin (Invitrogen Inc., Carlsbad, Calif.). All cells were cultured at 37° C. in a fully humidified atmosphere containing 5% $CO_2$.

At 50% confluence, the cells were treated with either 100 μM DMSO, 1000 mOsmol of urea+NaCL, 1 μM N-[3-(1,3-benzodioxol-5-yl)-3-(2-methoxyphenyl)propyl]-N-benzylpropanamide, 10 μM N-[3-(1,3-benzodioxol-5-yl)-3-(2-methoxyphenyl)propyl]-N-benzylpropanamide, and 100 μM N-[3-(1,3-benzodioxol-5-yl)-3-(2-methoxyphenyl)propyl]-N-benzylpropanamide, 1 μM N'-(4-isopropylphenyl)-1-benzothiophene-2-carbohydrazide, 10 μM N'-(4-isopropylphenyl)-1-benzothiophene-2-carbohydrazide, or 100 μM N'-(4-isopropylphenyl)-1-benzothiophene-2-carbohydrazide. The cell morphology and growth was monitored daily for 1 week by microscopy for changes in morphology or cell death. Apoptosis was determined by measuring caspase 3 and caspase 7 activities using the Caspase-Glo 3/7 Assay system from Promega (Madison, Wis.).

Figure 2:
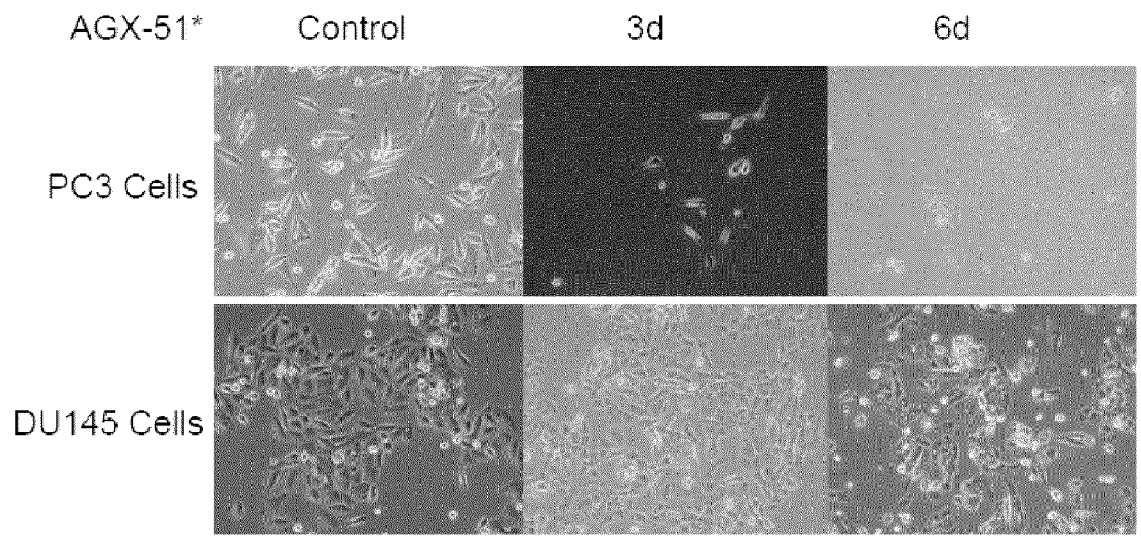
FIG. 2 is images showing the effect of N-[3-(1,3-benzodioxol-5-yl)-3-(2-methoxyphenyl)propyl]-N-benzylpropanamide on the survival of cells from prostate cancer cell lines PC3 and DU145 3 and 6 days after treatment with 100 μm of N-[3-(1,3-benzodioxol-5-yl)-3-(2-methoxyphenyl)propyl]-N-benzylpropanamide.
Figure 3:
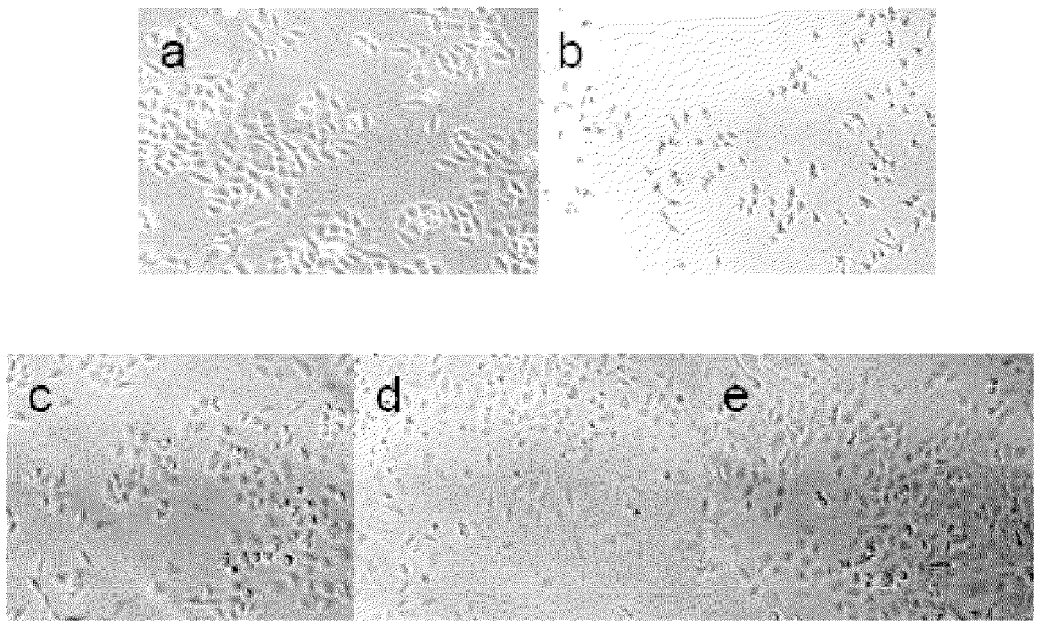
FIG. 3 a-e are pictures comparing the effect of (a) 100 μM DMSO; (b) 1000 mOsmol of urea+NaCL; (c) 1 μm of N-[3-(1,3-benzodioxol-5-yl)-3-(2-methoxyphenyl)propyl]-N-benzylpropanamide; (d) 10 μm N-[3-(1,3-benzodioxol-5-yl)-3-(2-methoxyphenyl)propyl]-N-benzylpropanamide; and (e) 100 μm of N-[3-(1,3-benzodioxol-5-yl)-3-(2-methoxyphenyl)propyl]-N-benzylpropanamide on the survival of cells from prostate cancer cell line DU145.
Figure 6:
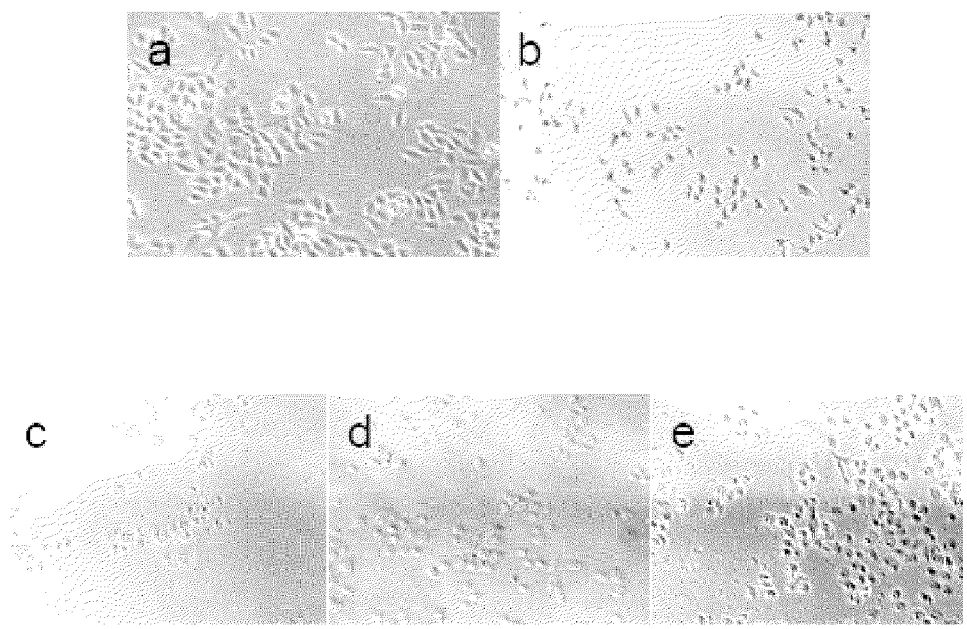
FIG. 6 a-e are pictures showing the effect of (a) 100 μM DMSO; (b) 1000 mOsmol of urea+NaCl; (c) 1 μm N'-(4-isopropylphenyl)-1-benzothiophene-2-carbohydrazide; (d) 10 μm N'-(4-isopropylphenyl)-1-benzothiophene-2-carbohydrazide; and (e) 100 μm N'-(4-isopropylphenyl)-1-benzothiophene-2-carbohydrazide on the survival of cells from prostate cancer cell line DU145.

As shown in FIG. 2, N-[3-(1,3-benzodioxol-5-yl)-3-(2-methoxyphenyl)propyl]-N-benzylpropanamide, at 100 μm concentration led to massive cell death of PC3 cells within 3 days with no surviving cells observed after six days of treatment. While the effect of N-[3-(1,3-benzodioxol-5-yl)-3-(2-methoxyphenyl)propyl]-N-benzylpropanamide on DU145 cells was not as pronounced after three days, the cells appeared very unhealthy and were unable to proliferate as compared to the controls. Additionally, after six days, treatment of DU145 cells with N-[3-(1,3-benzodioxol-5-yl)-3-(2-methoxyphenyl)propyl]-N-benzylpropanamide did lead to cell death. N-[3-(1,3-benzodioxol-5-yl)-3-(2-methoxyphenyl)propyl]-N-benzylpropanamide was also able to induce apoptosis in DU145 at concentrations as low as 1 μM (FIG. 3(c)). Cell survival was also sensitive to N'-(4-isopropylphenyl)-1-benzothiophene-2-carbohydrazide. N'-(4-isopropylphenyl)-1-benzothiophene-2-carbohydrazide, at a concentration of 1 um was able to induce cell death in DU145 cells (FIG. 6). In short, two small molecule inhibitors of E47-Id1 interaction were identified that induce massive cell death in prostate cancer cell lines.

Figure 4:
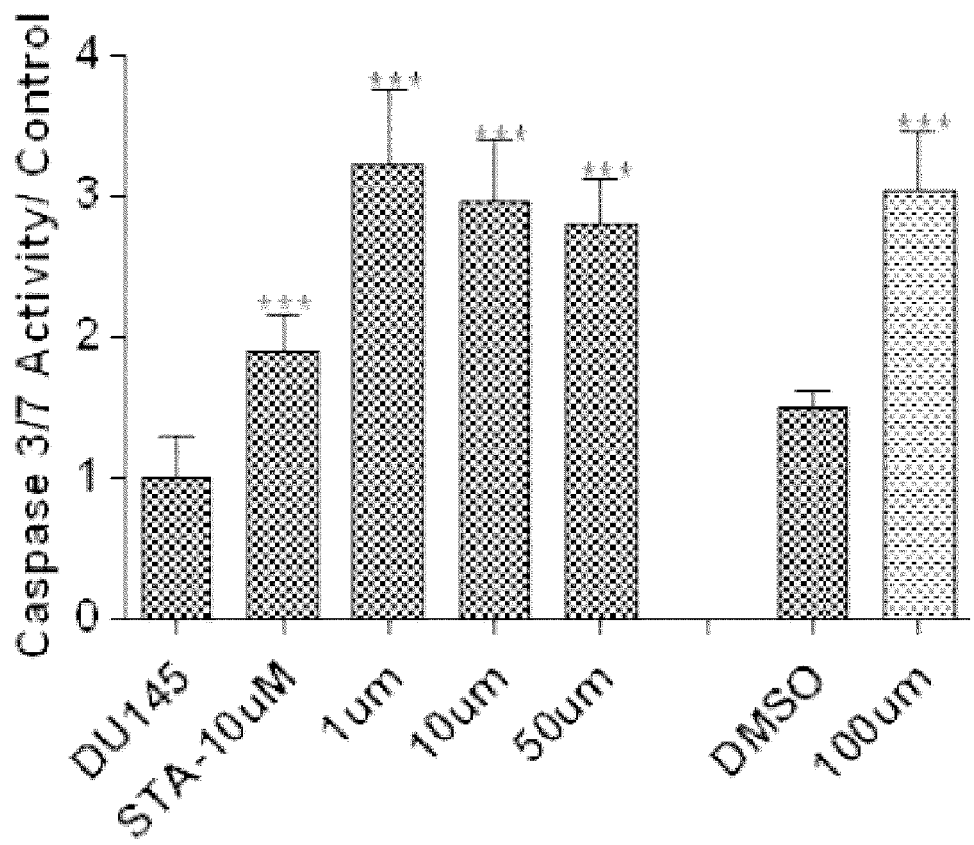
FIG. 4 is a chart comparing the effect of treatment of DU145 prostate cancer cells with Staruosporin (positive control for induction of apoptosis) and varying concentrations of N-[3-(1,3-benzodioxol-5-yl)-3-(2-methoxyphenyl)propyl]-N-benzylpropanamide.
Figure 5:
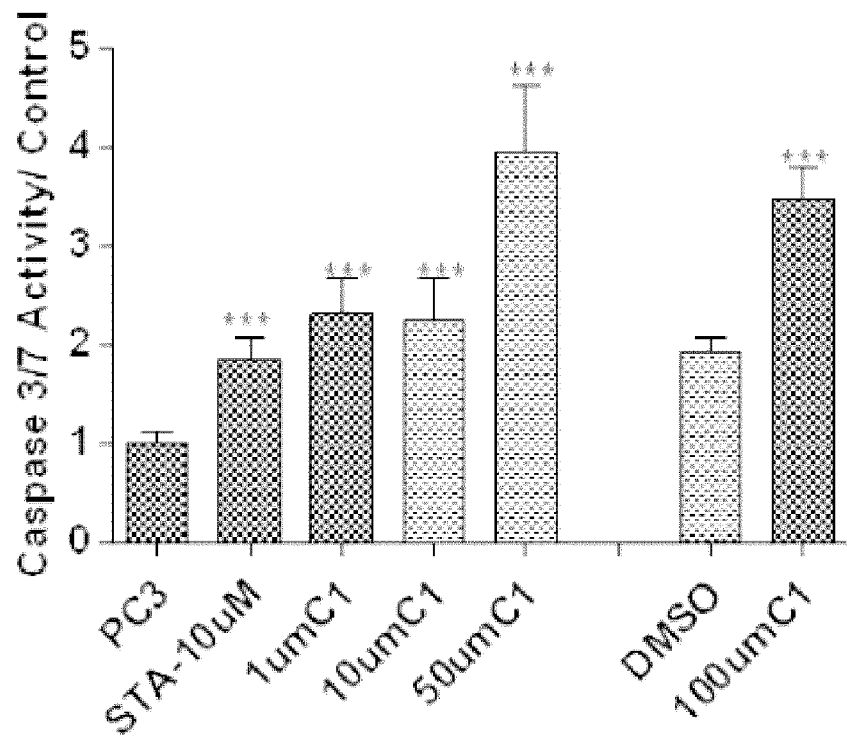
FIG. 5 is a chart comparing the effect of treatment of PC3 prostate cancer cells with Staruosporin and varying concentrations of N-[3-(1,3-benzodioxol-5-yl)-3-(2-methoxyphenyl)propyl]-N-benzylpropanamide.

The molecular mechanism underlying the effect of N-[3-(1,3-benzodioxol-5-yl)-3-(2-methoxyphenyl)propyl]-N-benzylpropanamide on prostate cancer cells was assessed by measuring the activity of the primary mediators of apoptosis, caspase 3/7. As expected, treatment with N-[3-(1,3-benzodioxol-5-yl)-3-(2-methoxyphenyl)propyl]-N-benzylpropanamide (1-100 μm) resulted in a significant increase in caspase 3/7 in both DU145 and PC3 cells (FIGS. 4 and 5) which was higher than the caspase activity in cells treated with staurosporine (10 μm), a known apoptosis inducing agent.

Example V

Effect of Identified Compounds on Anti-Angiogenic Activity in a Matrigel Assay in Mice VEGF-165 and FGF-2 treated Matrigel plugs were implanted on Day 0 into C57BL/6 mice. Mice were treated with either vehicle or N-[3-(1,3-benzodioxol-5-yl)-3-(2-methoxyphenyl)propyl]-N-benzylpropanamide. The N-[3-(1,3-benzodioxol-5-yl)-3-(2-methoxyphenyl)propyl]-N-benzylpropanamide was provided either in the plugs (25 μg/mg) or by daily ip treatment (30 or 100 mg/kg) for 10 days. Plugs were harvested on Day 10, fixed and paraffin embedded. Three sections (5 μM thickness) of each plug were stained with an anti-CD31 antibody and counterstained with hematoxylin and eosin stain. CD31-positive microvessels were counted for one entire cross-section per plug and the average micro-vessel density±SD vessels was determined. Student's t-test was used for statistical analysis.

Figure 7:
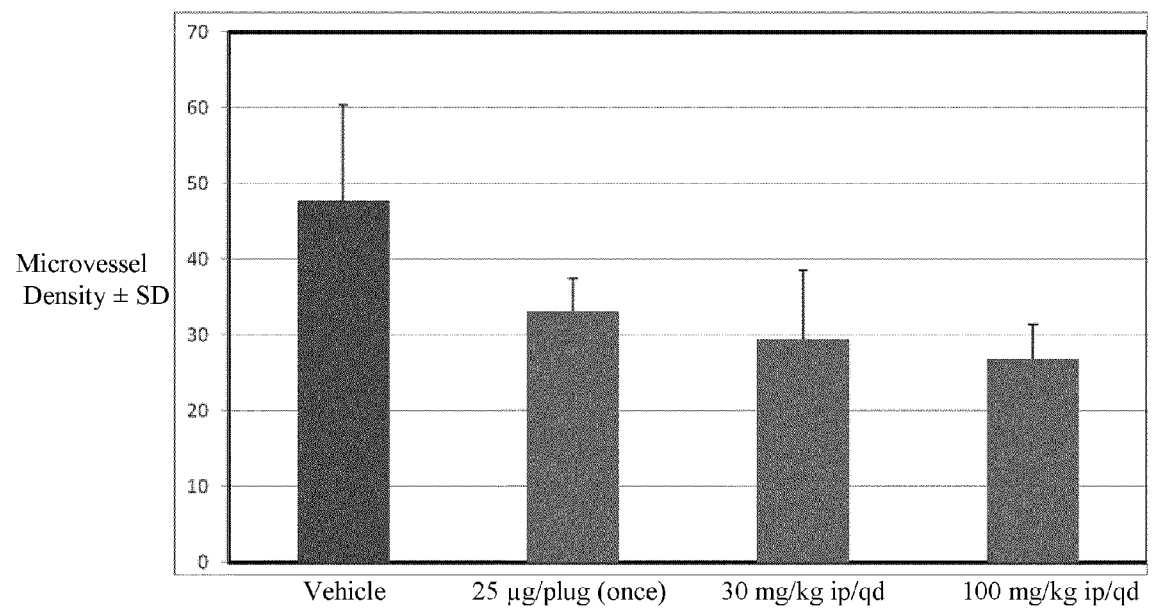
FIG. 7 is a chart illustrating the effect of N-[3-(1,3-benzodioxol-5-yl)-3-(2-methoxyphenyl)propyl]-N-benzylpropanamide on formation of blood vessel into VEGF-165 and FGF-2 treated Matrigel plugs implanted into the flanks of C57/BL mice.

Microvessel data from this study is provided in FIG. 7. Compared to vehicle control animals, all N-[3-(1,3-benzodioxol-5-yl)-3-(2-methoxyphenyl)propyl]-N-benzylpropanamide treatments provided significant protection from new blood vessel formation. Statistics for the study were: p>0.05 (n=7), 0.01 (n=6) and 0.01 (n=7) compared to vehicle (n=9) for 25 μg/plug, 30 and 100 mg/kg dose groups respectively. The maximum protection was 44% at an ip dose of 100 mg/kg, qd.

Figure 8:
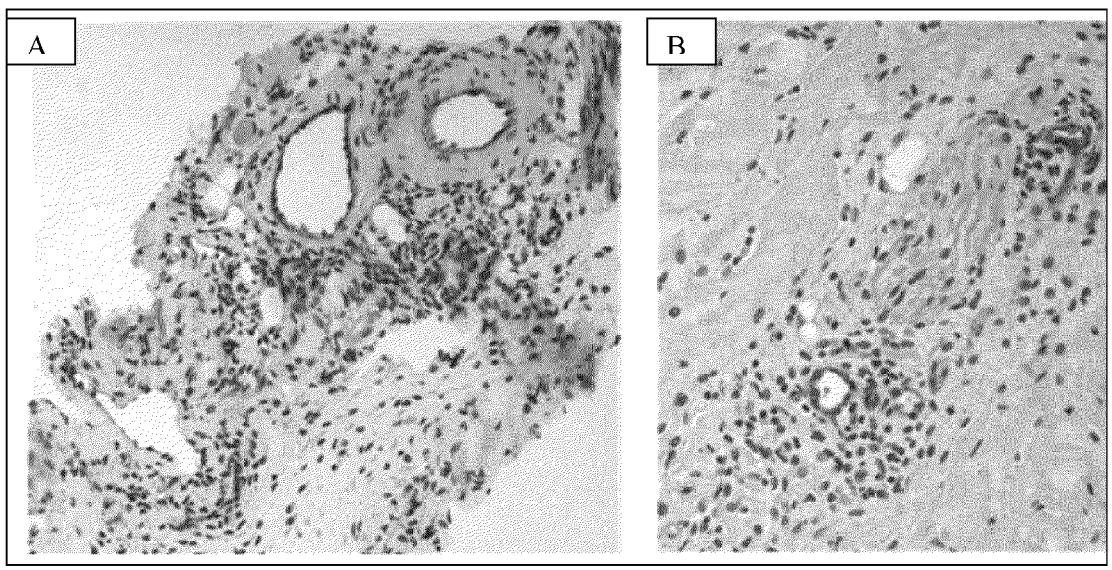
FIG. 8 provides pictures of slices of VEGF-165 and FGF-2 treated Matrigel plugs removed from mice 10 days after implantation.

A typical picture of slices of the Matrigel plugs are provided in FIG. 8. The left panel is a typical picture of an anti-CD31 antibody stained plug from a mouse treated with vehicle (DMSO). The right panel is a picture of a typical plug from mouse treated daily for 10 days ip with 30 mg/kg N-[3-(1,3-benzodioxol-5-yl)-3-(2-methoxyphenyl)propyl]-N-benzylpropanamide. As can be seen in a comparison of the two pictures, the presence of complete blood vessels and therefore the presence of endothelial cells is seen to significantly decrease with N-[3-(1,3-benzodioxol-5-yl)-3-(2-methoxyphenyl)propyl]-N-benzylpropanamide treatment.

Example VI

Effect of Identified Compounds on Metastatic Activity in a LLC Mouse Model

Figure 9:
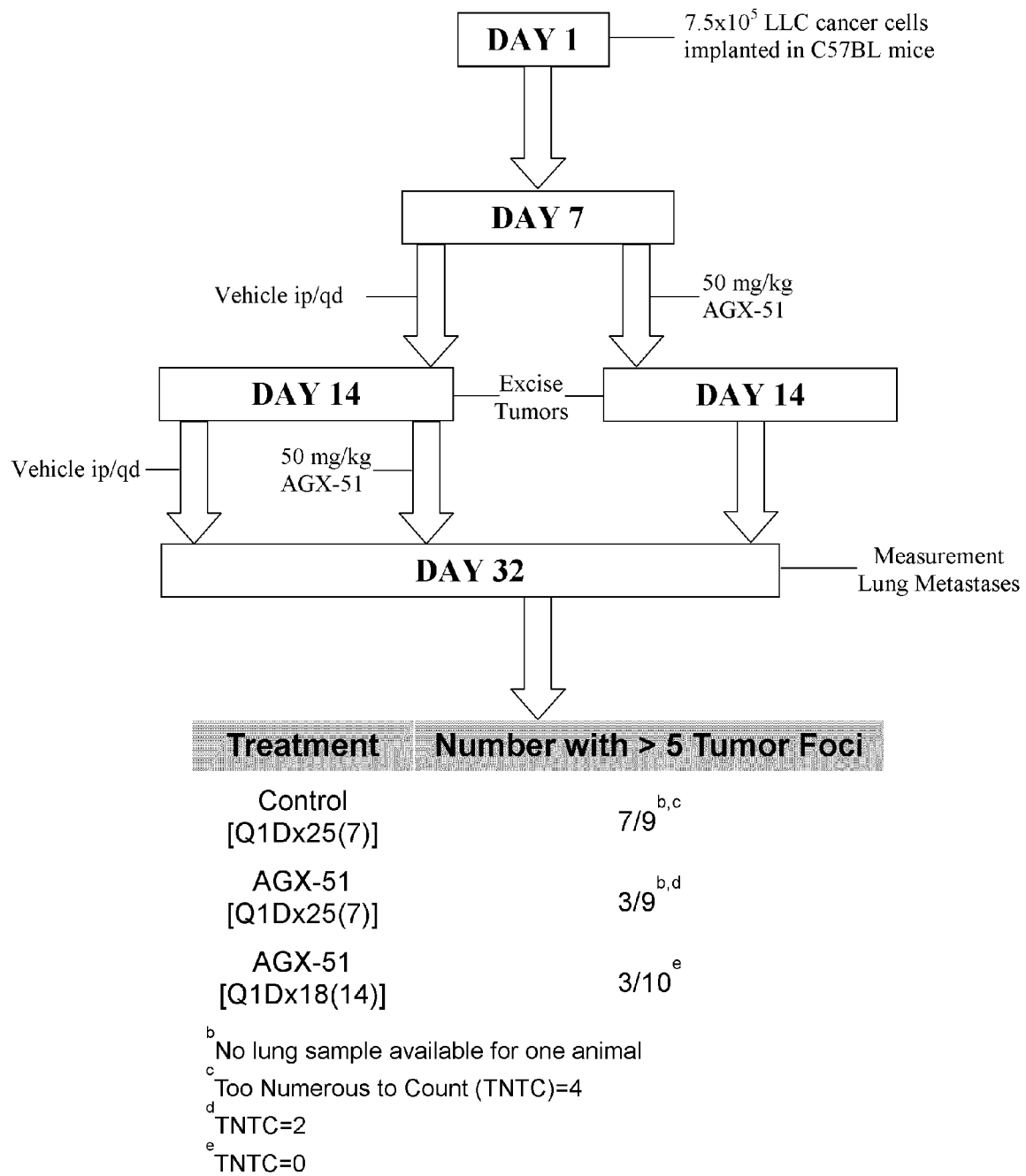
FIG. 9 provides a scheme and results for a study to determine the effect of N-[3-(1,3-benzodioxol-5-yl)-3-(2-methoxyphenyl)propyl]-N-benzylpropanamide (AGX 51) on lung metastasis of LLC tumors implanted into C 57/BL mice and excised 14 days after implantation.

Thirty C57BL/6 mice were implanted with $7.5 \times 10^5$ LLC cancer cells/animal. Seven days after implantation, 5M/5F per group were treated daily ip for 25 days with either dosing vehicle (DMSO) or 50 mg/kg N-[3-(1,3-benzodioxol-5-yl)-3-(2-methoxyphenyl)propyl]-N-benzylpropanamide (AGX 51). Fourteen days after implantation, another group of 5M/5F animals were treated daily ip for 18 days with 50 mg/kg N-[3-(1,3-benzodioxol-5-yl)-3-(2-methoxyphenyl) propyl]-N-benzylpropanamide. Tumors were measured three times from Day 7 to 14. On Day 14, the tumors were excised. As shown in FIG. 9, the animals were necropsied for the presence of lung metastases on day 32, 18 days post excision. As can be seen in FIG. 9, treatment with N-[3-(1,3-benzodioxol-5-yl)-3-(2-methoxyphenyl)propyl]-N-benzylpropanamide profoundly diminishes lung metastases.

As presented in Table 4, tumors at day 14 were approximately the same size for each treatment group, providing assurance that any difference in lung metastases found at the end of the experiment was not the result of different tumor sizes in the groups.

TABLE 4

Tumor Size Each Group Same at Excision[a]

| Treatment | Mean Size ± SD on Day 14 (Treatment for 7 Days) |
|---|---|
| Control [Q1Dx25(7)] | 366 ± 226 mg |
| N-[3-(1,3-benzodioxol-5-yl)-3-(2-methoxyphenyl)propyl]-N-benzylpropanamide [Q1Dx25(7)] | 327 ± 075 mg |
| N-[3-(1,3-benzodioxol-5-yl)-3-(2-methoxyphenyl)propyl]-N-benzylpropanamide [Q1Dx18(14)] | 386 ± 083 mg |

[a]Expected Because Only 7 Day Treatment

Example VII

Effect of Identified Compounds on Growth of MDA-231 Human Breast Cancer Tumors in SCID Mice Nude mice (n=8/treatment group) were implanted with MDA231 human cancer cells. Fourteen days after implantation, the mice were treated ip with DMSO (vehicle) or 50 mg/kg N-[3-(1,3-benzodioxol-5-yl)-3-(2-methoxyphenyl) propyl]-N-benzylpropanamide in DMSO. All mice were treated iv for 5 consecutive days with 7.5 mg/kg Taxol starting on days 8 and 22. Boxplots are tumor volumes 53 days post implantation (last day of the study).

Figure 10:
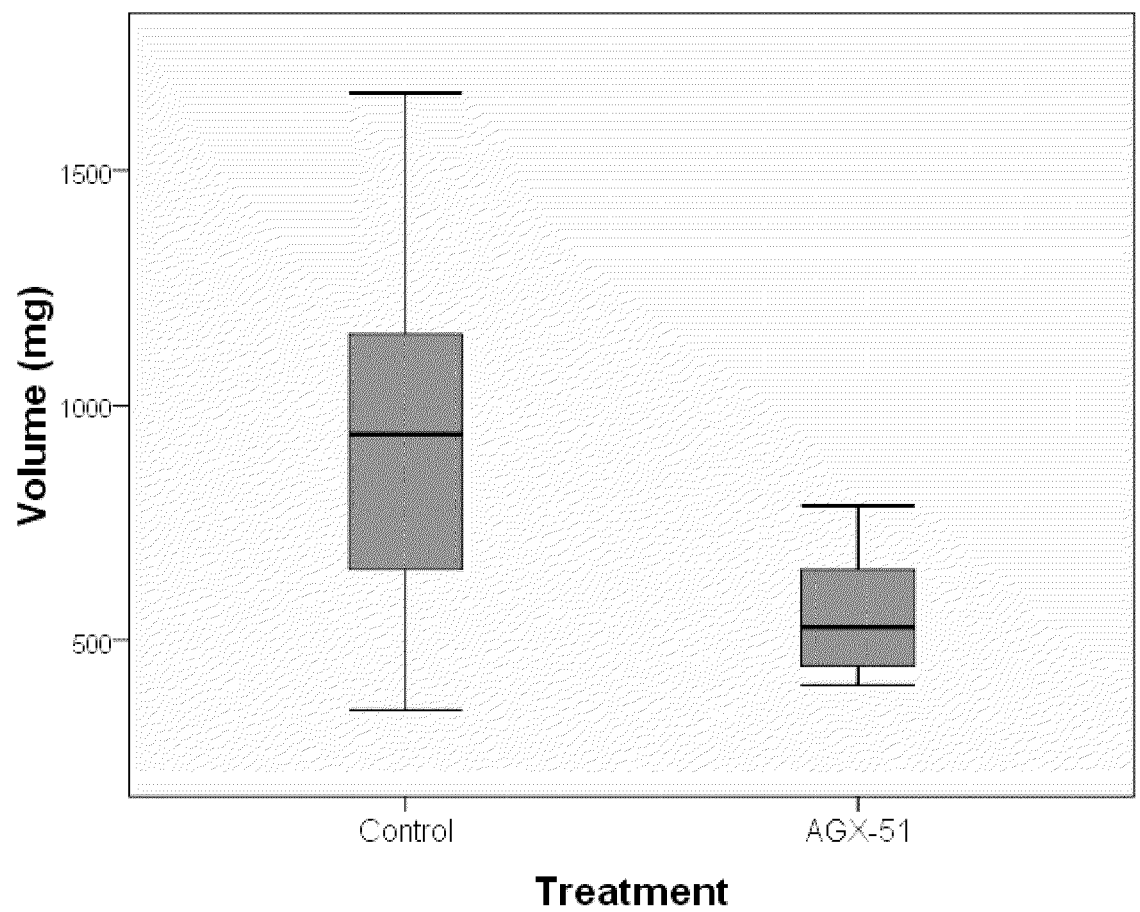
FIG. 10 is a chart providing data from the xenograft study performed in SCID mice implanted with MDA 231 human breast tumors and treated either with vehicle (DMSO) or 50 mg/kg per day in AGX 51 (N-[3-(1,3-benzodioxol-5-yl)-3-(2-methoxyphenyl)propyl]-N-benzylpropanamide).

Two animals in the control group and one animal in the treated group died before day 53 (data not used). Tumor size findings for all surviving animals are provided in FIG. 10. As shown in FIG. 10, treatment with N-[3-(1,3-benzodioxol-5-yl)-3-(2-methoxyphenyl)propyl]-N-benzylpropanamide (AGX 51) is seen to provide a significant [p=0.05 compared to vehicle (DMSO) control} negative effect of approximately 50% on tumor growth.

Although the foregoing invention has been described in detail by way of example for purposes of clarity of understanding, it will be apparent to the artisan that certain changes and modifications may be practiced within the scope of the appended claims which are presented by way of illustration not limitation. In this context, various publications and other references have been cited with the foregoing disclosure for economy of description. Each of these references is incorporated herein by reference in its entirety for all purposes. It is noted, however, that the various publications discussed herein are incorporated solely for their disclosure prior to the filing date of the present application, and the inventors reserve the right to antedate such disclosure by virtue of prior invention.

REFERENCES

Littlewood, T. D. and G. I. Evan, *Transcription factors 2: helix-loop-helix*. Protein Profile, 1995. 2(6): p. 621-702.

Massari, M. E. and C. Murre, *Helix-loop-helix proteins: regulators of transcription in eucaryotic organisms*. Mol Cell Biol, 2000. 20(2): p. 429-40.

Quong, M. W., et al., *A new transcriptional-activation motif restricted to a class of helix-loop-helix proteins is functionally conserved in both yeast and mammalian cells*. Mol Cell Biol, 1993. 13(2): p. 792-800.

Ledent, V., O. Paquet, and M. Vervoort, *Phylogenetic analysis of the human basic helix-loop-helix proteins*. Genome Biol, 2002. 3(6): p. RESEARCH0030.

Murre, C., P. S. McCaw, and D. Baltimore, *A new DNA binding and dimerization motif in immunoglobulin enhancer binding, daughterless, MyoD, and myc proteins*. Cell, 1989. 56(5): p. 777-83.

Murre, C., et al., *Interactions between heterologous helix-loop-helix proteins generate complexes that bind specifically to a common DNA sequence*. Cell, 1989. 58(3): p. 537-44.

Coppe, J. P., A. P. Smith, and P. Y. Desprez, *Id proteins in epithelial cells*. Exp Cell Res, 2003. 285(1): p. 131-45.

Murre, C., et al., *Structure and function of helix-loop-helix proteins*. Biochim Biophys Acta, 1994. 1218(2): p. 129-35.

Deed, R. W., et al., *Structural organisation and chromosomal mapping of the human Id-3 gene*. Gene, 1994. 151(1-2): p. 309-14.

Deed, R. W., M. Jasiok, and J. D. Norton, *Nucleotide sequence of the cDNA encoding human helix-loop-helix Id-1 protein: identification of functionally conserved residues common to Id proteins*. Biochim Biophys Acta, 1994. 1219(1): p. 160-2.

Benezra, R., et al., *The protein Id: a negative regulator of helix-loop-helix DNA binding proteins*. Cell, 1990. 61(1): p. 49-59.

Barone, M. V., et al., *Id proteins control growth induction in mammalian cells*. Proc Natl Acad Sci USA, 1994. 91(11): p. 4985-8.

Shoji, W., T. Yamamoto, and M. Obinata, *The helix-loop-helix protein Id inhibits differentiation of murine erythroleukemia cells*. J Biol Chem, 1994. 269(7): p. 5078-84.

Moldes, M., et al., *Id3 prevents differentiation of preadipose cells*. Mol Cell Biol, 1997. 17(4): p. 1796-804.

Lister, J., W. C. Forrester, and M. H. Baron, *Inhibition of an erythroid differentiation switch by the helix-loop-helix protein Id1*. J Biol Chem, 1995. 270(30): p. 17939-46.

Biggs, J. R., Y. Zhang, and E. V. Murphy, *Repression of the Id2 (inhibitor of differentiation) gene promoter during exit from the cell cycle*. J Cell Physiol, 1995. 164(2): p. 249-58.

Hara, E., et al., *Id-related genes encoding helix-loop-helix proteins are required for G1 progression and are repressed in senescent human fibroblasts*. J Biol Chem, 1994. 269(3): p. 2139-45.

Jen, Y., K. Manova, and R. Benezra, *Expression patterns of Id1, Id2, and Id3 are highly related but distinct from that of Id4 during mouse embryogenesis*. Dev Dyn, 1996. 207(3): p. 235-52.

Kondo, T. and M. Raff, *The Id4 HLH protein and the timing of oligodendrocyte differentiation*. Embo J, 2000. 19(9): p. 1998-2007.

Kreider, B. L., et al., *Inhibition of myeloid differentiation by the helix-loop-helix protein Id*. Science, 1992. 255(5052): p. 1700-2.

Melnikova, I. N. and B. A. Christy, *Muscle cell differentiation is inhibited by the helix-loop-helix protein Id3*. Cell Growth Differ, 1996. 7(8): p. 1067-79.

Norton, J. D., *ID helix-loop-helix proteins in cell growth, differentiation and tumorigenesis*. J Cell Sci, 2000. 113 (Pt 22): p. 3897-905.

Iavarone, A., et al., *The helix-loop-helix protein Id-2 enhances cell proliferation and binds to the retinoblastoma protein*. Genes Dev, 1994. 8(11): p. 1270-84.

Inoue, T., W. Shoji, and M. Obinata, *MIDA1, an Id-associating protein, has two distinct DNA binding activities that are converted by the association with Id1: a novel function of Id protein*. Biochem Biophys Res Commun, 1999. 266(1): p. 147-51.

Inoue, T., W. Shoji, and M. Obinata, *MIDA1 is a sequence specific DNA binding protein with novel DNA binding properties*. Genes Cells, 2000. 5(9): p. 699-709.

Yates, P. R., et al., *Id helix-loop-helix proteins inhibit nucleoprotein complex formation by the TCF ETS-domain transcription factors*. Embo J, 1999. 18(4): p. 968-76.

Roberts, E. C., et al., *Id helix-loop-helix proteins antagonize pax transcription factor activity by inhibiting DNA binding*. Mol Cell Biol, 2001. 21(2): p. 524-33.

Alani, R. M., et al., *Immortalization of primary human keratinocytes by the helix-loop-helix protein, Id-1*. Proc Natl Acad Sci USA, 1999. 96(17): p. 9637-41.

Israel, M. A., et al., *Id gene expression as a key mediator of tumor cell biology*. Cancer Res, 1999. 59(7 Suppl): p. 1726s-1730s.

Wice, B. M. and J. I. Gordon, *Forced expression of Id-1 in the adult mouse small intestinal epithelium is associated with development of adenomas*. J Biol Chem, 1998. 273(39): p. 25310-9.

Sikder, H. A., et al., *Id proteins in cell growth and tumorigenesis*. Cancer Cell, 2003. 3(6): p. 525-30.

Ouyang, X. S., et al., *Over expression of ID-1 in prostate cancer*. J Urol, 2002. 167(6): p. 2598-602.

Ouyang, X. S., et al., *Id-1 stimulates serum independent prostate cancer cell proliferation through inactivation of p16(INK4a)/pRB pathway*. Carcinogenesis, 2002. 23(5): p. 721-5.

Coppe, J. P., et al., *Id-1 and Id-2 proteins as molecular markers for human prostate cancer progression*. Clin Cancer Res, 2004. 10(6): p. 2044-51.

Ling, M. T., et al., *Activation of MAPK signaling pathway is essential for Id-1 induced serum independent prostate cancer cell growth*. Oncogene, 2002. 21(55): p. 8498-505.

Ling, M. T., et al., *Down-regulation of Id-1 expression is associated with TGF beta 1-induced growth arrest in prostate epithelial cells.* Biochim Biophys Acta, 2002. 1570(3): p. 145-52.

Murre, C., Voronova, A. & Baltimore, D. B-cell- and myocyte-specific E2-box-binding factors contain E12/E47-like subunits. Mol Cell Biol 11, 1156-60 (1991).

Beger, C., et al., *Identification of Id4 as a regulator of BRCA1 expression by using a ribozyme-library-based inverse genomics approach.* Proc Natl Acad Sci USA, 2001. 98(1): p. 130-5.

Alani, R. M., A. Z. Young, and C. B. Shifflett, *Id1 regulation of cellular senescence through transcriptional repression of p16/Ink4a.* Proc Natl Acad Sci USA, 2001. 98(14): p. 7812-6.

Horoszewicz, J. S., et al., *The LNCaP cell line—a new model for studies on human prostatic carcinoma.* Prog Clin Biol Res, 1980. 37: p. 115-32.

Stone, K. R., et al., *Isolation of a human prostate carcinoma cell line (DU 145).* Int J Cancer, 1978. 21(3): p. 274-81.

Lasorella, A., et al., *Id2 is critical for cellular proliferation and is the oncogenic effector of N-myc in human neuroblastoma.* Cancer Res, 2002. 62(1): p. 301-6.

Norton, J. D. and G. T. Atherton, *Coupling of cell growth control and apoptosis functions of Id proteins.* Mol Cell Biol, 1998. 18(4): p. 2371-81.

Zebedee, Z. and E. Hara, *Id proteins in cell cycle control and cellular senescence.* Oncogene, 2001. 20(58): p. 8317-25.

Yokota, Y. and S. Mori, *Role of Id family proteins in growth control.* J Cell Physiol, 2002. 190(1): p. 21-8.

de Candia, P., R. Benera, and D. B. Solit, *A role for Id proteins in mammary gland physiology and tumorigenesis.* Adv Cancer Res, 2004. 92: p. 81-94.

Fong, S., R. J. Debs, and P. Y. Desprez, *Id genes and proteins as promising targets in cancer therapy.* Trends Mol Med, 2004. 10(8): p. 387-92.

Wong, Y. C., X. Wang, and M. T. Ling, *Id-1 expression and cell survival.* Apoptosis, 2004. 9(3): p. 279-89.

Ruzinova, M. B. and R. Benezra, *Id proteins in development, cell cycle and cancer.* Trends Cell Biol, 2003. 13(8): p. 410-8.

Shaked Y, Henke E, Roodhart J M, Mancuso P, Langenberg M H, Colleoni M, Daenen L G, Man S, Xu P, Emmenegger U, Tang T, Zhu Z, Witte L, Strieter R M, Bertolini F, Voest E E, Benezra R, Kerbel R S, Rapid chemotherapy-induced acute endothelial progenitor cell mobilization: implications for antiangiogenic drugs as chemosensitizing agents. Cancer Cell. 2008; 14(3): 263-73.

Henke E, Perk J, Vider J, de Candia P, Chin Y, Solit D B, Ponomarev V, Cartegni L, Manova K, Rosen N, Benezra R. Peptide-conjugated antisense oligonucleotides for targeted inhibition of a transcriptional regulator in vivo. Nat. Biotechnol. 2008; 26(1): 91-100.

Gupta G P, Perk J, Acharyya S, de Candia P, Mittal V, Todorova-Manova K, Gerald W L, Brogi E, Benezra R, Massagué J. ID genes mediate tumor reinitiation during breast cancer lung metastasis. Proc Natl Acad Sci USA. 2007; 104(49):19506-11.

Lyden D, Young A Z, Zagzag D, Yan W, Gerald W, O'Reilly R, Bader B L, Hynes R O, Zhuang Y, Manova K, Benezra R. Id1 and Id3 are required for neurogenesis, angiogenesis and vascularization of tumour xenografts. Nature. 1999; 401(6754): 670-7.

Ciarrocchi A, Jankovic V, Shaked Y, Nolan D J, Mittal V, Kerbel R S, Nimer S D, Benezra R. Id1 restrains p21 expression to control endothelial progenitor cell formation. PLoS ONE. 2007; 2(12): e1338

Li H, Gerald W L, Benezra R. Li H, Gerald W L, Benezra R. Utilization of bone marrow-derived endothelial cell precursors in spontaneous prostate tumors varies with tumor grade. Cancer Res. 2004; 64(17):6137-43.

Lyden D, Hattori K, Dias S, Costa C, Blaikie P, Butros L, Chadbum A, Heissig B, Marks W, Witte L, Wu Y, Hicklin D, Zhu Z, Hackett N R, Crystal R G, Moore M A, Hajjar K A, Manova K, Benezra R, Rafii S. Impaired recruitment of bone-marrow-derived endothelial and hematopoietic precursor cells blocks tumor angiogenesis and growth. Nat. Med. 2001; 7(11): 1194-201.

Gao D, Nolan D J, Mellick A S, Bambino K, McDonnell K, Mittal V. Endothelial progenitor cells control the angiogenic switch in mouse lung metastasis. Science. 2008; 319(5860): 195-8.

Ruzinova M B, Schoer R A, Gerald W, Egan J E, Pandolfi P P, Rafii S, Manova K, Mittal V, Benezra R. Effect of angiogenesis inhibition by Id loss and the contribution of bone-marrow-derived endothelial cells in spontaneous murine tumors. Cancer Cell. 2003; 4(4):277-89.

de Candia P, Solit D B, Giri D, Brogi E, Siegel P M, Olshen A B, Muller W J, Rosen N, Benezra R. Angiogenesis impairment in Id-deficient mice cooperates with an Hsp90 inhibitor to completely suppress HER2/neu-dependent breast tumors. Proc Natl Acad Sci USA. 2003; 100(21): 12337-42.

Swarbrick A, Roy E, Allen T, Bishop J M. Id1 cooperates with oncogenic Ras to induce metastatic mammary carcinoma by subversion of the cellular senescence response. Proc Natl Acad Sci USA. 2008; 105(14): 5402-7.

Cummings S D, Ryu B, Samuels M A, Yu X, Meeker A K, Healey M A, Alani R M. Id1 delays senescence of primary human melanocytes. Mol. Carcinog. 2008; 47(9): 653-9.

Tam W F, Gu T L, Chen J, Lee B H, Bullinger L, Frohling S, Wang A, Monti S, Golub T R, Gilliland D G. Id1 is a common downstream target of oncogenic tyrosine kinases in leukemic cells. Blood. 2008; 112(5): 1981-92.

Suh H C, Leeanansaksiri W, Ji M, Klarmann K D, Renn K, Gooya J, Smith D, McNiece I, Lugthart S, Valk P J, Delwel R, Keller J R. Id1 immortalizes hematopoietic progenitors in vitro and promotes a myeloproliferative disease in vivo. Oncogene. 2008.

Zhao Z R, Zhang Z Y, Zhang H, Jiang L, Wang M W, Sun X F. Overexpression of Id-1 protein is a marker in colorectal cancer progression. Oncol Rep. 2008; 19(2): 419-24.

Ling M T, Wang X, Zhang X, Wong Y C. The multiple roles of Id-1 in cancer progression. Differentiation. 2006; 74(9-10): 481-7.

Wong Y C, Wang X, Ling M T. Id-1 expression and cell survival. Apoptosis. 2004; 9(3): 279-89.

Fong S, Debs R J, Desprez P Y. Id genes and proteins as promising targets in cancer therapy. Trends Mol. Med. 2004; 10(8): 387-92.

Lasorella A, Uo T, Iavarone A. Id proteins at the cross-road of development and cancer. Oncogene. 2001; 20(58): 8326-33.

Perk J, Iavarone A, Benezra R. Id family of helix-loop-helix proteins in cancer. Nat Rev Cancer. 2005; 5(8): 603-14.

We claim:

1. A pharmaceutical composition comprising N-[3-(1,3-benzodioxol-5-yl)-3-(2-methoxyphenyl)propyl]-N-benzyl-propanamide or a pharmaceutically acceptable salt thereof, and a pharmaceutically acceptable carrier.

\* \* \* \* \*

UNITED STATES PATENT AND TRADEMARK OFFICE
CERTIFICATE OF CORRECTION

| | |
|---|---|
| PATENT NO. | : 8,138,356 B2 |
| APPLICATION NO. | : 12/253009 |
| DATED | : March 20, 2012 |
| INVENTOR(S) | : Jaideep Chaudhary and William Garland et al. |

It is certified that error appears in the above-identified patent and that said Letters Patent is hereby corrected as shown below:

On the Title Page, Item (73), the assignee should be AngioGenex, Inc.

Signed and Sealed this
Fourth Day of September, 2012

David J. Kappos
*Director of the United States Patent and Trademark Office*